United States Patent [19]
Clemmer et al.

[11] Patent Number: 6,148,814
[45] Date of Patent: Nov. 21, 2000

[54] METHOD AND SYSTEM FOR PATIENT MONITORING AND RESPIRATORY ASSISTANCE CONTROL THROUGH MECHANICAL VENTILATION BY THE USE OF DETERMINISTIC PROTOCOLS

[75] Inventors: Terry P. Clemmer; Thomas D. East, IV; Alan H. Morris, all of Salt Lake City; James F. Orme, Jr., Park City; George E. Thomsen, Salt Lake City; C. Jane Wallace, Salt Lake City; Lindell K. Weaver, Salt Lake City; Mary R. Suchyta, Salt Lake City, all of Utah

[73] Assignee: IHC Health Services, Inc, Salt Lake City, Utah

[21] Appl. No.: 08/613,728

[22] Filed: Feb. 8, 1996

[51] Int. Cl.$^7$ .................................................. A61M 15/00
[52] U.S. Cl. .................... 128/200.24; 128/898; 500/529; 500/538
[58] Field of Search ..................................... 600/300, 301, 600/529, 532, 538; 128/898, 200.24

[56] References Cited

U.S. PATENT DOCUMENTS

| | | | |
|---|---|---|---|
| 4,730,259 | 3/1988 | Gallant | 364/513 |
| 4,731,725 | 3/1988 | Suto et al. | 364/415 |
| 4,733,354 | 3/1988 | Potter et al. | 364/415 |
| 4,839,822 | 6/1989 | Dormond et al. | 364/513 |
| 4,872,122 | 10/1989 | Altschuler et al. | 364/554 |
| 5,005,143 | 4/1991 | Altschuler et al. | 364/554 |
| 5,023,785 | 6/1991 | Adrion et al. | 364/413.08 |
| 5,072,383 | 12/1991 | Brimm et al. | 364/413.02 |
| 5,126,957 | 6/1992 | Kaufman et al. | 364/479 |
| 5,330,505 | 7/1994 | Cohen | 607/6 |
| 5,355,893 | 10/1994 | Mick et al. | 128/719 |
| 5,413,110 | 5/1995 | Cummings et al. | 128/696 |
| 5,452,714 | 9/1995 | Anderson et al. | 128/205.11 |
| 5,485,850 | 1/1996 | Dietz | 128/716 |
| 5,560,352 | 10/1996 | Heim et al. | 128/203.12 |
| 5,752,509 | 5/1998 | Lachmann et al. | 128/204.23 |

OTHER PUBLICATIONS

*Critical Care Algorithms,* R.F. Armstrong et al. eds., Oxford Univ. Press, (1991), pp. 18–29.

G.O. Barnett et al., "DXplain—An Evolving Diagnostic Decision–Support System", *JAMA* (Jul. 3, 1987) vol. 258 No. 1, pp. 67–74.

V.K. Bhutani, et al., "Adaptive Control of Inspired Oxygen Delivery to the Neonate", *Pediatric Pulmonology* 14:110–117 (1992).

(List continued on next page.)

*Primary Examiner*—Dinh X. Nguyen
*Attorney, Agent, or Firm*—Lloyd W. Sadler; Daniel P. McCarthy

[57] ABSTRACT

A method and system for managing mechanical ventilation of patients with respiratory disorders is described. The main objective of the system is to generate executable instructions for patient care which take into account a large number of parameters of patient condition and ventilation. Data regarding the state of the patient are stored in a database. Patient data are processed according to a set of protocols which contain rules for patient care decisions arranged in a logical sequence to generate detailed, executable instructions for patient care. Instructions are updated when new data are entered into the database. The data can be acquired in an automated fashion, or the clinician can be instructed to collect and enter new data into the clinical database. Likewise, patient care instructions can be carried out automatically or manually, but it is preferred that instructions are carried out manually as a safety check. The preferred embodiment of the invention includes a computer system, software for processing patient data, and a display device for presenting patient care instructions to the clinician. The system maintains a record of patient data, patient care instructions, whether instructions were followed by the clinical staff, and if not, a reason why.

10 Claims, 27 Drawing Sheets

Microfiche Appendix Included
(3 Microfiche, 174 Pages)

OTHER PUBLICATIONS

S.M. Burns et al., "Weaning from Mechanical Ventilation: A Method for Assessment and Planning" *CEU Test* (Aug. 1991) vol. 2 No. 3, pp. 372–389.

M. Dojat et al., "A Knowledge–Based System for Assisted Ventilation of Patients in Intensive Care Units" *International Journal of Clinical Monitoring and Computing* 9:239–250 (1992).

H. Don, *Decision Making in Critical Care,* B.C. Decker Inc., (1985) pp. 62–67, 84–89, 102–103, 108–119.

T.D. East et al., "A Strategy for Development of Computerized Critical Care Decision Support Systems," *International Journal of Clinical Monitoring and Computing* 8:263–269 (1992).

T.D. East et al., "A Successful Computerized Protocol for Clinical Management of Pressure Control Inverse Ratio Ventilation in ARDS Patients" *Chest* (1992) 101:697–710.

S. Henderson et al., "Performance of Computerized Protocols for the Management of Arterial Oxygenation in an Intensive Care Unit" *International Journal of Clinical Monitoring and Computing* 8:271–280 (1992).

M.C. Higgins, "The Role for Artificial Intelligence in Critical Care" in *Decision Support Systems in Critical Care,* Shabot & Gardner, eds., Springer–Verley, (1994) Ch. 24, pp. 354–395.

T.O. Horseman, "Expert Systems: Assistance for Health Care Practitioners and Educators" *Respiratory Care* (Nov. 1989) vol. 34 No. 11, pp. 993–1003.

J. Hunter et al., "Inform: Integrated Support for Decisions and Activities in Intensive Care" *International Journal of Clinical Monitoring and Computing* 8:189–199.

J.B. Karlinsky et al., eds. *Decision Making in Pulmonary Medicine,* B.C. Decker (1991) pp. 120–125, 144–145.

J.P. Kassier, "A Report Card on Computer–Assisted Diagnosis—The Grade: C" *The New England Journal of Medicine* (Jun. 23, 1994) vol. 330 No. 25, pp. 1824–1825.

R. Klar et al. "Medical Expert Systems: Design and Applications in Pulmonary Medicine" *Lung* (1990) Suppl. pp. 1201–1209.

S. Miksch, et al., "VIE–VENT: Knowledge–based Monitoring and Therapy Planning of the Artificial Ventilation of Newborn Infants" *Austrian Research Institute for Artificial Intelligence* (Oct. 1993) pp. 1–12.

P.E. Morozoff et al., "Closed–loop Control of SaO2 in the Neonate" *Biomedical Instrumentation & Technology* (1992) 26:117–123.

A.H. Morris, "Adult Respiratory Distress Syndrome and New Modes of Mechanical Ventilation: Reducing the Complications of High Volume and High Pressure" *New Horizons* (Feb. 1994) vol. 2 No. 1, pp. 19–34.

A.H. Morris et al., "Computer Applications" in *Principles of Critical Care,* Hall et. al., eds. McGraw–Hill (1992) Part II, Ch. 41, pp. 500–514.

A.H. Morris, "Protocol Management of Adult Respiratory Distress Syndrome" *New Horizons* (Nov. 1993) vol. 1 No. 4, pp. 593–602.

A.H. Morris et al., "Randomized Clinical Trial of Pressure–controlled Inverse Ratio Ventilation and Extracorporeal CO2 Removal for Adult Respiratory Distress Syndrome" *American Journal of Respiratory and Critical Care Medicine* (1994) vol. 149, pp. 295–305.

A.H. Morris et al., "Paradigms in Management" in *Pathophysiologic Foundations of Critical Care* M.R. Pinsky et al. eds., Williams & Wilkins (1993) Ch. 12, pp. 193–206.

R. Rudowski et al., "Lung Function Analysis and Optimization During Artificial Ventilation. A Personal Computer–based System" *Computer Methods and Programs in Biomedicine* (1990) 31:33–42.

K. Saito et al., "Medical Diagnostic Expert System Based on PDP Model" IEEE Inter. Conf. on Neural Networks (Jul. 24, 1988) pp. 255–262.

N. Shahsavar, et al., "KAVE: A Tool for Knowledge Acquisition to Support Artificial Ventilation", *Computer Methods and Programs in Biomedicine* (1991) 34:115–123.

J.H. Strickland, Jr. et al., "A Computer–controlled Ventilator Weaning System: A Clinical Trial", *Chest* (Apr. 1993) vol. 103 No. 4, pp. 1220–1226.

F.T. Tehrani, "A Microcomputer Oxygen Control System for Ventilatory Therapy," *Annals of Biomedical Engineering* (1992) vol. 20, pp. 547–558.

*Principles and Practice of Mechanical Ventilation,* M.J. Tobin, ed. (1994) McGraw–Hill, Inc.

Debra Carlson, "Verification and Validation Algorithms for Data Used in Critical Care Decision Support Systems", Oct. 1995, 19th Annual Symposium on Computer Applications in Medical Care, New Orleans, LA.

Thomas D. East, "Medical Informatics Academia and Industry: A Symbiotic Relationship that May Assure Survival of both Through Health Care Reform", Oct. 1995, 19th Annual Symposium on Computer Applications in Medical Care, New Orleans, LA.

R. Matthew Sailors, "A successful Protocol for the Use of Pulse Oximetry to Classify Arterial Oxygenation into four Fuzzy Categories", Oct. 1995, 19th Annual Symposium on Computer Applications in Medical Care, New Orleans, LA.

Jane Wallace, Cost Effective Computerized Decision Support: Tracking Caregiver Acceptance at the Point of Care:, Oct. 1995, 19th Annual Symposium on Computer Applications in Medical Care, New Orleans, LA.

Thomas East, Alan Morris, Jane Wallace, Donna Pope, Debra Carlson, Richard Sailors, "Can Pulse Oximetry be used to Reliably Predict Arterial Oxygenation?", Society of Critical Care Medicine Annual Meeting, Jan. 31, 1995–Feb. 4, 1995.

Thomas D. East, "A Model Based Simulator for Testing Rule–Based Decision Support Systems for Mechanical Ventilation of ARDS Patients", Nov. 5, 1994, 18th Annual Symposium on Computer Applications in Medical Care, Washington, D.C.

Alan H. Morris, "Ethical Implications of Standardization of ICU Care with Computerized Protocols", Nov. 5, 1994, 18th Annual Symposium on Computer Applications in Medical Care, Washington, D.C.

The handout "Oxygenation Protocols for Patients with ARDS" was made available during seminar presentations at the following locations on the indicated dates: University of Pittsburgh, Pittsburgh, PA, Jul. 27, 1995; Harborview Medical Center, Seattle, WA, Apr. 10, 1995; Mass. General Hospital, Washington, D.C., Jan. 1995; Mass. General Hospital, Boston, MA, Dec. 4, 1994; University of Texas Health Sciences at Houston—Herrman Hospital, Houston, TX, Oct. 9, 1994.

The handout "Rule Based Decision Support Systems for Management of Mechanical Ventilation—Overview of Protocols" was made available during seminar presentations at the following locations on the indicated dates: University of Pittsburgh, Pittsburgh, PA, Jul. 27, 1995; Harborview Medical Center, Seattle, WA, Apr. 10, 1995; Mass. General Hospital, Washington, D.C., Jan. 1995; Mass. General Hospital, Boston, MA, Dec. 4, 1994; University of Texas Health Sciences at Houston—Herrman Hospital, Houston, TX, Oct. 9, 1994.

Alan H. Morris, M.D., "ARDS Clinical Trial Issues", in Adult Respiratory Distress Syndrome, C. Haslett & T. Evans, Eds., Chapman & Hall, London, 1994.

PATIENT IS BEING SUPPORTED WITH TRADITIONAL THERAPY

DO YOU WANT TO:

1. REVIEW PROTOCOL INSTRUCTIONS?
2. REVIEW CURRENT STATUS OF PATIENT?
3. GIVE REASONS FOR NOT FOLLOWING INSTRUCTIONS?
4. GIVE REASONS FOR NON-PROTOCOL CPAP TERMINATION?
5. SUSPEND PROTOCOLS? * USE FOR TEMPORARY SUSPENSIONS *
6. END PROTOCOL SUSPENSION?
7. UPDATE PATIENT'S BAROTRAUMA STATUS
8. RUN PROTOCOLS BASED ON OXYGEN CLASSIFICATION?
9. RUN PROTOCOLS BASED ON MOST RECENT ABG?
10. ENTER PATIENT IN THE PROTOCOLS?
11. TAKE PATIENT OUT OF THE PROTOCOL? * USE ONLY WHEN THE PT HAS BEEN EXTUBATED AND/OR WILL NO LONGER BE MANAGED BY PROTOCOL *
12...EXIT

FIG. 1B

METHOD AND SYSTEM FOR PATIENT MONITORING AND RESPIRATORY ASSISTANCE CONTROL THROUGH MECHANICAL VENTILATION BY THE USE OF DETERMINISTIC PROTOCOLS

A copy of the source code used in an example of the preferred embodiment of the invention is attached hereto as microfiche Appendix A which has 3 pages and 174frames. The code in Appendix A is written in the C programming language and is to be run on an Emtek System 2000 ICU information system, version 4.1. It is assumed that the system includes and Emtek protocol engine and a SUN or IBM workstation. This source code represents one element of one preferred embodiment of the invention. It should be understood that the inventive concepts could be implemented in ways other than those shown in the microfiche appendix without departing from the inventive concept.

A. THE FIELD OF THE INVENTION

The present invention relates to the field of expert systems and decision support systems for the management of patient care. In particular, this invention relates to the management of patients undergoing ventilatory assistance, and in particular those with respiratory disorders. These patients are mechanically ventilated, often for extended periods, to maintain suitable arterial oxygenation and pH. Many types of data are available which indicate the response of the patient to the disease and to mechanical ventilation. Due to the large amount of data it is often difficult for clinicians to identify a single optimal approach to regulation of ventilation. As a result, there is variability of treatment between clinicians, for a given patient and expression of disease, and variability of treatment of different patients showing the same expression of disease, by the same clinician, making it difficult to compare approaches and correlate particular approaches with successful patient outcome. Throughout the specification, the term "clinician" will be used to refer to physicians, nurses, respiratory therapists, technicians, and any others who are involved in delivering patient care. The invention serves to standardize care, and will play an important role in Continuous Quality Improvement efforts. Further, traditional treatment of such patients requires frequent clinician visits to evaluate data and make appropriate ventilator adjustments. It would be preferable to provide ventilator adjustment on a frequent basis without requiring the continual presence of a clinician. Accordingly, there is a need for methods for combining medical decision-making expertise with patient data within a logical framework in order to generate specific instructions (orders) for patient treatment.

B. THE BACKGROUND ART

It is well known in the prior art to use mechanical ventilation in patients who are unable maintain suitable arterial oxygen partial pressure and pH without assistance. In early ventilators, mechanical or pneumatic systems (e.g. piston pump, bellows) controlled the amplitude and timing of flow or pressure of gas delivered to the patient. Ventilatory rate and flow or pressure were typically adjusted manually. Later, servo-controlled proportional gas delivery valves were introduced; because these valves are electronically controlled, computer control of ventilator function became possible. In most currently available mechanical ventilators, the volume, flow, pressure and/or timing of ventilation are controlled by computer.

Because various factors influence the response of the patient to mechanical ventilation, simply regulating ventilator parameters does not necessarily maintain the patient's arterial pH or oxygen partial pressure at the desired levels. Monitoring systems with integrated alarms and alerts have been developed to notify the clinician if patient parameters are not within the target range during mechanical ventilation. For example, such a system has been patented by Mick et al. (U.S. Pat. No. 5,355,893, which is incorporated herein by reference). This type of system alerts the clinician when there is a problem, but offers no guidance in resolving the problem.

A number of systems have been developed which provide for closed-loop, filly-automated control of ventilation. Examples are systems reported by Bhutani et al. (Pediatric Pulmonology, Vol. 14, pp. 110–117, 1992), East (*Principles and Practice of Mechanical Ventilation*, Ch. 12, McGraw-Hill, Inc., 1994), Morozoff and Evans (Biomed. Instr. Tech., Vol. 26, pp. 117–223, 1992), Rudowski et al.(Comp. Meth. Progr. Biomed, Vol. 31, pp. 33–42, 1990), and Tehrani (Ann. Biomed. Engr., Vo. 20, pp. 547–558, 1992), all of which are incorporated herein by reference. In general, these systems maintain a single patient parameter at a desired constant value, by modulating a single parameter of ventilation, while holding other parameters constant. For example, oxygen saturation may be regulated by adjusting the percent oxygen in the inspired gas mixture, or end tidal $CO_2$ may be regulated by controlling the frequency of ventilation, while holding the breath size constant. While this approach is often effective, in some cases modulating a single parameter is insufficient to maintain oxygenation or pH at the desired level. None of the currently available closed-loop systems is capable of supporting a patient who has a serious respiratory disorder and who is in need of prolonged ventilatory support.

Expert systems make it possible to make decisions or classification of data in an automated fashion, by applying "expert knowledge" to the analysis of data. Expert systems may be structured in a number of ways. For example, a rule-base (decision tree) system uses expert-derived rules to generate a single solution for a given set of input data. Bayesian systems take into account the probabilistic nature of many decisions, and generate multiple possible solutions, each with an associated probability of correctness (for example, Altschuler et al., U.S. Pat. Nos. 4,839,822 and 5,005,143, incorporated herein by reference). Other expert systems are not set up with explicit rules, but rather are trained to make decisions by being presented with various sample data sets and the associated correct decision (according to one or more experts). Examples of such "learning systems" are described in Saito and Nakano (Proceedings, IEEE Inter. Conf. on Neural Networks, Jul. 24–27, 1988) and Gallant (U.S. Pat. No. 4,730,259, incorporated herein by reference).

Decision support tools which are also expert systems have been developed for use in various areas of medicine. One prior art application of expert systems is to make a diagnosis on the basis of a set of facts pertaining to the patient. Such a system is presented by Barnett et al. (JAMA, Vol. 258, pp. 67–74, 1987). Potter et al. (U.S. Pat. No. 4,733,354) describe a system for making a dermatological diagnosis. Adrion et al. (U.S. Pat. No. 5,023,785) describe an expert system for making diagnoses in the field of hematology. Suto et al. (U.S. Pat. No. 4,731,725) describe a system for making a diagnosis on the basis of medical images. Systems designed for use in pulmonary medicine include those of Klar and Zaiss (Lung, Suppl. pp. 1201–1209, 1990), Miksch et al.

(Proc. 4th Conf. Art. Intell. in Med. Europe, October 1993, pp. 1–18), and Shahsavar et al. (Comp. Meth. Prog.Biomed., vol. 34, pp. 115–123, 1991). While such systems show promise, there are still many drawbacks which need to be resolved (Kassirer, New Eng. J. Med., Jun. 23, 1994, pp. 1824–1825). This and the preceding journal articles and patents are incorporated herein by reference.

Other expert systems generate suggestions of treatments for various medical problems, such as physical trauma (Dormond et al., U.S. Pat. No. 4,839,822, incorporated herein by reference). A few systems provide for integrated support in Critical (Intensive) Care (Higgens, *Decision Support Systems in Critical Care,* Ch. 24, Gardner and Shabot, Eds., Springer Verlag, 1994; Hunter, Int. J. Clin. Mon. and Comp., Vol. 8, pp. 189–199, 1991). Both of these texts are incorporated herein by reference.

Most decision support tools give instructions for patient care which are non-specific; for example, a list of possible treatments, each with an associated probability of correctness, or a single, general guideline for treatment, which must be interpreted and could be carried out in various ways depending on the personal preference of the clinician. In either case, the final decision on patient care is left to the discretion of the attending clinician. This is a drawback if it is necessary that care be delivered consistently to different patients, who may be under the care of different doctors. It is often desirable that instructions are provided which can be carried out by individuals who do not have authority to make patient treatment decisions independently (e.g. nurses, respiratory therapists, technician, etc.). In these cases, a system which generates executable instructions for patient care which are sufficiently detailed that they are not subject to interpretation by the person who carries them out would be preferable.

Expert systems are also available which provide guidance relating to the weaning of patients from mechanical ventilation. Examples are Burns et al. (Clin. Iss., Vol. 2, pp. 372–390, 1991), Dojat et al. (Int. J. Clin. Mon. Comp., vol. 9,pp. 239–250, 1992), Miksch (Proc. 4th Conf. Art. Intell. in Med. Europe, October 1993, pp. 1–8), and Strickland (Chest, Vol. 100, pp. 1096–1099, 1991) all of which are incorporated herein by reference.

Another approach for managing patient care is the use of "protocols" or decision trees in the form of paper-based flow diagrams. These also fall into the category of decision support tools. Protocols can be used in many areas of medicine. Protocols for handling a variety of disorders, including respiratory disorders, are published in *Decision Making in Critical care* (Hillary Don, Ed., B. C. Decker, Inc., Philadelphia, Pa., 1985) and *Critical Care Algorithms* (Armstrong et al, Eds., Oxford University Press, New York, 1991), both of which are incorporated herein by reference. *Decision Making in Pulmonary Medicine* (Karlinzky et al., Eds, B. C. Decker, Philadelphia, Pa., 1991) includes protocols which aid decision making in pulmonary medicine. These three texts are incorporated herein by reference. The protocols or decision trees published in these books provide sequential decision points and instructions for the diagnosis and treatment of patients. The instructions, however, are general and require interpretation by the physician. For example, in the protocol for "Weaning from Mechanical Ventilation" found on p. 124–125 of *Decision making in Pulmonary Medicine,* if the patient does not fulfill weaning criteria, the protocol advises the physician to "correct metabolic parameters". Although a list a possible metabolic problems is provided, no specific, executable instructions are provided for correcting these problems, or for identifying the underlying metabolic problem on the basis of the unfulfilled weaning criteria. Such protocols serve as guidelines for patient care but could only be used by someone with medical expertise who brings additional information and who is empowered to make judgements about care.

A different approach can be taken however. In a paper by East et al., (CHEST, Vol. 101, pp. 697–710, 1992, incorporated herein by reference) the use of a computerized protocol for the clinical management of Pressure Control Inverse Ratio Ventilation (PCIRV) is described. The protocol disclosed therein generates specific instructions for adjusting various parameters to regulated PCIRV. Morris and Gardner (*Principles of Critical Care,* Part II, Ch. 41, McGraw-Hill, Inc., 1992) provides an overview of computers in critical care, also incorporated herein by reference. As an example, a computerized protocol for inverse ratio ventilation (IRV) is presented. In the protocols described in both of these papers, detailed instructions for adjusting several parameters of ventilation are generated, and these serve as a set of dynamic standing orders for the clinical staff.

Virtually all currently available expert systems operate on a non-continuous basis. That is, when it is desired that the system generate a diagnosis or treatment advice, data are entered and the desired information generated. One system which does operate on a continuous basis is a system for delivery of medication to elderly patients (Kaufman et al, U.S. Pat. No. 5,126,957, incorporated herein by reference). This system dispenses certain medications to the patient on a pre-programmed schedule. It will dispense other medications to the patient on demand, providing that such medication is indicated by the health parameters of the patient and such medication has not been dispensed within a prescribed preceding time period.

Also of relevance to the present invention is the arena of hospital information systems. Hospital information systems are computer systems used in hospitals to keep track of large amounts of patient data, both administrative and clinical. Administrative data typically include admission, discharge, transfer, demographic and billing information. In the past, hospitals generally used separate computer systems for handling patient clinical data (e.g., monitoring and laboratory data). Hospital information systems may be used to maintain task lists which are updated automatically as actions are charted (Brimm et al., U.S. Pat. No. 5,072,383, incorporated herein by reference). Recently, systems have become available which are capable of integrating both types of patient data, that may be available at the patient's bedside. These systems make it possible to have various patient data and software available continuously at a patient's bedside, that is, at the point of care.

II. SUMMARY OF THE INVENTION

The invention comprises a method and system for managing mechanical ventilation of patients with respiratory disorders. The system was particularly designed for the management of patients with ARDS (Adult or Acute Respiratory Distress Syndrome) patients. The system includes equipment for monitoring clinical data and/or equipment for uploading or entering previously measured clinical data, a computer system, software for processing the clinical data, equipment for presenting patient care instructions to the clinician, and equipment for carrying out patient care instructions in an automated fashion. Instructions for control of mechanical ventilation of patients, which are sufficiently explicit to serve as standing orders, are generated from expert-derived rules assembled in the form of protocols. The protocols are carried out by a system which monitors various data representing the patient state. The instructions may be carried out automatically by the system or manually by a clinician. A number of protocols for regulating various aspects of ventilation are used by the system. When a protocol is activated, if a patient parameter is not within the target range, one or more specific, executable instructions (or orders) for adjusting settings on the ventilator are presented to the clinician. If the data on which treatment decisions are made are not complete or up-to-date, instructions are generated for collecting and recording new patient data, in order to correct the data deficiency. These data can be collected in an automated fashion, or the clinician can be instructed to collect and enter new data into the clinical database. The inventors prefer that the clinician carry out the instructions manually, as a safety check. In this case, the system does not control ventilation directly; all adjustments are made by a clinician, who has the option of declining instructions generated by the system. The inventive system maintains a record of patient data, patient care instructions, and whether those instructions were executed. The instructions of the system are sufficiently specific to be executed by clinical personnel with basic ICU and ventilator management experience, without further interpretation, interpolation, or modification.

It is a goal of the present invention to provide a means for synthesizing patient data and medical expertise on management of patients undergoing mechanical ventilation, in such a way that detailed instructions for patient care are generated. This is accomplished by utilizing a protocol set made up of detailed medical decision-making rules arranged in a logic sequence. The benefit of generating detailed executable instructions is that they can be carried out by personnel who do not have the authority to make medical treatment decisions themselves. Therefore, patient care can be provided without requiring frequent attendance by a physician.

It is a goal of the present invention to provide a means for delivering patient care in a consistent manner. This is possible because the same instruction will always be generated if the patient parameters are the same. This allows comparison and evaluation of different patients and treatments to be performed, and eliminates the problems of variability of care decisions between patients, for the same clinician, and between clinicians.

It is a goal of the present invention to monitor patient care and patient parameters continuously over time in order to generate instructions for patient care which reflect the rates-of-change of clinical data as well as the current state of clinical data. This is accomplished by having the inventive system run continuously and prompt the clinician to enter data at appropriate intervals. Continuous monitoring and control of patient treatment improves quality of patient treatment and reduces the need for physician intervention.

It is a goal of the invention to maintain a record of patient expression of disease and patient treatments (clinician response) over time. This is accomplished by saving patient data, patient treatment instructions, and information regarding whether said instructions were carried out. This complete record of patient condition and treatment is valuable for determining where problems in patient treatment arose, proving completeness and appropriateness of patient care, and assessing success of patient treatment and of the logic from which it was derived.

It is a goal of the invention to monitor and control oxygenation of a patient during CPPV. Oxygen partial pressure of the patient is controlled by adjusting PEEP and $F_IO_2$. Well-controlled oxygenation during CPPV ventilation is an important goal of clinical care during extended mechanical ventilation.

A goal of the invention is to monitor and control $pH_a$, VR, and VT during CPPV. VR and VT are adjusted directly on the ventilator, while $pH_a$ is indirectly controlled by adjusting these and related variables. It is desirable to maintain $pH_a$, VR, and VT within specified limits during CPPV, to ensure safe mechanical ventilation and to achieve the pH level that constitutes a goal of clinical care.

A goal of the invention is to produce a controlled increase or decrease in tidal volume in response to arterial pH. Gradual adjustment of tidal volume may change pH when changing rate alone has little effect.

A goal of the invention is to monitor and control oxygenation of a patient during CPAP weaning. Oxygenation is controlled by adjusting $F_IO_2$ or CPAP. Successful maintenance of a patient on CPAP is one technique for weaning the patient from ventilation. Inability to maintain oxygenation at an acceptable level during CPAP indicates that the patient is not yet ready to resume spontaneous ventilation.

A goal of the invention is to test whether a patient is ready to be weaned from mechanical ventilation. The readiness of the patient for weaning is determined by measuring the patient's spontaneous breathing rate and tidal volume for a brief period of time, and may include reducing the ventilator rate to determine the rate at which the patient begins to breathe spontaneously. This weaning test has the benefit that it may be used consistently with all patients to ensure that weaning is carried out with a standardized procedure and in an efficient and well-regulated manner which minimizes stress on the patient.

III. BRIEF DESCRIPTION OF THE DRAWINGS

FIG. 1B is the main menu from which the protocols are selected.

IV. DETAILED DESCRIPTION OF THE INVENTION

The following definitions will be used throughout the description of the invention:

TABLE 1

Definitions

| | |
|---|---|
| 900C4 | Siemens 900C ventilator |
| ABG | Arterial Blood Gas |
| ARDS | Adult or Acute Respiratory Distress Syndrome |
| clinician | physician, nurse, respiratory therapist, respiratory technician |
| CPAP | continuous positive airway pressure support |
| CPPV | controlled positive pressure ventilation (also known as Continuous Mechanical Ventilation (CMV), Volume Controlled Ventilation, etc.) |
| DBP | diastolic blood pressure |
| $F_IO_2$ | fraction of inspired oxygen |
| $HCO_3^-$ | serum bicarbonate concentration |
| HIS | hospital information system |
| HR | heart rate (beats/min) |
| H. Veolar | Hamilton Veolar ventilator |
| I:E | inspiratory time:expiratory time ratio |
| MIP | maximum inspiratory pressure |
| MR | "machine rate" (total ventilatory rate) |
| $PaCO_2$ | arterial carbon dioxide partial pressure |
| $PaO_2$ | arterial oxygen partial pressure |
| PB7200 | Puritan Bennet 7200 ventilator |
| PEEP | positive end expiratory pressure |
| $pH_a$ | arterial pH |
| $P_{peak}$ | peak airway pressure |
| $P_{plat}$ | end inspiratory plateau pressure (cm $H_2O$) |
| $SaO_2$ | arterial oxygen saturation |
| SBP | systolic blood pressure |
| $SpO_2$ | arterial oxygen saturation (from pulse oximeter) |
| $V_E$ | expired minute ventilation (L/min) |
| $V_R$ | ventilatory rate (breaths/min) set on ventilator |
| $V_T$ | tidal volume (ml) |
| MD | physician |
| RT | respiratory technician |
| RN | registered nurse |
| $mmH_g$ | (millimeters of mercury; a measure of pressure) |
| $cmH_2O$ | (centimeters of water; a measure of pressure) |

The abbreviations and terms listed above are well-known in the prior art, as are methods and apparati by which they can be measured from a patient and/or calculated.

Figure 1A:
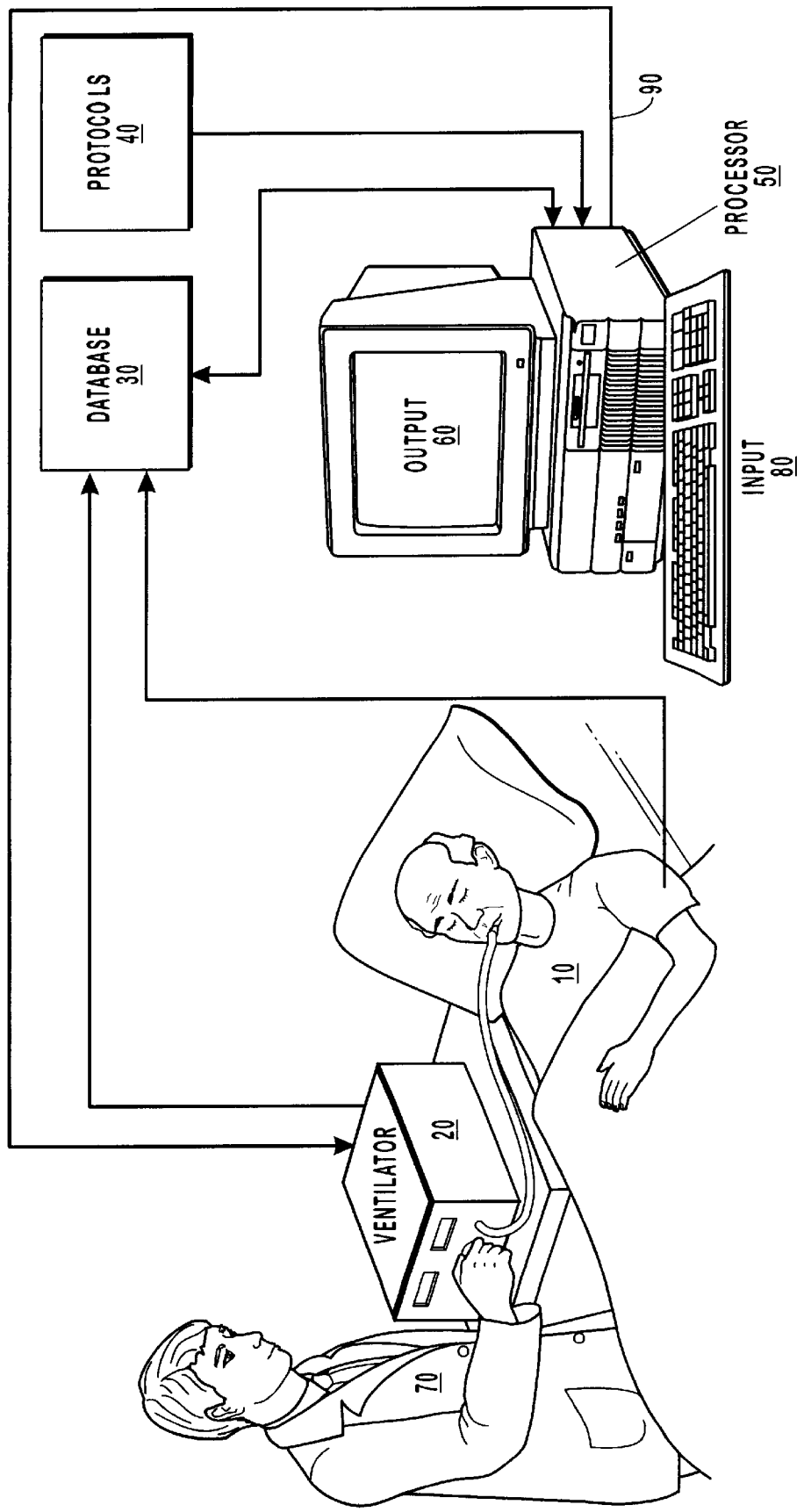
FIG. 1A is a schematic diagram of the invention used in management of patient treatment.

A schematic diagram of the invention in use with a patient is presented in FIG. 1A. The patient 10 is mechanically supported by a ventilator 20. Ventilator 20 provides pressurized gas to the patient. Various ventilatory assistance parameters of ventilation can be set on said ventilator. Ventilators vary; most allow some or all of the following parameters to be set: VR (i.e. the number of breaths per minute), I:E, $F_IO_2$, PEEP, inspiratory time, pause time, ventilation mode, and VT or VE. In the present invention, the ventilator can be operated in two modes: the ventilator can provide continuous positive airway pressure ventilation (CPPV) or continuous positive airway pressure (CPAP)—in which case the ventilation is not actually used to ventilate the patient (i.e., perform breathing), but simply provides a positive pressure gas source which is used by a patient who takes breaths without further assistance. Various patient parameters are measured, including HR, blood pressure (including SBP & DBP), spontaneous respiratory rate, spontaneous tidal volume, and spontaneous inspiratory pressure.

Moreover, if CPPV is used, the ventilatory rate (VR) may be controlled by the ventilator (patient mode="controlled"), or breaths may be triggered by both the ventilator and the patient, in which case the patient mode is said to be "assisting."

In the presently preferred embodiment of the invention, some of these parameters are loaded into patient data base 30 directly from monitoring equipment, while other values are read from monitoring equipment and entered into patient data base 30 by hospital personnel. MR, MIP, $P_{peak}$ and $P_{plat}$ are typically read off the ventilator. In some cases, gas flows and various sensing devices may be used for monitoring patient parameters. $HCO_3$, $PaCO_2$, and $pH_a$, are typically obtained from ABG measurements made in a lab, but could also be measured with an in-dwelling sensor. Arterial oxygen saturation may be calculated from ABG ($SaO_2$) or measured with a cooximeter. $SpO_2$ is arterial oxygen saturation measured with the use of a pulse oximeter. HR, DBP and SBP can be measured by various methods. HR can be measured with a stethoscope, EKG monitor, blood pressure monitor, pulse oximeter or by an in-dwelling arterial line. Blood pressure measurements can be made with a cuff or blood pressure monitor, or with an in-dwelling arterial line. Any of these methods and sensing devices are suitable for use in the invention. Ultimately it may be preferred for monitoring equipment to periodically automatically update the database with all relevant data concerning the state of the patient. If equipment which permits continuous monitoring is used (e.g. in-dwelling sensors or non-invasive but continuous monitoring devices with electrical or optical sensors) it would also be possible to update data on a near continuous basis. This would, however, require some modification of the protocols, which currently assume updating of patient data and modification of patient treatment at intervals. The invention is not limited by the method by which the data are measured and stored in patient data base 30. Additional patient data which are entered once or updated very infrequently, such as height, weight, age, and gender are also stored in patient data base 30. The type of ventilator being used, whether the patient has barotrauma (e.g. pneumomediastinum, pneumothorax, subcutaneous and interstitial emphysema, cystic alterations of the lung), whether the patient is intubated, whether paralytic agents have been used, and whether the ventilation is assisting the patient (patient triggering ventilator) or controlling the patient (patient not triggering ventilator), are also stored in patient data base 30.

The invented system comprises patient data base 30, protocol set 40; a processor 50 for processing selected data from said patient data base according to protocol set 40 to generate specific instructions for patient management; an output device 60 whereby said instruction is made known to a clinician 70, and an input device 80 whereby said clinician can signal that each instruction has been accepted or declined. Alternatively, the instruction can be carried out automatically, without clinician intervention, by sending a suitable control signal to ventilator 20 via control line 90. In this alternative embodiment it is assumed that said ventilator is capable of being controlled by a digital input signal. Ventilators of this type are currently available and are known to those with ordinary skill in the use of mechanical ventilators. If the clinician 70 accepts the instruction produced by the inventive system, he or she will carry out the instruction by making appropriate adjustments to ventilator 20 or adding new data to the data base. The inventive system therefore accomplishes closed loop control of ventilation, but it may or may not control the ventilator directly. By having a member of the hospital personnel review the instruction before carrying it out, instructions which appear to be inappropriate may be declined.

The heart of the invention's intelligence is protocol set 40, which is made up of a number of protocols, each of which contains logic for handling a particular aspect of respiratory care. The protocol logic has been designed with the understanding that sufficient knowledge is available concerning the management of ARDS patients that, given a particular patient data set and history, it is possible for the system to make a patient treatment decision to generate a one or more specific, executable instructions for patient care. In fact, the instructions are of sufficient detail that they serve as a set of dynamic "standing orders" for patient treatment that change as the patient's expression of the disease changes. The medical logic on which the protocols are based was developed through a consensus process by a group of medical personnel (M.D.s, R.N.s, R.T.s and medical informaticists). In each run through the protocols, patient data are subjected to a set of expert-derived rules and comparisons with target values and ranges in a logical sequence to produce detailed, executable patient care instructions.

In the preferred embodiment, the invention has computer code running on a hospital computer system. Patient data base 30 then comprises a data base or other data storage device also present on the hospital computer system, and accessible by said software. In the preferred embodiment of the invention, processor 50 then comprises the computer, output device 60 is preferably a CRT or other type of computer monitor, and input device 80 is preferably a keyboard. Alternatively, input device 80 could be a mouse, track ball or other input device.

In the preferred embodiment of the invention, patient data may be ported directly to said database from patient monitoring equipment and/or entered into the database by hospital personnel via input device 80, subsequent to performance of lab tests, x-rays, or other examinations. Operation of the system is continuous. When new patient data are entered, protocols are activated to determine whether new instructions for patient treatment should be generated. If new patient data are not entered at the appropriate intervals, the protocols generate an instruction to enter new data. A record of the instructions generated and displayed, the data and logical sequence used to generate those instructions, and the times of the instructions, is stored in the database for the purpose of verifying patient treatment and providing an audit trail for protocol performance. Whether an instruction was accepted or declined, and the reason if the instruction was declined, are also stored.

The preferred embodiment of the invention may be practiced in connection with various computer systems, providing that certain requirements are met. Practice of the invention requires the use of an ICU information system with a monochrome monitor. Some form of removable media (e.g. tape, disk, etc.) is also required. The HIS used must include a Respiratory Care and Blood Gas Charting System, Hemodynamic Charting, ADT System, and charting of demographics information (height, weight, age, sex, etc.). The system must have the ability to display messages (of preferably 256 characters or less) as result of execution of the rules; furthermore, it must have the ability to store and subsequently display previously generated messages. The system must include facilities for producing printouts of messages, and for storing protocol related data onto removable media (e.g. tapes or disks).

It must be possible to create new data elements in data base and create new data entry screen and menus. The system on which the protocols are run must have facilities for creating and running rules (logic modules). It must be possible to trigger execution of the rules by either entry of particular types of data into the system or selection of a particular menu option.

It must be appreciated that the software used in the practice of the invention may be modified in such a way that it is compatible with various hospital information systems, databases, and hardware, and that such modifications and variations would be known to those of ordinary skill in the art and are considered to fall within the scope of the invention.

In one alternative embodiment, the method of the invention may be implemented from protocols written on paper or provided via other display media in the form of flow diagrams or rule sets. This embodiment of the invention is less preferred if complex protocols are to be used; however, particularly for simpler forms of the protocols, satisfactory results may be obtained with this embodiment.

The operation of the invention can be more easily understood with reference to the following examples. Said examples are illustrative and are not intended to limit the scope of the invention. In some cases, comparison and decision steps made within a protocol must be performed in a specific order (as when a particular step is carried out only if a particular outcome is obtained in a previous step). However, in some cases, the order in which comparison and decision steps are made is not of any particular significance, and the same patient care instruction would be obtained if the order of the steps was changed. In the examples which follow, it should be appreciated that in many cases, the order of comparisons and decisions can rearranged and such reorderings are considered to fall within the scope of the invention.

EXAMPLE 1

The embodiment of the invention described in this example utilizes the source code presented in microfiche Appendix A and makes use of an Emtek System 2000, v 4.1 patch 20 hospital information system run on a Sun Sparc 5 work station. The hospital information system (HIS) runs system software which allows various medical record keeping tasks and other clinical tasks, including decision support, to be carried out. Terminals at each bedside provide access to the HIS data and programs. Multiple processors are present, so that multiple users can use the system at one time and multiple tasks can be carried out simultaneously.

Because the bedside terminals are used for multiple tasks, the inventive system is configured so that its software can run in the background while other tasks are being performed (i.e., software runs without visual display on the computer screen or auditory or other indications to the clinician that the software is running). Patient care instructions generated by the protocols are saved while the protocols are running in background mode. The protocols are started or suspended from a main menu such as the one shown in FIG. 1B. A small marker on the screen indicates to the user that an instruction has been generated. Current or previous instructions can be viewed by making the appropriate menu selection.

If data need to be updated the clinician will be instructed to collect and enter new data. When no change is to be effected with regard to data or ventilator adjustment, a message will be generated concerning the waiting period until the next action must be taken. If the clinician accepts an instruction, he or she then carries out that instruction. If the clinician declines an instruction, the reason for declining is entered and stored in the database and the protocol proceeds to generation of the next instruction.

The protocol logic used by the software of the preferred embodiment in the example is now described. Further detail of the software can be obtained by referring to microfiche appendix A.

The data elements shown in Table 2A & 2B are used in the protocols described in this example. Upper and lower limits for the normal ranges of the parameters are listed in Table 2A.

TABLE 2A

Flowchart Data Elements

| Flowchart Name | Description | Min | Max |
|---|---|---|---|
| $F_I O_2$ input | Fraction of Inspired Oxygen (× 100%) | 21 | 100 |
| $MR_{input}$ | Total respiratory rate (breaths/min.) | 2 | 80 |
| $PEEP_{input}$ | PEEP (cm $H_2O$) | 0 | 60 |
| $VR_{input}$ | Set machine rate (breaths/min.) | 1 | 45 |
| age | Patient's age (years) | 1 | 100 |
| barotrauma | Barotrauma (yes or no) | 0 | 1 |
| ctc | Tubing compliance (mL/cm $H_2O$) | 1 | 100 |
| DBP | Diastolic blood pressure (mmHg) | 15 | 200 |
| extubate | Extubation | | |
| gender | Gender (male or female) | | |
| $HCO_3$ input | $HCO_3$ from blood gas (mEq/L) | 5 | 60 |
| height | Height (centimeters) | 100 | 250 |
| HR | Heart rate (beats/min) | 20 | 300 |
| I:E ratio | I:E ratio | | |

TABLE 2A-continued

Flowchart Data Elements

| Flowchart Name | Description | Min | Max |
|---|---|---|---|
| insp time | Inspiratory Time | | |
| intubate | Intubation | | |
| MIP | Spont. Maximum Insp Pressure (cm $H_2O$) | 0 | −200 |
| $PaCO_2$ input | $PaCO_2$ from blood gas (mmHg) | 10 | 200 |
| $PaO_2$ input | $PaO_2$ from blood gas (mmHg) | 10 | 500 |
| paralytics | Paralyzed (yes or no) | | |
| pause time | Pause Time | 0 | 5 |
| $pH_a$ input | Arterial pH from blood gas | 6.6 | 7.8 |
| $P_{peak}$ | Peak pressure (cm H2O) | 15 | 120 |
| $P_{plat}$ | Plateau pressure (cm H2O) | 15 | 120 |
| $SaO_2$ | Arterial saturation from blood gas | 20 | 100 |
| SBP | Systolic blood pressure (mmHg) | 20 | 350 |
| $SpO_2$ abg | Pulse oximeter reading recorded with blood gas (%) | 40 | 100 |
| $SpO_2$ input | Pulse oximeter reading used to run the protocol. (%) | 20 | 100 |
| spon VR | Spont. respiratory rate (breaths/min) | 2 | 80 |
| spon VT | Spont. tidal volume measured (mL) | 1 | 1500 |
| $VE_{input}$ | Minute ventilation (L/min) | 1 | 25 |
| vent mode | Ventilator mode. Mode the ventilator is currently set | | |
| ventilator | Ventilator type | | |
| $VT_{input}$ | Set machine tidal volume (mL) | 1 | 1500 |

TABLE 2B

Internal Variables

| Flowchart Name | Description | Protocol used and/or set in |
|---|---|---|
| | Time when the last ABG was drawn | |
| | Bounce Time. Time when $F_I O_2$ was increased completing an $F_I O_2$ Bounce. | CPPV and CPAP Oxygenation Reduction |
| | Late time. Time ABG was drawn or $SpO_2$ was entered to run protocols. Look back from this time for all data used in the protocols. | Set: At the beginning of the protocols. Used: Everytime protocols get data. |
| | Tidal Volume Trial Time. Time when VT trial began. Used to determine if the tidal volume has timed out. | Increase VT Trial - controlled and Assisting |
| CPAP limit | CPAP limit | CPAP increase |
| delay time | Tidal volume delay time. Amount of time before a VT increase trial can be attempted | Set: Controlled and Assisting VT trials. Used: Assisting and Controlled ventilation. |
| wait end | Wait end time. Time when the wait time will be over | CPPV and CPAP Reduction |
| wait start | Wait time start. Start of time waiting for a decrease in $F_I O_2$. | CPPV and CPAP Oxygenation Reduction |
| wean delay time | Weaning Delay Time. Amount of time before a Weaning Assessment Trial can occur following a CPAP, Weaning Assessment failure or cancellation. | Set: Weaning Assessment Trial and Cancel Trial Used: CPPV Oxygenation Reduction |
| Bounce count | Bounce count. Bounce = decrease in $F_I O_2$ followed by an increase in $F_I O_2$ within 45 mins. without a change in PEEP, $F_I O_2$ or Mode before the increase. | CPPV and CPAP Oxygenation Reduction |

TABLE 2B-continued

Internal Variables

| Flowchart Name | Description | Protocol used and/or set in |
|---|---|---|
| $F_IO_{2\ set}$ | $F_IO_2$ Set. Intended setting for $F_IO_2$. | CPAP and CPPV Increase and Reduction, CPAP Vent, Weaning, Store Instructions |
| $MR_{baseline}$ | $MR_{baseline}$. Total rate entering a weaning trial. | Weaning Assessment Trial |
| Patient Mode | Last patient mode (not Vent Mode). Assisting or Controlled | Set: Assisting and Controlled Vent Used: CPPV Vent and Set Vent |
| $PEEP_{limit}$ | PEEP limit | CPPV Oxygenation Increase, Data Quality Check |
| $PEEP_{set}$ | PEEP Set. Intended setting for PEEP or CPAP. | |
| $pH_{a\ baseline}$ | Baseline $pH_a$ entering Increase VT Trial - Controlled | Increase VT Trial - Controlled |
| $pH_{a\ low}$ | Low Arterial pH. Lowest $pH_a$ allowed before calculating a new $VE_{goal}$. | Assisting and Controlled Ventilation |
| Trial | Status of the Trials: 0) No trial. 1) Wean trial. 2) CTV trial. 3) ATV trial. | |
| $VE_{input}$ | Minute ventilation in the ventilatory charging. VE setting on a Servo 900C. | Set: Get Vent Settings Used: CPPV Vent, Cont and Asst Ventilation, VT Trials, Set Vent. |
| $VE_{set}$ | Minute ventilation set. Setting on ventilator for minute ventilation | Set Ventilator |
| $VR_{baseline}$ | Baseline Ventilatory Rate. Ventilatory rate setting entering a weaning trial. Used to reset VR if it's changed during the trial. | Weaning Assessment Trial |
| $VR_{input}$ | Ventilatory rate in the ventilatory charging. Ventilatory rate patient is receiving (setting) | Set: Get Vent Settings Used: CPPV Vent, Cont and Asst Ventilation, VT Trials, Set Vent. |
| $VR_{set}$ | Ventilatory rate set. Intended setting for VR. | Set Ventilator |
| $VT_{baseline}$ | Baseline Tidal volume. Tidal volume entering a Increase VT Trial. $VT_{baseline} = VT_{corr\ insp}$ | Increase VT Trial - Assisting |
| $VT_{input}$ | Tidal volume in the ventilatory charting. Tidal volume patient is receiving (setting) | Set: Get Vent Settings Used: CPPV Vent, Cont and Asst Ventilation, VT Trials, Set Vent. |
| $VT_{set}$ | Tidal Volume set. Intended setting for VT. | Set Ventilator |
| Wait Time | The length of Waiting Period: 4, 8, or 24. | CPPV and CPAP Oxygenation Reduction |
| $\Delta PaO_{2\ est}$ | $\Delta PaO_{2\ est} = 1/(0.070312. - 0.00060345 \times SaO_2) - PaO_2$ input. Difference between $PaO_2$ estimated from last $SaO_2$ and the actual $PaO_2$ at that time | SPO2 logic |
| $BW_p$ | Predicted Body weight | Set: Data Quality Check Used: Weaning, Cont and Asst Ventilation, VT Trials, Set Vent. |
| $O_2$ Class | Oxygenation Classification | Set: Oxygenation Classification Used: CORE |
| $PaCO_2$ backup | $PaCO_2$ required for VE backup to achieve the pH goal (7.30) if the patient stops assisting the ventilator | |
| $PaCO_2$ goal | $PaCO_2$ goal. Arterial $PaCO_2$ required for the VE backup. | Assisting Mode Ventilation |
| $PaO_2$ estimated | Estimated $PaO_2$. Based on pulse oximeter reading | SPO2 Logic |
| $pH_{a\ backup}$ | Backup Arterial pH A calculated value that estimates what the pH will be if the patient stops assisting the ventilator | Assisting Mode Ventilation |
| $pH_{a\ goal}$ | Arterial pH goal. If the patients pH is out of range the pH goal (7.30) is used to determine the new VE. | Controlled and Assisting Mode Ventilation, Increase VT Trials - Controlled. |
| $pH_{a\ target}$ | pH target. Used only to determine if a Increase VT Trial for controlled patients is successful. | Increase VT Trials - Controlled |
| $P_{plat}$ | Plateau pressure | Controlled and Assisting Mode Ventilation, Increase VT Trials - Controlled. |
| trigger | what starts the protocol {ABG, SpO$_2$, Cancel Trial, Suspend Protocol, In Weaning trial (spont. parameters, vent drive test), In increase VT trial} | CORE |
| $VE_{backup}$ | Minute ventilation backup. Minute volume required to obtain the pH back | Assisting Mode Ventilation |
| $VE_{corr\ insp}$ | Minute ventilation corrected. Minute ventilation with the tubing compression factor removed | Set: Get Vent Settings Used: Cont and Asst Ventilation, VT Trials, Set Vent. |
| $VE_{goal}$ | Minute ventilation goal. Calculated minute ventilation required for the patient to maintain the target pH. | Controlled and Assisting Mode Ventilation, VT Trials, Set Vent. |
| $VR_{goal}$ | Ventilatory rate goal. Ventilatory rate required | Set Ventilator |

TABLE 2B-continued

Internal Variables

| Flowchart Name | Description | Protocol used and/or set in |
|---|---|---|
| | for the patient to obtain the $VE_{goal}$ | |
| $VR_{max}$ | Ventilatory rate maximum. 35 breaths per minute | Set Ventilator |
| $VR_{min}$ | Ventilator rate minimum. 6 breaths per minute | Set Ventilator |
| $VR_{temp}$ | Temporary Ventilatory Rate. Ventilatory rate needed to obtain the $VE_{goal}$ using the current VT | Controlled and Assisting Mode Ventilation, VT Trials, Set Vent. |
| $VT_{corr\ insp}$ | Tidal Volume corrected. Tidal volume corrected for tubing loss. | Set: Get Vent Settings Used: Assisting and Controlled Vent |
| $VT_{goal}$ | Tidal volume goal. Desired tidal volume | Controlled and Assisting Mode Ventilation, VT Trials, Set Vent. |
| $VT_{uncorr\ insp}$ | Tidal volume uncorrected. Actual measure of inspired tidal volume | Set: Get Vent Settings Used: Cont and Asst Ventilation VT Trials, Set Vent. |
| $VT_{uncorr\ insp\ goal}$ | Tidal volume uncorrected goal. Tidal volume goal before tubing compression factor is added | Get Vent Settings, Set Ventilator |
| $[H^+]_{backup}$ | $H^+$ concentration required to achieve the pH goal (7.30) if the patient stops assisting the ventilator | |
| $[H^+]_{goal}$ | $H^+$ concentration to obtain the $pH_a$ goal | Controlled and Assisting Mode Ventilation, Increase VT Trials - Controlled |
| $\Delta_2$ | Delta two. $SpO_{2\ abg}$ – $SaO_2$ difference between the last SaO2 and its associated SpO2. | SpO2 logic. |

The main protocol menu from which protocols are selected is shown in FIG 1B. This menu is typically accessed from a general menu which lists the various types of software which may be run from the bedside computer terminal. Both the main menu and the protocol menu options may be presented in a variety of manners, and the practice of the invention is not limited to a particular type of menu. For example, pull-down menus, icons, and text menus are equally suitable; the best choice of menu may depend on the particular operating system being used. It is also possible that rather than using a single menu, the menu options may be organized into several sub-menus. Any organization and presentation of the menu options may be used providing the required menu options are presented. The options presented by the main protocol menu are illustrated in the example of the preferred embodiment of the invention shown in FIG. 1B. They are:

1. Review protocol instructions. By selecting this option, the clinician is able to review a list of the instructions generated by the protocols during the past N hours, where N is selected by the clinician.
2. Review current status of patient. A summary of the current oxygenation, respiratory care and barotrauma status of the patient is presented, as well as the time at which the most recent data were charted and the most recent instruction generated by the protocol.
3. Give reasons for not following instructions. If an instruction generated by the protocol is not followed, the clinician is to record a reason for not following the instruction, for the purpose of tracking the reasoning between the delivered patient care. This option allows such a reason to be entered.
4. Give reasons for non-protocol CPAP termination. If a patient is taken off CPAP when there was no CPAP failure (as defined by the protocol), the clinician is to enter the reason for the termination of CPAP.
5. Suspend protocols. This option allows the protocol operation to be temporarily suspended during events or procedures which are not appropriately managed by the protocols (e.g. various tests, ICU procedures, transport of the patient, transient problems with equipment, etc.).
6. End protocol suspension. This option is used to end suspension of protocols, while allowing the clinician to select whether changes to patient data which occurred during the suspension should be ignored or not.
7. Update patient's barotrauma status. The patient's barotrauma status is updated when the patient is first put under protocol management, and subsequently only if there is a change in the patient's barotrauma status.
8. Run protocols based on oxygen classification. The protocols are run and a new instruction is generated following entry of oxygenation status determined from pulse oximeter measurements.
9. Run protocols base on most recent ABG. The protocols are run and a new instruction is generated using the most recently entered ABG (even though the time elapsed since entry of the ABG is such that normally no instruction would be generated). This option can be used to force the computer to generate an instruction.
10. Enter patient in the protocols. This option is used to identify a patient as being managed by computerized protocols. This must be done before the computer will generate any instructions for the patient.
11. Take patient out of the protocols. This option is selected if the patient is to be removed from the protocols permanently (e.g. because the patient has been extubated) or if the protocols are to be suspended for a period of more than 24 hours.
12. Exit. This option is selected after the protocols have been configured and are running. The computer returns to the general menu so that other software may be used, while the protocols run in background mode and generate instructions.

In the example of the preferred embodiment of the protocol menu shown in FIG. 1B, a message stating the current ventilatory care status of the patient is displayed, in this case "Patient is being supported with traditional therapy".

Preview

PROVIEW is the highest level logic set. It serves to coordinate and direct overall protocol execution sequences.

Figure 2:
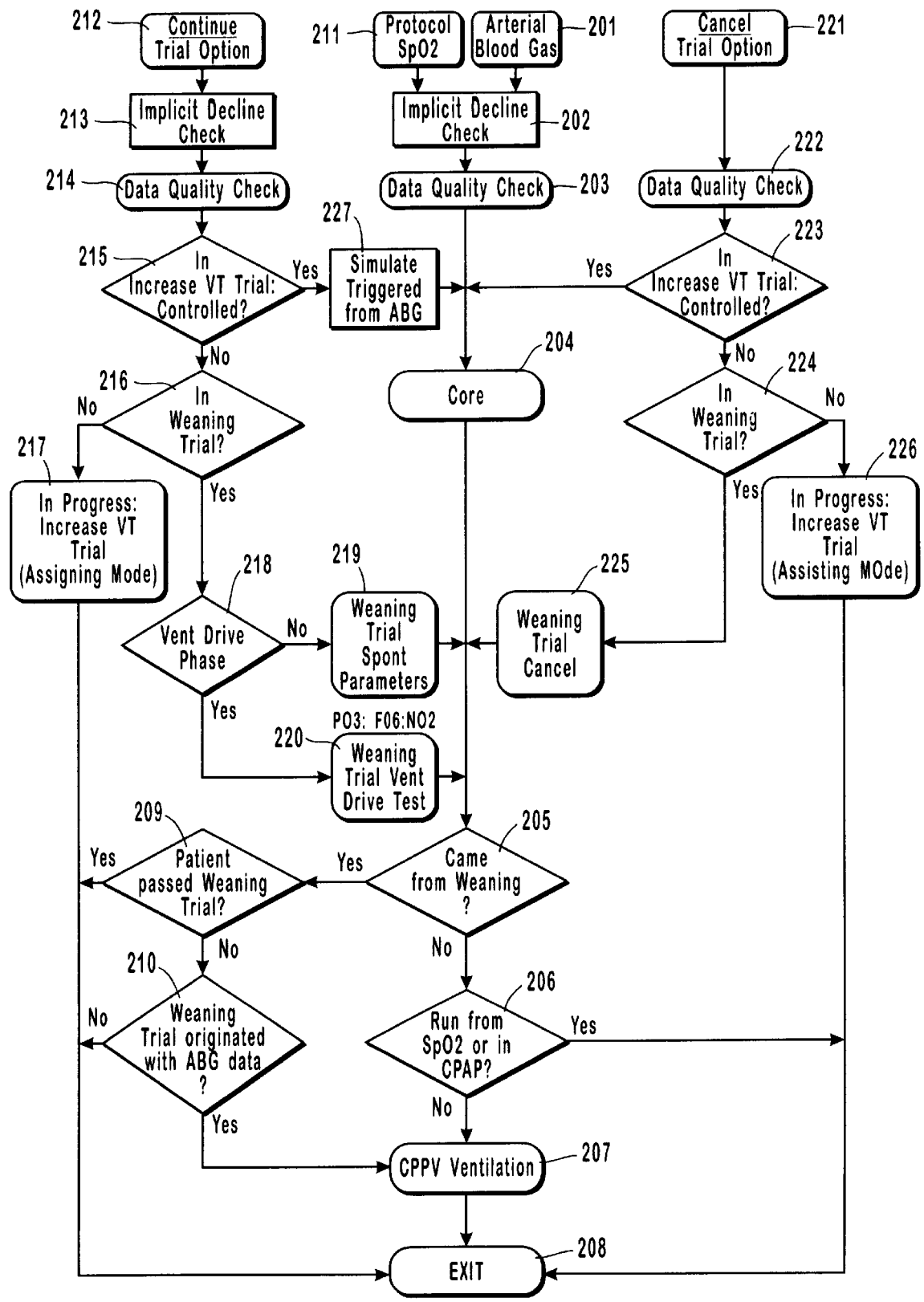
FIG. 2 is a flowchart diagram of the protocol overview (PROVIEW) routine.

A flow diagram of this routine is presented in FIG. 2. Once the protocols have been enabled from the main menu, PROVIEW is entered from one of several points. PROVIEW is most commonly called in response to the entry of data into the patient database. In this case, entry into PROVIEW occurs in background mode without user input. When a patient is initially assigned to management according to the protocols, the protocols are enabled but not immediately run; the first run through the protocols is initiated when patient ABG data is entered into the patient database. In this case, PROVIEW is entered at step 201. PROVIEW is also entered in background mode at step 212 and 221 when an increase VT trial or weaning trial is being performed and the Continue Trial or Cancel Trial option, respectively, is selected.

PROVIEW may be manually started (rather than started automatically in background mode operation) from two different menu selections: "Run protocols based on oxygen classification" (entry at step 211) and "Run protocols based on most recent ABG" (entry at step 201). The Oxygen classification option is selected when an oxygen classification based on pulse oximeter data has been added to the data base. The "Run Protocols Based on Most Recent ABG" option is generally used only when an item of data has been entered incorrectly and it is necessary to compute a new instruction after the correction of an erroneous clinical data base by entry of correct data.

When PROVIEW is entered at step 201, 211 or 212, the first action performed is an Implicit Decline Check (called from step 202 or 213) in which a query is generated regarding whether past instructions have been carried out, by comparing appropriate variables in the clinical data base before and after the generation of each instruction in question and by comparing the associated time intervals with the time allowed for execution of each instruction. Failure to satisfy requirements results in the conclusion that the clinician has "implicitly" declined the previous instruction by failing to carry it out before the protocols are run again. Immediately following the Implicit Decline check, a Data Quality Check (step 203 or 214) is carried out. When PROVIEW is entered at step 221, a data quality check is performed directly, at step 222.

Which protocol is entered from PROVIEW following the Data Quality Check depends upon how PROVIEW was entered and upon the current patient data values and ventilator settings. The possibilities are CORE (called from step 204), In Progress: Increase VT Trial (Assisting Mode) (called from step 226 or step 217), Weaning Trial—Spontaneous Parameters (called from step 219), Weaning Trial—Vent Drive Test (called from step 220), or Weaning Trial Cancel (called from step 225). If PROVIEW was entered from the Arterial Blood Gas or Protocol SpO$_2$ entry points (steps 201 and 211, respectively), immediately following the Data Quality Check, CORE is entered from step 204.

Data Quality Check

Figure 3:
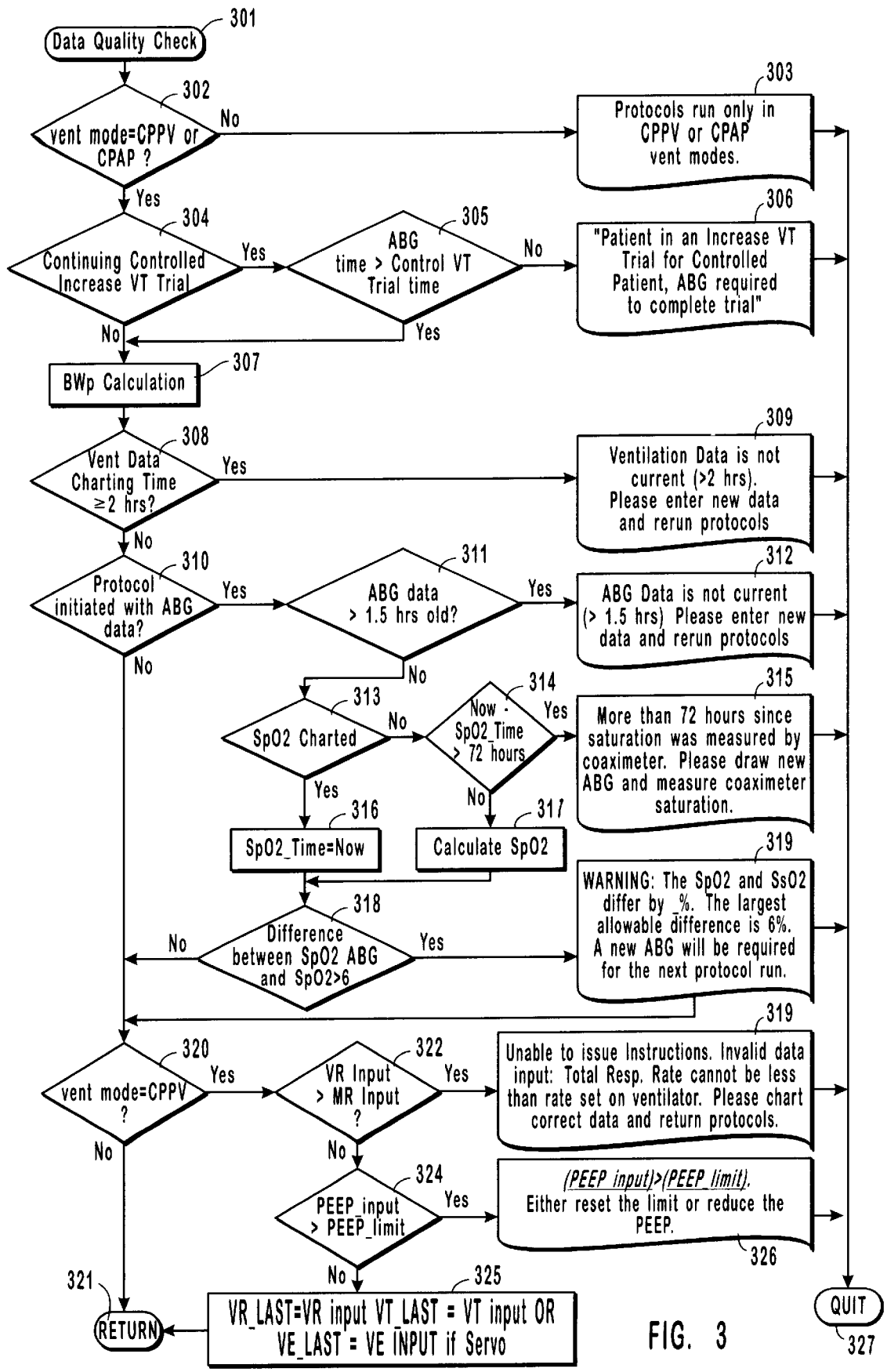
FIG. 3 is a flowchart diagram of the data quality check protocol.

The Data Quality Check logic is shown in FIG. 3; in this protocol data are checked for consistency and currentness which are required for the data to be sufficient for use as a basis for making patient treatment decisions. The data quality check protocol is entered at step 301. First a check is made whether the ventilation mode is CPAP or CPPV (step 302). If neither of these ventilation modes is being used, the protocols cannot be run; a message to this effect is generated (step 303) and the program quits protocol execution (step 327). If the vent mode is either CPPV or CPAP, and if a controlled (patient mode) increase VT trial is currently being continued (step 304), ABG time is compared to the controlled VT trial time (step 305). If ABG time is not greater, a message is generated stating that the patient is in a trial and that an ABG is required to complete it (step 306) and the 327 Data Quality Check protocol is exited at step 327. If ABC time is greater than Control VT Trial time (step 305), or if a controlled increase VT Trial was not being continued (step 304), BW$_p$ is calculated at step 307. BW$_p$, the predicted body weight of the patient is calculated, here and elsewhere, on the basis of the patient's age, height and gender. If the vent data were charted two or more hours ago (step 308), a message is generated which instructs that the data are too old and new data must be charted and the protocols be rerun (step 309), and the program quits protocol execution (step 327).

If Vent Data Charting Time is less than two hours (step 308), at step 310 a check is made as to whether the protocol was initiated with ABG data. If not, step 320 is executed next. If it was, but the ABC data is more than 1.5 hours old (step 311) a message is generated instructing that this ABC is too old and a new ABC should be drawn and the protocols rerun (step 312). If the ABG data is not more than 1.5 hours old, and if SaO$_2$ has been charted (step 316), the difference between SpO$_2$ abg (the arterial oxygen saturation determined with a pulse oximeter the same time as ABC was drawn) and SaO$_2$ (as determined from the ABC) is determined. If it is greater than 6% (step 318) a warning is generated which states that the largest allowable difference is 6%, and that a new ABC will be required for the next protocol run (step 319). If SaO$_2$ was not charted (step 314), and if more than 72 hours have passed since saturation was measured by cooximeter (step 314), a message is generated requesting that a new ABG be drawn and cooximeter saturation be measured (step 315). If no more than 72 hours have passed since cooximeter saturation was measured (step 314) a new SaO$_2$ value is calculated (step 317). Step 318 is then executed.

If vent mode is CPPV (step 320) and if VR$_{input}$ is greater than MR$_{input}$ (step 322) a message is generated which states that instructions cannot be generated because these values are not possible and the data must be invalid, and instructs the clinician to chart correct data and restart the protocols (step 323). The protocol then quits (step 327). If VR$_{input}$ is less than or equal to MR$_{input}$ (step 322), PEEP$_{input}$ is compared to PEEP$_{limit}$ (step 324). If PEEP$_{input}$ is greater, a message is generated stating that PEEP must be reduced or the limit must be reset (step 326). The protocol is then quit (step 327). If PEEP$_{input}$ is not greater than PEEP$_{limit}$, VR_LAST and VT_LAST are set to the current input values for VR and VT, or, if a servo ventilator is being used, VE_LAST is set to VE$_{Input}$ (step 325) and program control returns to PROVIEW from step 321.

Core

Figure 4:
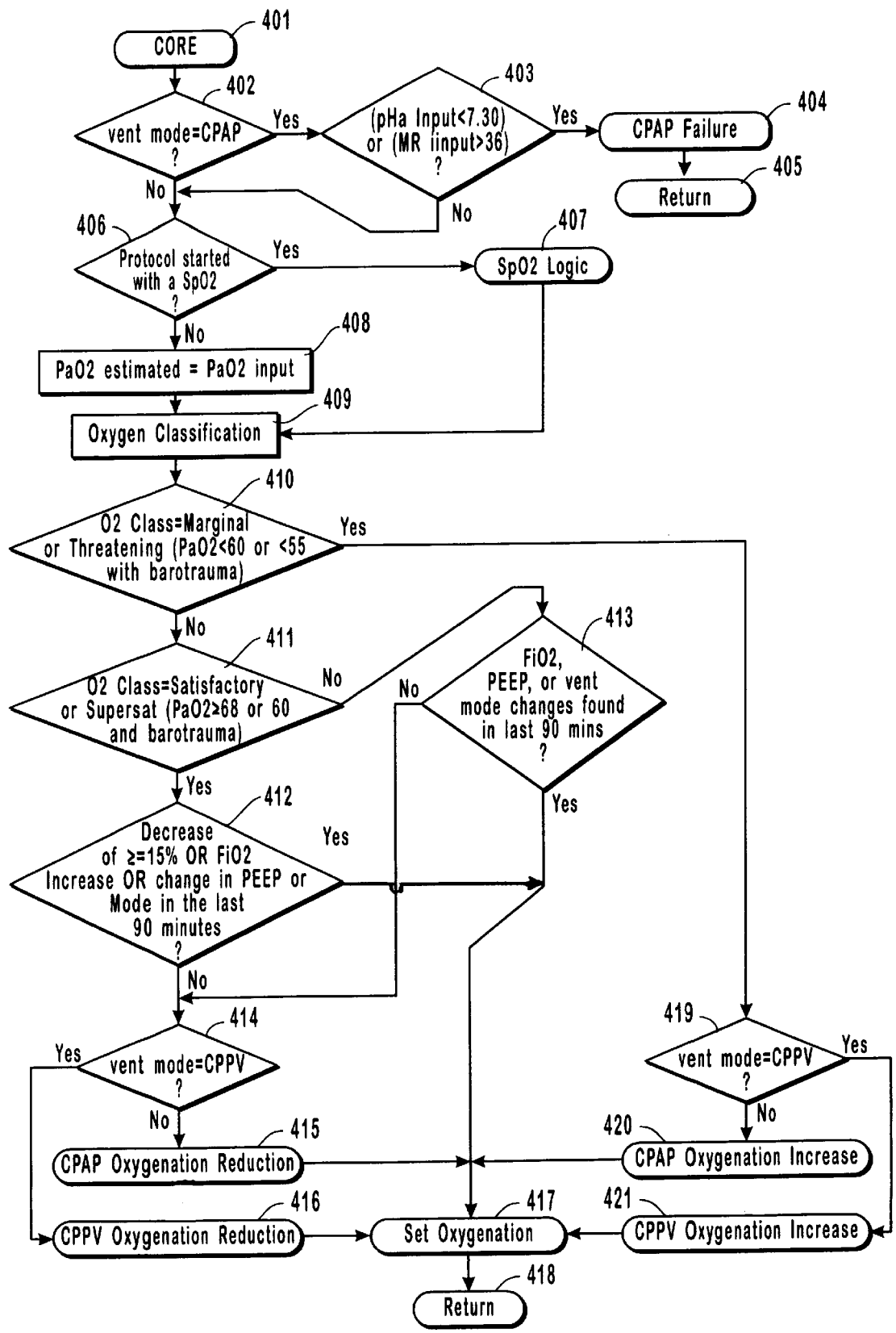
FIG. 4 is a flowchart diagram of the continuous respiratory evaluation (CORE) protocol.
Figure 5:
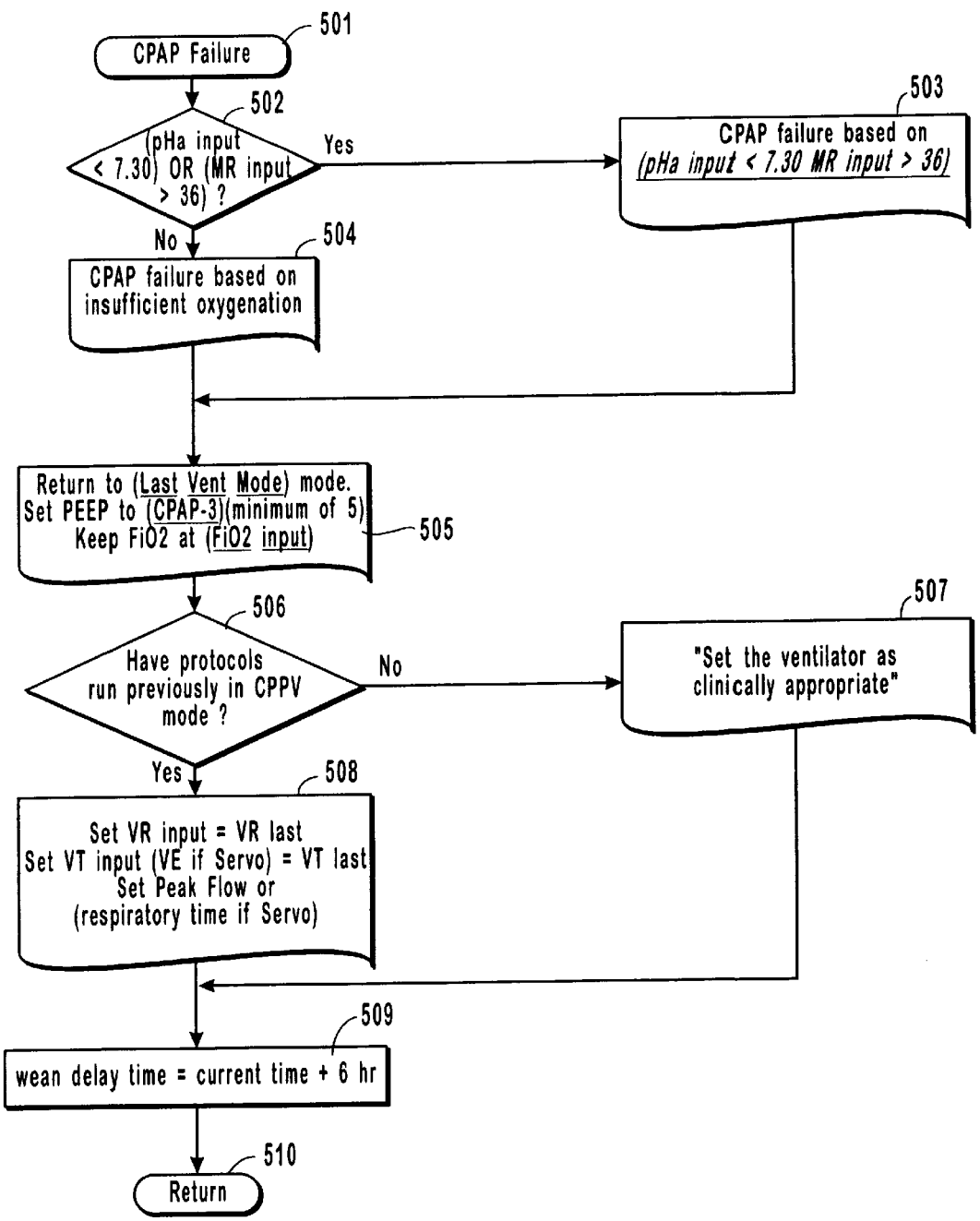
FIG. 5 is a flowchart diagram of the CPAP failure protocol.

The CORE protocol, shown in FIG. 4, is always entered at step 401. From CORE, all routines having to do with the regulation of arterial oxygenation are entered. The parameters of mechanical ventilation which are adjusted to maintain arterial oxygen partial pressure are F$_I$O$_2$, PEEP, and mode. The main tasks performed in CORE are making an oxygen classification according to the rules in Table 3, and selecting an appropriate increase or decrease in the adjusted parameters of mechanical ventilation, depending on oxygen classification and ventilation mode, according to the rules in Tables 4 and 5. If CPAP is in use (determined at step 402) and it is found that the blood pH is too low or the respiratory rate is too high (in step 403), CPAP is considered to have failed. If this is the case, at step 404 the CPAP Failure protocol shown in FIG. 5 is called.

CPAP Failure

The CPAP Failure protocol is entered at step 501. pH and MR are checked at step 502. If pH is too low, or MR is too high, a message is generated at step 503 stating that CPAP failure is based on pH and MR. Otherwise, a message is generated stating that CPAP failure was based on insufficient oxygenation (step 504). The clinician is instructed to return the patient to the last vent mode and to adjust PEEP and $F_IO_2$ (step 505). If, at step 506, it is determined that the protocols have previously been run in CPPV mode, an instruction is generated to set VR, VT and Peak Flow to their prior settings (step 508). If not, the clinician is instructed to set the ventilator as clinically appropriate (step 507). The wean delay time is then set (step 509) to delay future weaning attempts, and program control returns to CORE from step 510, and from CORE to PROVIEW (step 405).

$S_pO_2$ Logic

Figure 6:
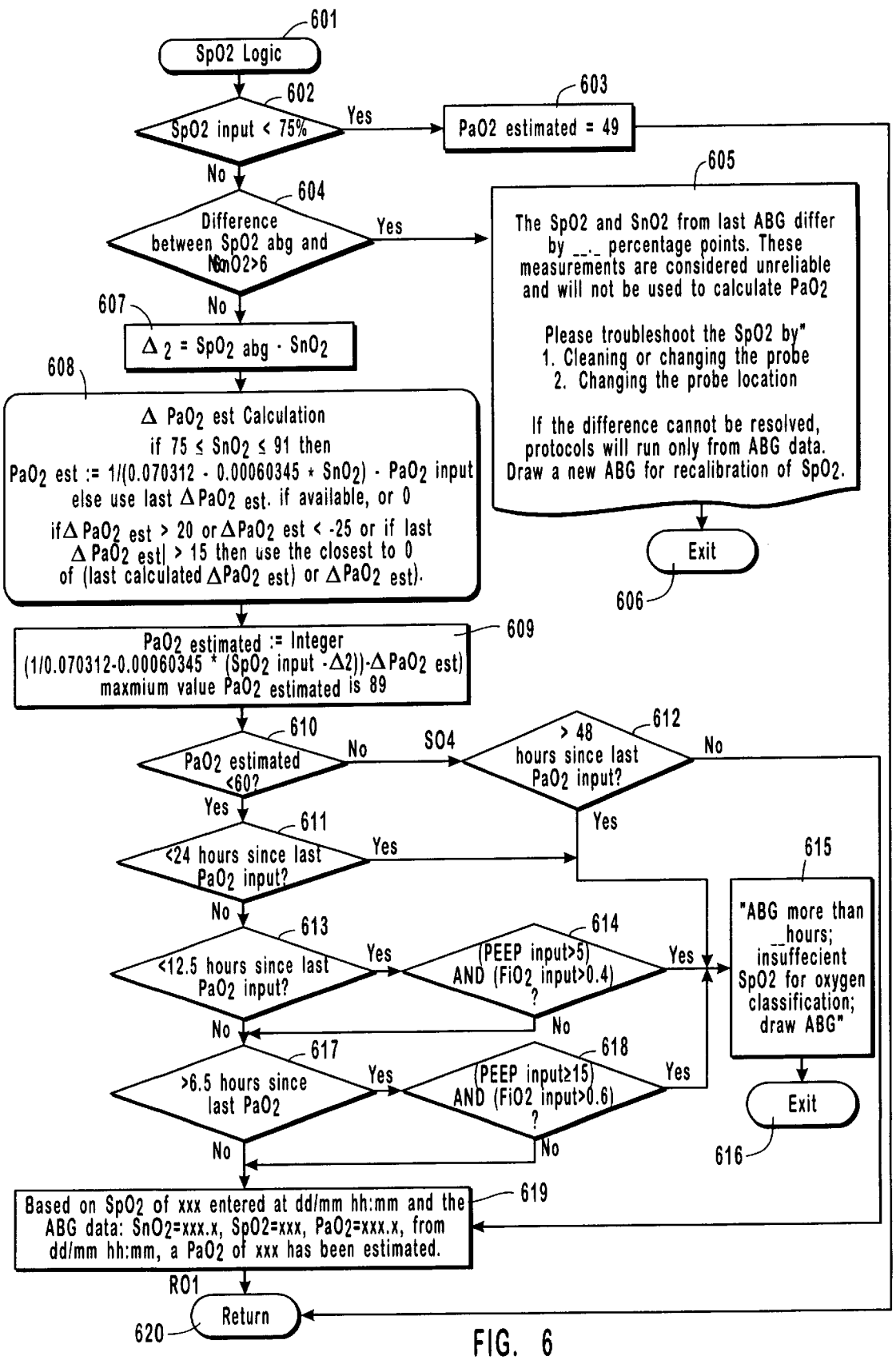
FIG. 6 is a flowchart diagram of the $SpO_2$ logic ($SpO_2$-based $PaO_2$ estimation) protocol.

In step 406 of CORE it is determined whether PROVIEW, and subsequently CORE were entered from the "Run protocols based on $SpO_2$ classification" menu option. If so, CORE calls (from step 407) the $SpO_2$ logic shown in FIG. 6 to obtain an estimate of $PaO_2$. Otherwise, $PaO_2$ estimated simply is set to $PaO_2$ input (step 408). It is convenient and non-invasive to measure the amount of oxygen in the arterial blood using pulse oximetry ($SpO_2$). The protocols are driven by oxyenation classifications based on the arterial partial pressure of oxygen ($PaO_2$). The purpose of the $SpO_2$ protocol is to produce the same oxygenation classifications without the need for drawing an arterial blood sample. This is done by comparing an $SpO_2$, $SaO_2$ and $PaO_2$ measured simultaneously at least once every 2 days. $SpO_2$ is related to $SaO_2$; however, there are many other factors that influence this relationship (blood flow to the measurement site, skin color, skin thickness, etc). The difference between $SpO_2$ and $SaO_2$ is termed $\Delta_2$ and is measured in % saturation. The $SaO_2$ is related to the $PaO_2$ by a curve, the oxyhemoglobin dissociation curve. The curve is sigmoidal in shape with a knee above 90%. The higher the $PaO_2$, the higher the $SaO_2$ and vice-versa. The curve tangentially approaches 100% as $PaO_2$ approaches 600–700 mm Hg. The $SaO_2$ is above 99% when the $PaO_2>200$ mm Hg. In this region the curve can be represented in the form: $PaO_2=1/(a-b*SaO_2)$ where $a=0.070312$ and $b=0.00060345$ for a "normal" curve. This curve is not static, but moves to the left or right (higher or lower $PaO_2$ for the same $SaO_2$) depending on the body temperature and pH. The amount of right or left shift is called $\Delta PaO_2$ estimated ($\Delta PaO_2$ est, measured in mm Hg). The $\Delta_2$ and $\Delta PaO_2$ est are calculated and stored for future use. From this point on, when an $SpO_2$ is entered it is corrected to a predicted $SaO_2$ by subtracting $\Delta_2$. This predicted $SaO_2$ is then put into the simple equation for a normal curve and a $PaO_2$ estimate assuming a normal curve is calculated. This $PaO_2$ estimate is then shifted by $\Delta PaO_2$ est to account for the actual shifted curve.

The $SpO_2$ Logic Protocol is entered at step 601. If $SpO_2$ is less than a specified value which indicates threatened hypoxemia (e.g. 75%) (step 602), $PaO_2$ is assigned a predetermined value in the hypoxemia range (step 603). If $SpO_2$ is not threateningly low, the difference between $SpO_2$ abg and $SaO_2$ is determined. If it is greater than 6 (step 604) a message is generated indicating that $SpO_2$ may not be reliable (step 605), and program control returns to CORE from step 606. If the difference is not larger than 6, it is assigned to the variable $\Delta_2$ (step 607) and $\Delta PaO_2$ is calculated as follows: if $SaO_2$ is between 75 and 91 then $\Delta PaO_{2est}$ is calculated as $(1/(0.070312-0.00060345*SaO_2)-PaO_2$ input. If $SaO_2$ is not within this range, it is not possible to determine the shift in the oxyhemoglobin dissociation curve and $\Delta PaO_{2est}$ is assigned the most recent $\Delta PaO_{2est}$ value, if available, or 0 otherwise. If the magnitude of $\Delta PaO_{2est}$ is large (>20 or <-25) or $PaO_{2est}$ differs significantly from the previous $\Delta PaO_{2est}$ whichever of the current and previous $\Delta PaO_{2est}$ is closer to zero is used (step 608). $PaO_{2est}$ is then calculated as Integer $(1/(0.070312-0.00060345*(SpO_2$ input$-\Delta_2))-\Delta PaO_{2est})$ (step 609). If $PaO_{2est}$ is less than 60, as determined in step 610, and it has been more than 24 hours since the last $PaO_2$ input (step 611) a message is generated stating that $SpO_2$ is insufficient for oxygen classification and that a new ABG should be drawn (step 615). Program control then exits the $SpO_2$ logic protocol and returns to CORE (step 616). If $PaO_{2est}$ is not less than 60, and it has been more than 48 hours since the last $PaO_2$ input (step 612), the message of step 615 is generated. If it has not been more than 48 hours since the last $PaO_2$ input was made, a message is generated stating the new estimated $PaO_2$ (step 619). If it has been less than 24 hours, but more than 12.5 hours since the last $PaO_2$ input (step 613), if $PEEP_{input}$ is greater than 5 and $F_IO_2$ input is greater than 0.4 (step 614), or if greater than 6.5 hours have passed since the last $PaO_2$ input (step 617) and the $PEEP_{input}$ is greater than or equal to 15 and $F_IO_2$ input is greater than 0.6, (step 618), a message advising that a new ABG be drawn is generated (step 615) and the $SpO_2$ logic protocol is exited (step 616). Otherwise, a message showing a new estimated $PaO_2$ value is displayed (step 619) and program control returns to CORE (step 620).

Oxygenation Status

Once an estimation of PaO2 has been made, the patient's oxygenation status (i.e., the $PaO_2$ level) is classified (step 409 in CORE, FIG. 4). The Oxygenation is classified into one of five categories: Threatening, Marginal, Acceptable, Satisfactory, or Super-satisfactory. Rules for oxygenation classification take into account the presence or absence of barotrauma. The $PaO_2$ ranges used in oxygenation classification in the present example are shown in Table 3. It will be appreciated that the particular classification levels presented here are intended as examples consistent with accepted medical practice and variations of said values consistent with accepted medical practice fall within the scope of the invention.

TABLE 3

Oxygen Classification

| $O_2$ Class | Barotrauma | Nonbarotrauma |
|---|---|---|
| Threatening | $PaO_2 < 50$ | $PaO_2 < 50$ |
| Marginal | $50 <= PaO_2 < 55$ | $50 <= PaO_2 < 60$ |
| Acceptable | $55 <= PaO_2 < 60$ | $60 <= PaO_2 < 68$ |
| Satisfactory | $60 <= PaO_2 < 110*$ | $68 <= PaO_2 < 110*$ |
| Super-satisfactory | $110* <= PaO_2$ | $110* <= PaO_2$ |

*The value of 110 mm Hg is used at sea level. At higher altitudes, we recommend the use of a lower value, for example 90 mm Hg at 5000 feet above sea level.

TABLE 4

Increase Oxygenation Therapy Sequence

| Barotrauma | Nonbarotrauma |
|---|---|
| (1) Increase FIO2 to 0.8 | (1) Increase FIO2 to 0.6 |
| (0.2 increments if O2 class = threatening, otherwise 0.1 increments | |
| (2) Increase PEEP to 20 | (2) Increase PEEP to 20 |
| (2 cm H2O increments) | (5 cm H2O increments if Ppeak < 50) |
| (2 cm H2O increments if Ppeak $\geq$ 50) | |

TABLE 4-continued (3) Increase FIO2 to 1.0 (3) Increase FIO2 to 1.0
(0.2 increments if O2 class = threatening, otherwise 0.1 increments)
(4) Increase PEEP to 25 (4) Increase PEEP to 25*
    (2 cm H2O increments) (5 cm H2O increments if Ppeak < 50)
                                (2 cm H2O increments if Ppeak ≧ 50)

*The PEEP limit can be changed by performing a PEEP increase or decrease trial (this protocol is available on paper) as long as the patient fits the implementation rules. If PEEP limits are redefined by a PEEP trial, these new limits can be entered into the computer and the protocol will operate using the redefined maximum therapy limits.

TABLE 5

Decrease Therapy Sequence

| Barotrauma | Nonbarotrauma |
|---|---|
| (1) Decrease FIO2 to 0.7 | (1) Decrease FIO2 to 0.5 |
| (0.1 decrements for barotrauma or nonbarotrauma) | |
| (2) Decrease PEEP to 14 | (2) Decrease PEEP to 14 |
| (1 cm H2O decrements) | |
| (3) Decrease FIO2 to 0.4 | (3) Decrease FIO2 to 0.4 |
| (0.1 decrements for barotrauma or nonbarotrauma) | |
| (4) Decrease PEEP to 5 | (4) Decrease PEEP to 5 |
| (1 cm H2O decrements) | |
| (5) Decrease FIO2 to 0.3 if the PaO2 is above 110* | (5) Decrease FIO2 to 0.3 if the PaO2 is above 110* |
| (0.1 decrements for barotrauma or nonbarotrauma) | |

(*110 mm Hg is used at sea level, 90 mm Hg is used at elevations greater than 4000 feet elevation)

Oxygenation Increase

Figure 7:
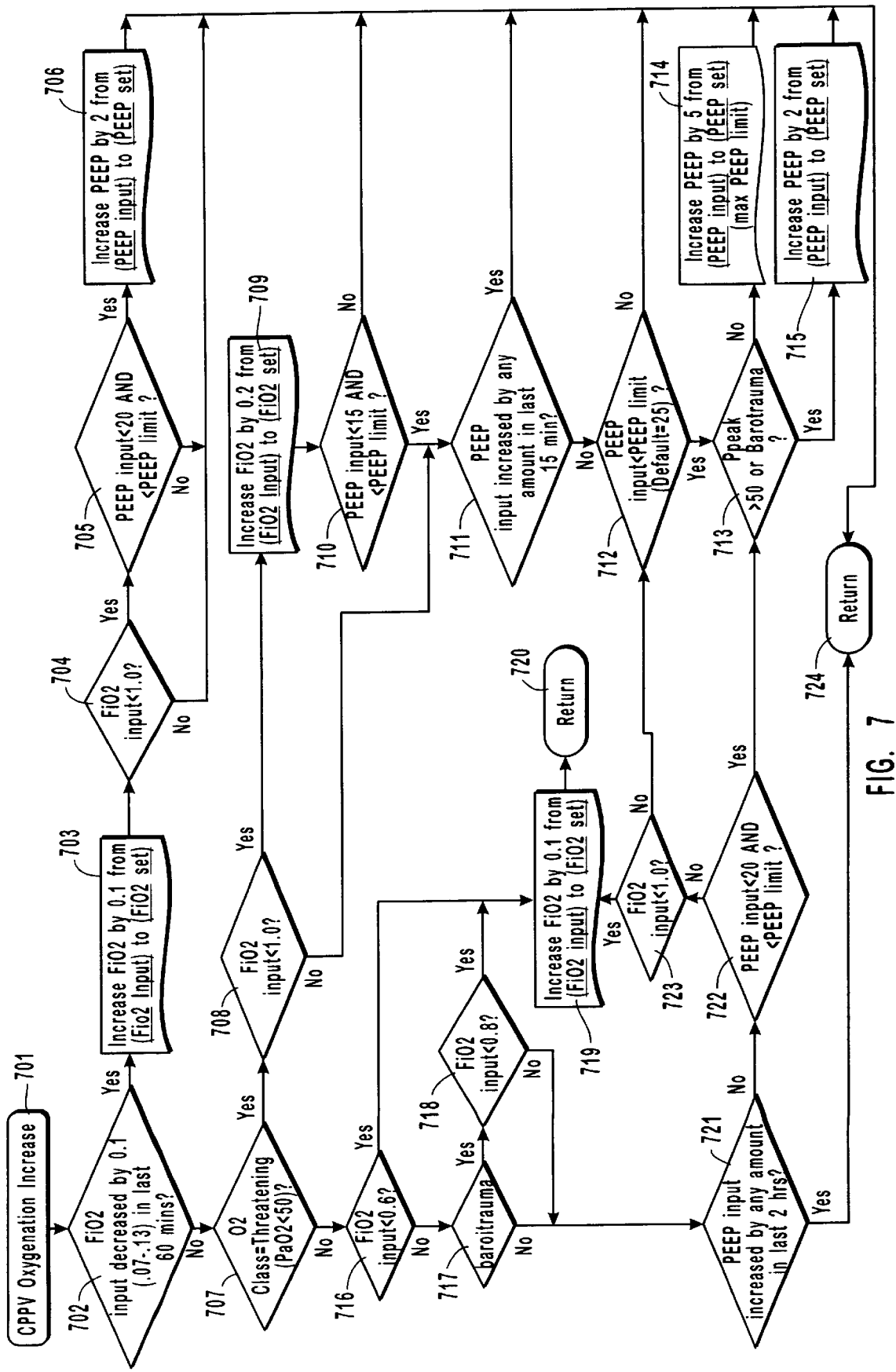
FIG. 7 is a flowchart diagram of the CPPV (continuous positive pressure ventilation) oxygenation increase protocol.

If $PaO_2$ is too low (oxygenation class is threatening or marginal), as determined in step 410, oxygenation is increased. The method used to increase oxygenation depends on the ventilation mode being used. If CPPV ventilation is used, (determine in step 419), the CPPV Oxygenation Increase protocol is activated (step 421). If not, the CPAP Oxygenation Increase protocol is activated (step 420). The basic principles for increasing oxygenation, applicable to both CPPV and CPAP, are shown in table 4. An important feature of the oxygenation increase sequence is that PEEP and $F_IO_2$ are increased alternately, i.e. with one adjusted. The CPPV Oxygenation Increase protocol, shown in FIG. 7, generates instructions for increasing either PEEP or $F_IO_2$, according to the logic shown in tables 6,7, and 8 below.

CPPV Oxygenation Increase

The CPPV Oxygenation Increase Protocol is entered at step 701.

If the $F_IO_2$ input was decreased by 0.1 within the last 60 minutes (step 702) a message is generated to "undo" this reduction by instructing that $F_IO_2$ be increased by 0.1 (step 703). If $F_IO_2$ input is not greater than 0.6 (step 704) program control returns to CORE from step 724. If $F_IO_2$ input is greater than 0.6 (step 704), and if $PEEP_{input}$ is less than 15 and less than the $PEEP_{limit}$ (step 705), a message is generated instructing that PEEP be increased by 2 (step 706). Program control then returns to CORE (step 724).

If $F_IO_2$ input was not decreased by 0.1 within the last 60 minutes (step 702), if the $O_2$ class is threatening (step 707), therapy is increased rapidly and aggressively. If $F_IO_2$ input is less than 1.0 (step 708), a message is generated instructing that $F_IO_2$ be increased by 0.2 (step 709). Following step 709, if $PEEP_{input}$ is not less than 15 and not less than the $PEEP_{limit}$ (step 710), program control returns to CORE from step 724. If $F_IO_2$ input was not less than 1.0 at step 708, step 711 is executed. If $PEEP_{input}$ was not increased in the last 15 minutes (step 711), and $PEEP_{input}$ is less than $PEEP_{limit}$ (step 712), if $P_{peak}$ is greater than or equal to 50 or barotrauma is present (step 713), a message is generated instructing for a conservative increase in PEEP by 2 (step 715). If $P_{peak}$ is less than 50 and no barotrauma is present (step 713), a message is generated instructing that PEEP be increased by 5 (step 714).

If at step 707, $O_2$ Class is not found to be threatening (marginal), if $F_IO_2$ input is less than 0.6 (step 716) a message is generated instructing that $F_IO_2$ be increased by 0.1 (step 719). If $F_IO_2$ input is not less than 0.6 (step 716), but barotrauma is present (step 717) and $F_IO_2$ input is less than 0.8 (step 718), step 719 is also carried out. Following step 719, program control returns to CORE from step 720. If no barotrauma was present at step 717, or $F_IO_2$ input was not less than 0.8 at step 718, a check is made for an increase in $PEEP_{input}$ within the last two hours, (step 721). If there was an increase in PEEP, program control returns to CORE from step 724. If $PEEP_{input}$ was not increased within the past two hours (step 721), and if $PEEP_{input}$ is less than 20 and less than $PEEP_{limit}$ (step 222), step 713 is executed. If $P_{peak}$ is greater than or equal to 50, or barotrauma is present (step 713) a more conservative increase of 2 is advised (step 715). Otherwise, an increase of 5 is advised (step 714). If $PEEP_{input}$ is not less than 20, and less than the $PEEP_{limit}$ (step 222), if $F_IO_2$ input is less than 1.0 (step 723), a message is generated instructing that $F_IO_2$ be increased by 0.1 (step 719). Program control then returns to CORE (step 720). If at step 723, $F_IO_2$ input is not less than 1.0, program control goes to step 712, and step 712 and steps subsequent to it are carried out as described above, and program control eventually returns to CORE from step 724.

TABLE 6

PEEP risk/benefit ratio classifications inherent in CPPV Protocols

| PEEP Risk/Benefit Classification | Acceptable, Satisfactory or Super Satisfactory Arterial Oxygenation | Marginal or Threatening Arterial Hypoxemia |
|---|---|---|
| High | PEEP > 15 | |
| Moderate | 5 < PEEP ≦ 15 | PEEP > 20 |
| Low | PEEP ≦ 5 | 15 < PEEP ≦ 20<br>PEEP ≦ 15 |

TABLE 7

$F_IO_2$ risk/benefit ratio classifications inherent in CPPV Protocols

| $F_IO_2$ Risk/Benefit Classification | Acceptable, Satisfactory or Super Satisfactory Arterial Oxygenation | | Marginal or Threatening Arterial Hypoxemia | |
|---|---|---|---|---|
| | Barotrauma | Nonbarotrauma | Barotrauma | Nonbarotrauma |
| High | $F_IO_2 > 0.7$ | $F_IO_2 > 0.5$ | | |
| Moderate | $0.4 < F_IO_2 \leq 0.7$ | $0.4 < F_IO_2 \leq 0.5$ | $F_IO_2 \geq 0.8$ | $F_IO_2 \geq 0.6$ |
| Low | $F_IO_2 \leq 0.4$ | $F_IO_2 \leq 0.4$ | $F_IO_2 < 0.8$ | $F_IO_2 < 0.6$ |

TABLE 8

Size and Timing of $F_IO_2$ and PEEP

| Arterial oxygenation Classification | Size of Change | | | | Time Between Changes | |
|---|---|---|---|---|---|---|
| | Barotrauma | | Nonbarotrauma | | | |
| | $F_IO_2$ | PEEP | $F_IO_2$ | PEEP | $F_IO_2$ | PEEP |
| Threatening Hypoxemia (Increase Therapy) | 0.2 | 2 | 0.2 | 5 | As quickly as possible | 15 min |
| Marginal Hypoxemia (Increase Therapy) | 0.1 | 2 | 0.1 | 5 | As quickly as possible | 2 Hrs |
| Acceptable (Reduce Therapy) | 0.1 | 1 | 0.1 | 1 | 2 Hrs | 2 Hrs |
| Satisfactory (Reduce Therapy) | 0.1 | 1 | 0.1 | 1 | 2 rapid* decreases then 2 Hrs | 2 Hrs |
| Super Satisfactory (Reduce Therapy) | 0.2 | 2 | 0.2 | 2 | 2 rapid* decreases then 2 Hrs | 2 Hrs |

*"rapid" means as quickly as possible with a check of oxygenation revealing satisfactory or super-satisfactory oxygenation after the first decrease.

CPAP Oxygenation Increase

Figure 8:
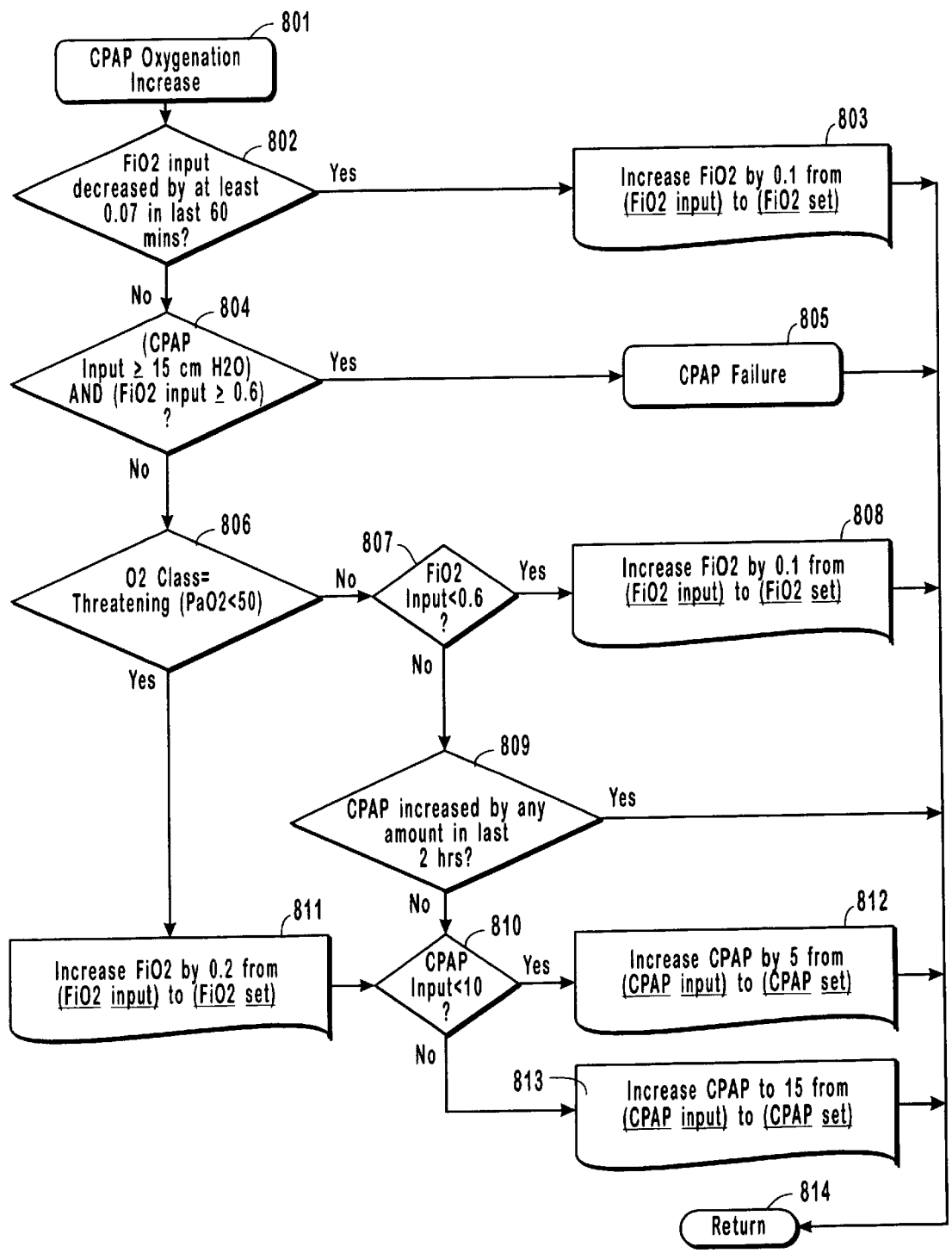
FIG. 8 is a flowchart diagram of the CPAP (continuous positive airway pressure) oxygenation increase protocol.
Figure 9A:
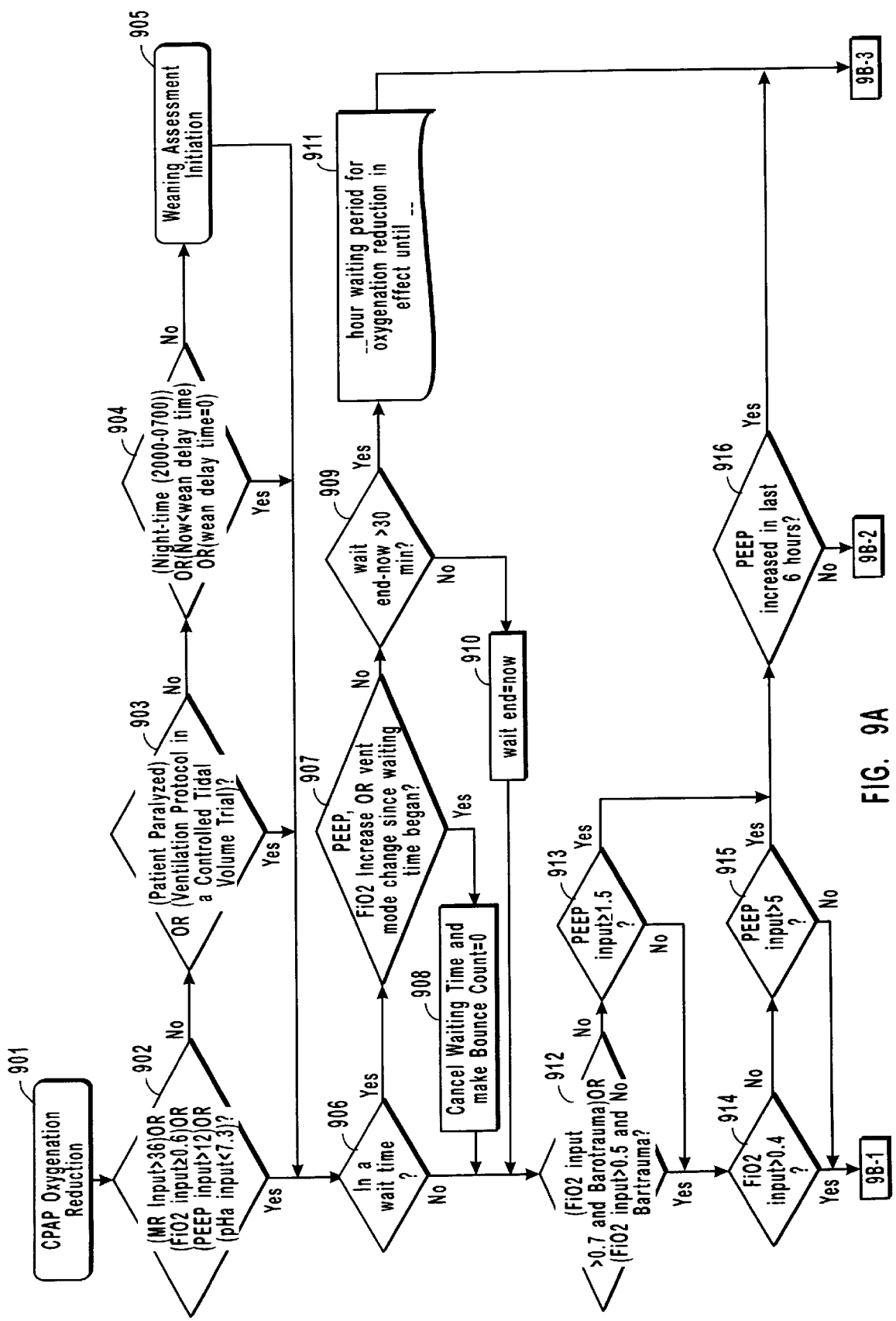
FIG. 9 is a flowchart diagram of the CPPV oxygenation reduction protocol.
Figure 9B:
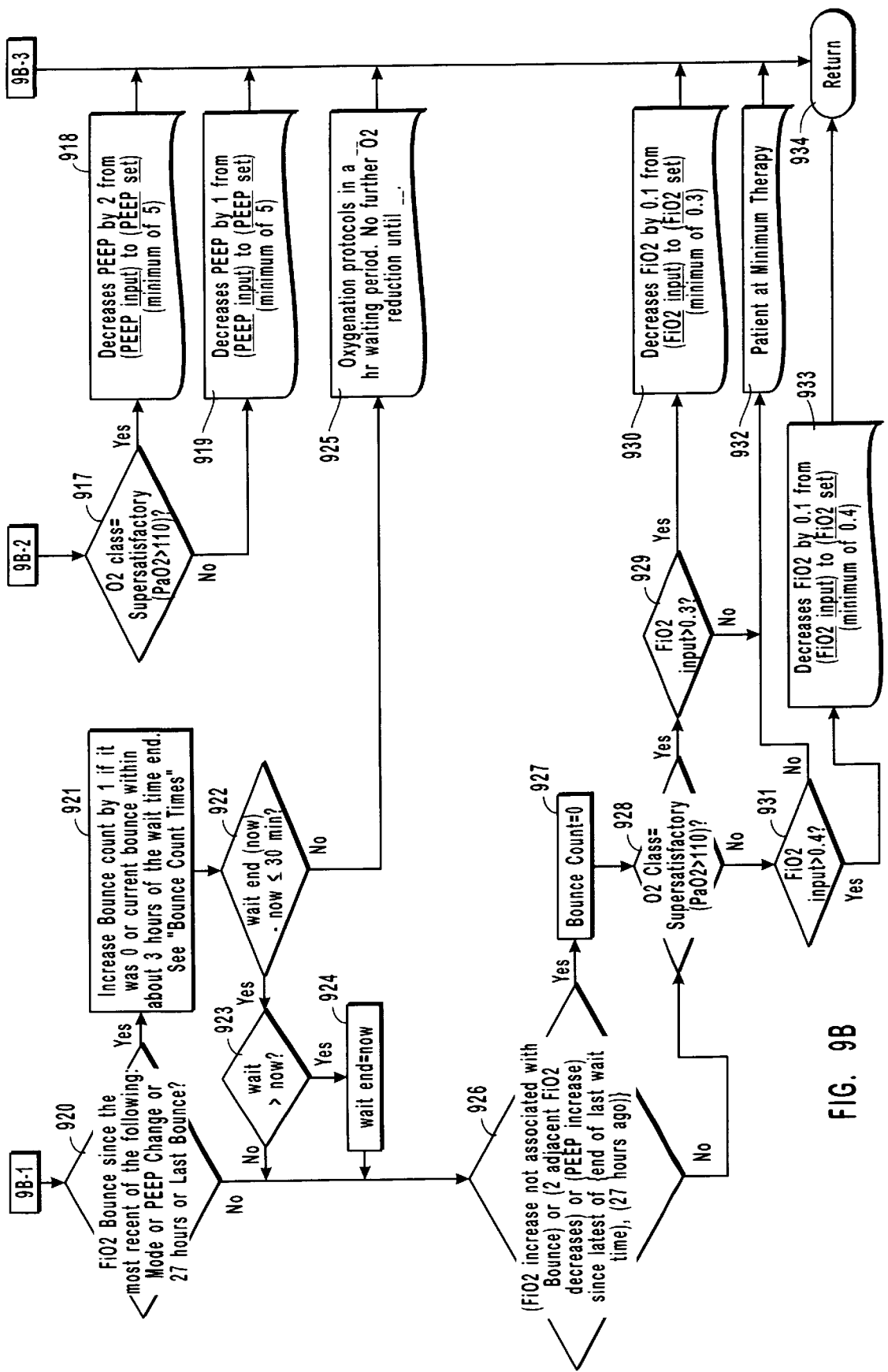

If, at step 419 of CORE, it is determined that CPAP ventilation is in use, the CPAP Oxygenation Increase protocol depicted in FIG. 8 is activated. This protocol determines the size and frequency of the changes in CPAP or $F_IO_2$. The rules used to determine the changes in CPAP and $F_IO_2$ in the CPAP Oxygenation Increase protocol are shown in tables 9, 10, and 11. The CPAP Oxygenation Increase protocol is entered at step 801. If $F_IO_2$ input was decreased by at least 0.07 in the last 60 minutes (step 802), a message is generated stating that $F_IO_2$ should be increased by 0.1 (step 803).

If $F_IO_2$ input was not decreased by at least 0.07 in the last 60 minutes, a check for CPAP failure is made. If CPAP input is greater than or equal to 15 cm $H_2O$ and $F_IO_2$ input is greater than or equal to 0.6 (step 804), the CPAP Failure protocol shown in FIG. 5 is called from step 805. If there is no CPAP failure, but $O_2$ class is threatening (step 806) an aggressive increase in $F_IO_2$ by 0.2 is instructed (step 811). Then, if CPAP input is less than or equal to 10 (step 810) a message is generated instructing that CPAP also be increased by 5 (step 812), or if CPAP input is not less than or equal to 10, a message is generated instructing that CPAP be increased by 15 (step 813). If the $O_2$ class is not threatening (marginal hypoxemia) (step 806) and if $F_IO_2$ input is less than 0.6 (step 807), a message is generated instructing that $F_IO_2$ be increased by 0.1 (step 808). If $F_IO_2$ input is not less than 0.6, and if CPAP was increased by any amount in the last two hours (step 809), program control returns to CORE from step 814. If CPAP was not increased in the last two hours, step 810, and then either step 812 or step 813 are executed. Following generation of a message in step 803, 808, 812 or 813, program control returns to CORE from step 814. After program control returns to CORE from either of the oxygenation increase protocols, a Set Oxygenation protocol (described subsequently) is called (step 417).

TABLE 9

CPAP risk/benefit ratio classifications inherent in the CPAP protocols

| CPAP Risk/Benefit Classification | CPAP Level |
|---|---|
| High (CPAP Failure, return to CPPV) | CPAP ≥ 15 |
| Moderate | 5 < CPAP < 15 |
| Low | CPAP ≤ 5 |

TABLE 10

$F_IO_2$ risk/benefit ratio classifications inherent in the CPAP protocols. When marginal or threatening arterial hypoxemia was present, higher $F_IO_2$ levels were accepted.

| $F_IO_2$ Risk/Benefit | Acceptable, Satisfactory or Super Satisfactory Arterial Oxygenation | Marginal or Threatening Arterial Hypoxemia |
|---|---|---|
| High | $F_IO_2 \geq 0.6$ | |
| Moderate | $0.4 \leq F_IO_2 < 0.6$ | $F_IO_2 \geq 0.6$ |
| Low | $F_IO_2 < 0.4$ | $F_IO_2 < 0.6$ |

TABLE 11

Therapy changes used in the CPAP protocols. Therapy was increased aggressively, but reduced slowly, both in terms of the size and frequency of therapy changes. $F_IO_2$ in %, CPAP in cm $H_2O$

| Arterial Oxygenation Classification | Size and Combination of Changes | | | Time Between Changes | |
|---|---|---|---|---|---|
| | $F_IO_2$ | | CPAP | $F_IO_2$ | CPAP |
| Threatening Hypoxemia (Increase Therapy) | 0.2 | AND | 5 | As quickly as possible | 15 min |
| Marginal Hypoxemia (Increase Therapy) | 0.1 | OR | 5 | As quickly as possible | 2 Hrs |
| Acceptable (Reduce Therapy) | 0.1 | OR | 1 | 2 Hrs | 2 Hrs* |
| Satisfactory (Reduce Therapy) | 0.1 | OR | 1 | 2 rapid decreases then 2 Hrs | 2 Hrs* |
| Super Satisfactory (Reduce Therapy) | 0.1 | OR | 1 | 2 rapid decreases then 2 Hrs | 2 Hrs* |

*No decrease in CPAP for 6 hours following a CPAP increase.

Acceptable Oxygenation—No Change in Therapy

If, at step 410 of CORE, $O_2$ class is acceptable (neither Marginal nor Threatening), step 411 is executed. If PaO2 is found to be sufficient (oxygenation class is satisfactory or super-satisfactory) at (step 411), and there was a decrease of greater than 15%, an $F_IO_2$ increase, or a change in PEEP or mode within the last 90 minutes (step 412) the Set Oxygenation protocol is called from step 417 without first changing oxygenation parameters. If $O_2$ class was neither satisfactory nor super-satisfactory (step 411) and $F_IO_2$, PEEP or vent mode were changed within the last 90 minutes (step 413), the Set Oxygenation Protocol (step 417) is called.

Oxygenation Reduction

If $O_2$ class is satisfactory or supersatisfactory (step 411), and there has not been a decrease of greater than or equal to 15% or an $F_IO_2$ increase, change in PEEP, or Mode in the last 90 minutes (step 412), if vent mode is CPPV (step 414), then the CPPV Oxygenation Reduction Protocol is called (step 416). If the mode is CPAP, the CPAP Oxygen Reduction Protocol is called (step 415). The basic approach for decreasing oxygenation is shown in table 5. This applies to both CPAP and CPPV. As with the oxygenation reduction strategy shown in table 4, adjustments are made alternately to $F_IO_2$ and PEEP.

CPPV Oxygenation Reduction

The CPPV Oxygenation Reduction Protocol is entered at step 901. A check is first made to determine whether $MR_{input}$ is greater than 36, $F_IO_2$ is greater than or equal to 0.6, $PEEP_{input}$ is greater than 12 or $pH_{a\ input}$ is less than 7.3 (step 902). If none of these are true, a check is made as to whether the patient is paralyzed or in a Controlled Tidal Volume Trial (step 903), or whether it is night time, or if there is a wean delay time in effect (step 904). If none of these conditions hold, weaning assessment is initiated (step 905). If any of the conditions of steps 903 or 904 were true, a wait time check is made (step 906). If a wait time is in effect, and if a PEEP or $F_IO_2$ increase or a vent made change have been made since the waiting time began (step 907), the waiting time is canceled (step 908) and "Bounce Count" is set to zero. If no change in PEEP, $F_IO_2$ or vent mode was mode since the wait time began (step 907), and the difference between the end of the wait time and the present time is less than 30 minutes (step 909), the wait time is ended (step 910). Otherwise, a message is generated indicating that a waiting period must be observed before oxygenation can be reduced (step 911).

If there is no wait time, or the wait time is canceled or ended, a check is made as to whether $F_IO_2$ input is greater than 0.7 and barotrauma is present, or whether $F_IO_2$ input is greater than 0.5 in the absence of barotrauma (step 912). If not, and $PEEP_{input}$ is greater than or equal to 15, (step 913), PEEP will be decreased, unless it was increased within the last 6 hours (step 916). If PEEP was not increased within the last 6 hours, and if $O_2$ Class is Super Satisfactory (step 917), a message is displayed instructing that PEEP be decreased by 2. (Step 918) If $O_2$ class is not SuperSatisfactory (step 917), an instruction is generated for decreasing PEEP by 1 (step 919). If, at step 912, $F_IO_2$ input is greater than 0.7 and barotrauma is present, or if $F_IO_2$ input is greater than 0.5 in the absence of barotrauma or if these conditions are false but $PEEP_{input}$ is less than 15 (step 913), a determination is made whether $F_IO_2$ input is greater than 0.4 (step 914). If it is not, and $PEEP_{input}$ is greater than 5 (step 915), and was not increased within the last 6 hours (step 916) PEEP will be decreased according to the logic of steps 917 through 919, described above.

If $F_IO_2$ input is greater than 0.4 (step 914) a check is made for the occurrence of an $F_IO_2$ bounce since the most recent of a mode or PEEP change or the last bounce; or within the last 27 hours (step 920). If a bounce has occurred within this interval, the bounce count is increased by 1 if it was previously zero or if the current bounce occurred within about 3 hours of the wait time end (step 921). If a decrease in $F_IO_2$ is followed by an increase within 45 minutes, with no intervening change in PEEP or Mode, or decrease in $F_IO_2$, then a "bounce" is considered to have occurred. The occurrence of several bounces typically indicates that the $F_IO_2$ is at the lowest setting that will sustain acceptable oxygenation. If there are more than 30 minutes between the present time and the wait end (step 922), a message is generated stating that the oxygenation protocols are in a waiting period, and indicating the delay until oxygen reduction can be carried out (step 925). If the current time is within 30 minutes of the wait end (step 922) but the current time is greater than the wait end (step 923), the wait end is set to the current time (step 924). If the $F_IO_2$ increase was not associated with the bounce, or two adjacent $F_IO_2$ decreases occurred, or if there was a PEEP increase since the latest of the end of the wait time and 27 hours ago (step 926) the Bounce count is set to zero (step 927) and step 928 is carried out. If the statement evaluated in step 926 was false, step 928 is carried out directly.

In step 928, a determination is made as to whether $O_2$ class is SuperSatisfactory. If it is, and $F_IO_2$ input is greater than 0.3 (step 929), a message instructing to decrease $F_IO_2$ by 0.1 to a minimum of 0.3 is generated (step 930). If $O_2$ class is not supersatisfactory, and $F_IO_2$ input is greater than 0.4 (step 931), or if $O_2$ class is SuperSatisfactory but $F_IO_2$ input is not greater than 0.3 (step 929), an instruction is generated stating that the patient is to be kept at minimum therapy (step 932). If $O_2$ class is supersatisfactory and $F_2O_2$ input is greater than 0.4 (step 931), an instruction to decrease $F_IO_2$ by 0.1, to a minimum of 0.4, is generated (step 933). After generation of an instruction message, or directly following step 916 if PEEP was increased in the last 6 hours, program control returns to CORE, from step 934. The medical logic used in the CPPV Oxygenation Reduction protocols is summarized in tables 6, 7 and 8.

CPAP Oxygenation Reduction

Figure 10A:
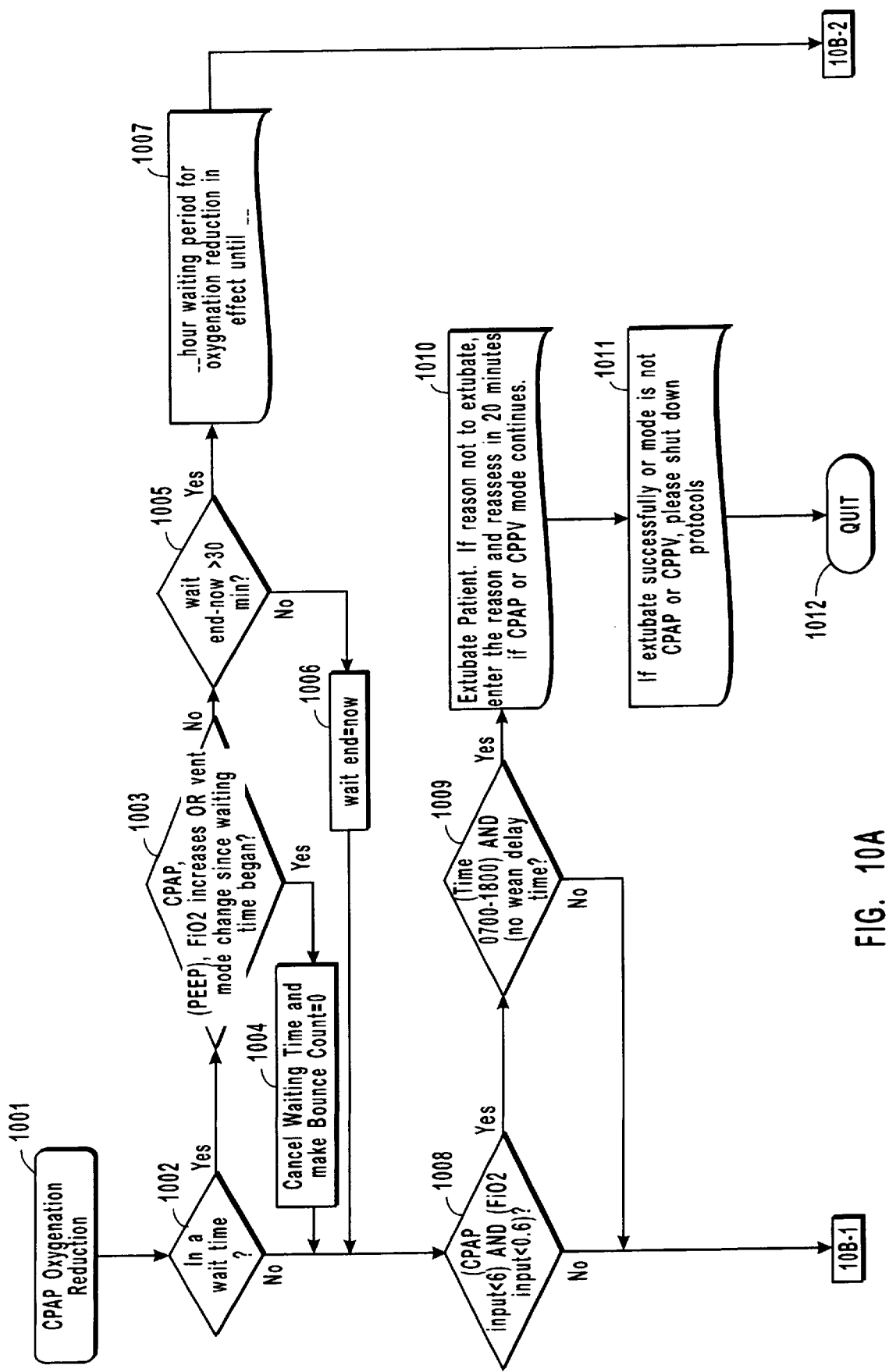
FIG. 10 is a flowchart diagram of the CPAP oxygenation reduction protocol.
Figure 10B:
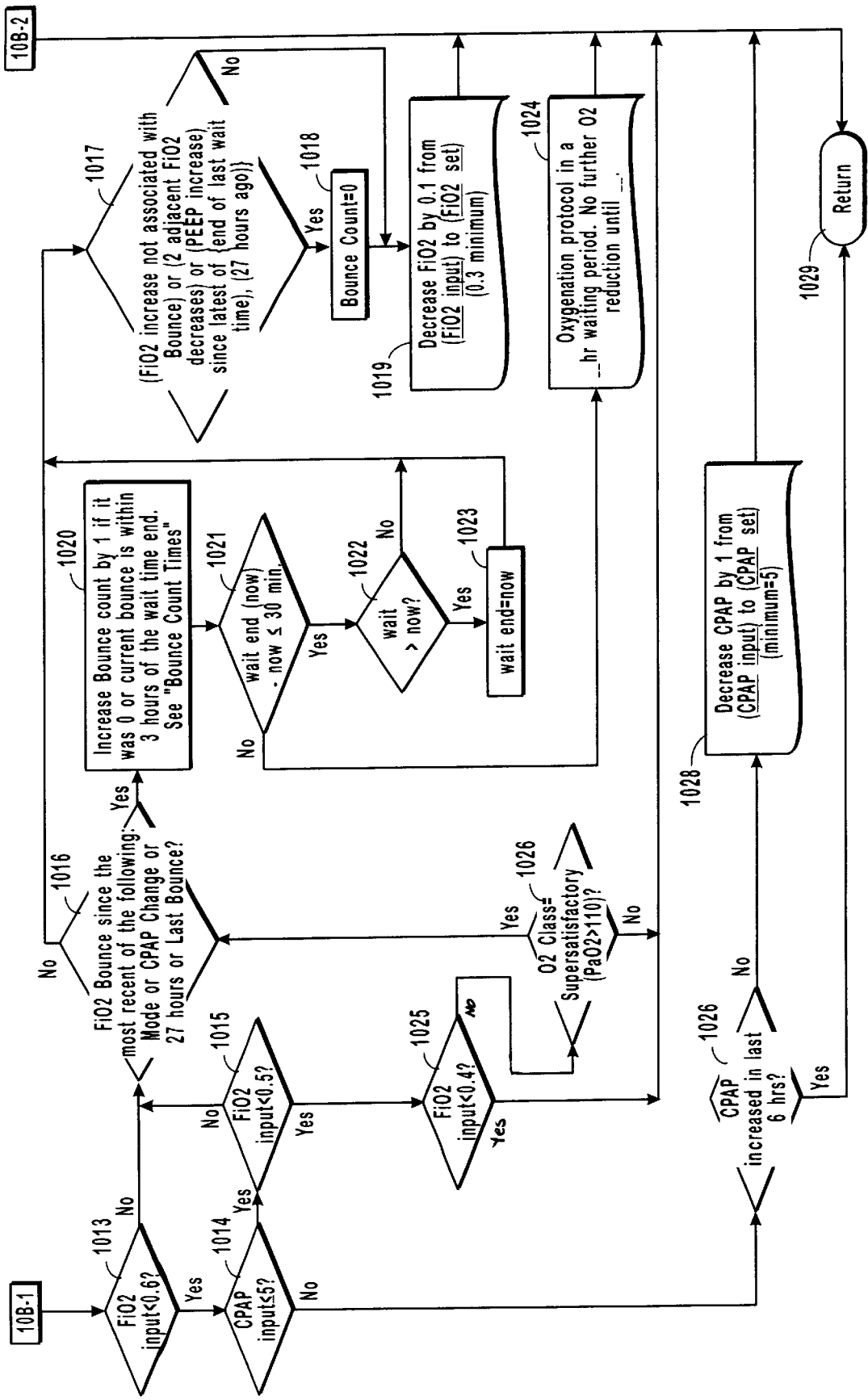

In the CPAP Oxygenation Reduction protocol (FIG. 10) instructions are generated for reducing CPAP or $F_IO_2$ or extubating the patient. The CPAP Oxygenation reduction protocol is entered at step 1001. If there is a wait time currently in effect (step 1002), or if a CPAP (PEEP) or $F_IO_2$ increase or vent mode change have occurred since the waiting time began (step 1003), the waiting time is canceled and the Bounce count is set to zero (step 1004). If the current time is within 30 minutes of the wait end (step 1005), the wait end is set to the current time (step 1006). If the current time is more than 30 minutes from the wait end, a message stating that a waiting period is in effect is generated (step 1007) and program control returns to CORE from step 1029. If there was no wait time, or the wait time was ended or canceled, program control goes to step 1008. If the CPAP input is less than 6 and the $F_IO_2$ input is less than 0.6 (step 1008), and it is during the day and there is no wean delay time (step 1009), an instruction for extubating the patent is generated (step 1010). A second message is generated instructing that the protocol be shut down if the patient was successfully extubated or if the mode is not CPAP or CPPV (step 1011), and the protocol is the quit at step 1012.

If $F_IO_2$ input is less than 0.6 (step 1013) and CPAP input is not less than or equal to 5 (step 1014), if CPAP was increased within the last 6 hours (step 1027), program control returns to CORE (step 1029). If at step 1027 CPAP was not increased within the last 6 hours, an instruction to decrease CPAP by 1, to a minimum of 5, is generated (step 1028). Program control then returns to CORE, from step 1029. If at step 1014 CPAP input was less than or equal to 5, and at step 1015, $F_IO_2$ input was less than 0.5, if $F_IO_2$ input is less than 0.4 (step 1025) program control returns to CORE, with no further action taken. If $F_IO_2$ input is not less than 0.4 (step 1025), and $O_2$ class is SuperSatisfactory (step 1026) a check is made for a recent $F_IO_2$ Bounce (step 1016). If, at step 1026, $O_2$ class was not SuperSatisfactory, program control returns to CORE from step 1027. The check for a recent $F_IO_2$ Bounce (step 1014) is carried out following step 1013 (if $F_IO_2$ input is not less than 0.6), step 1015 (if $F_IO_2$ input is not less than 0.5), or step 1026 (if $O_2$ class is SuperSatisfactory).

If an $F_IO_2$ bounce occurred since the most recent of a vent mode or CPAP change, the last bounce, or within the last 27 hours (step 1016), the bounce count is increased by 1 if it was 0 or if the current bounce is within the 3 hours of the wait time end (step 1020). If the current time is not within thirty minutes of the wait end (step 1021) a message is generated which states that the oxygenation protocol is in a waiting period and that no further $O_2$ reduction will be carried out for some period of time (step 1024). The program then returns to CORE. If the current time is within 30 minutes of the wait end (step 1021) or if it is less than the wait end time (step 1022), it is set equal to the wait end time (step 1023). Following step 1023, or step 1016 if no bounce had occurred within the indicated period, step 1017 is executed. If an $F_IO_2$ increase occurred which was not associated with a bounce, if two adjacent $F_IO_2$ decreases occurred, or if a PEEP increase occurred since the last wait time or in the last 12 hours (step 1017), the Bounce Count is set to zero (step 1018). An instruction to decrease $F_IO_2$ by 0.1 to a minimum of 0.3 is then generated (step 1019) and program control returns to CORE, from Step 1029. The rules used to determine the changes in CPAP and $F_IO_2$ in the CPAP Oxygenation Reduction protocol a re shown in tables 9, 10 and 11.

Weaning Assessment

Figure 11A:
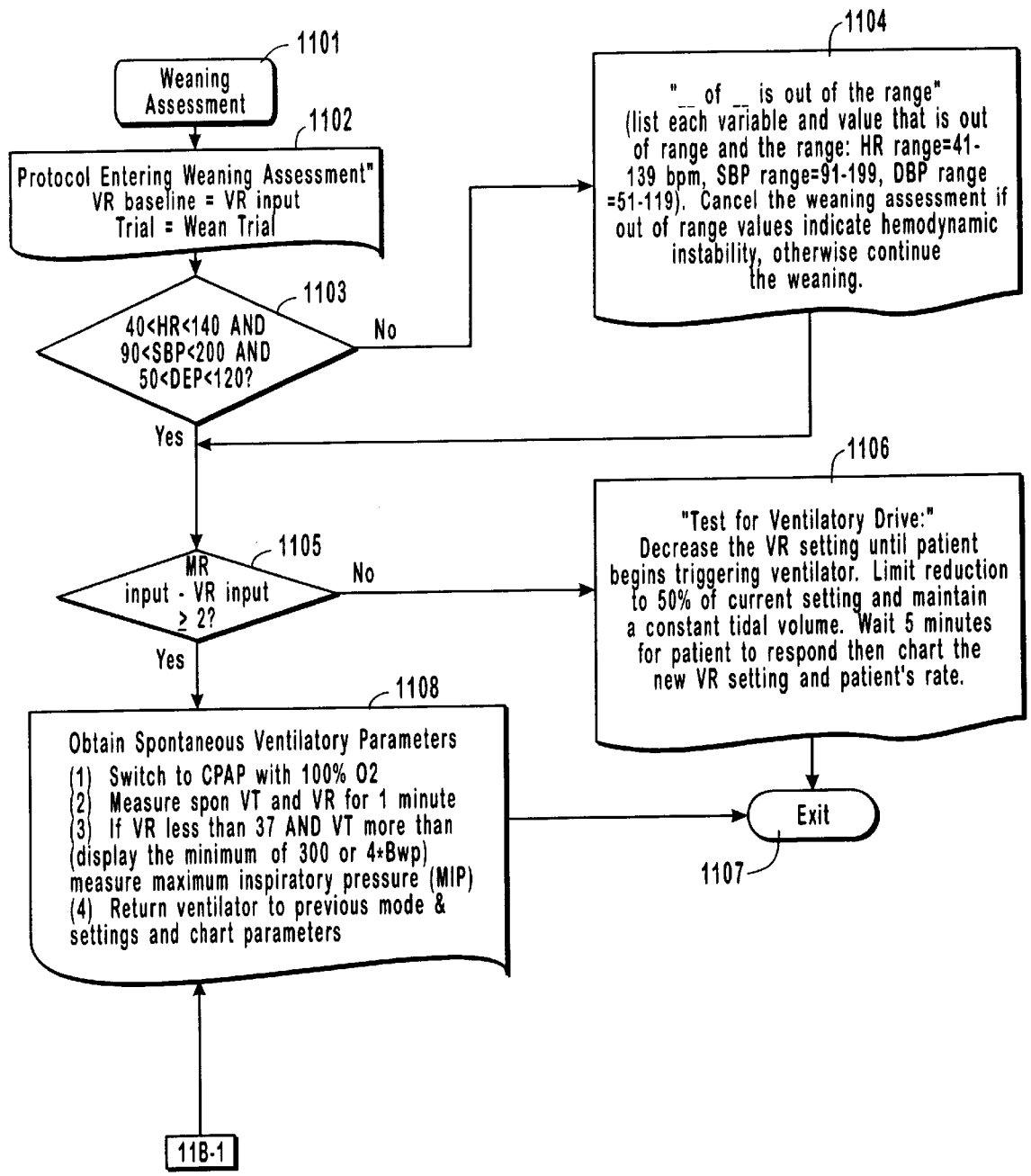
FIG. 11 is a flowchart diagram of the weaning assessment protocol.
Figure 11B:
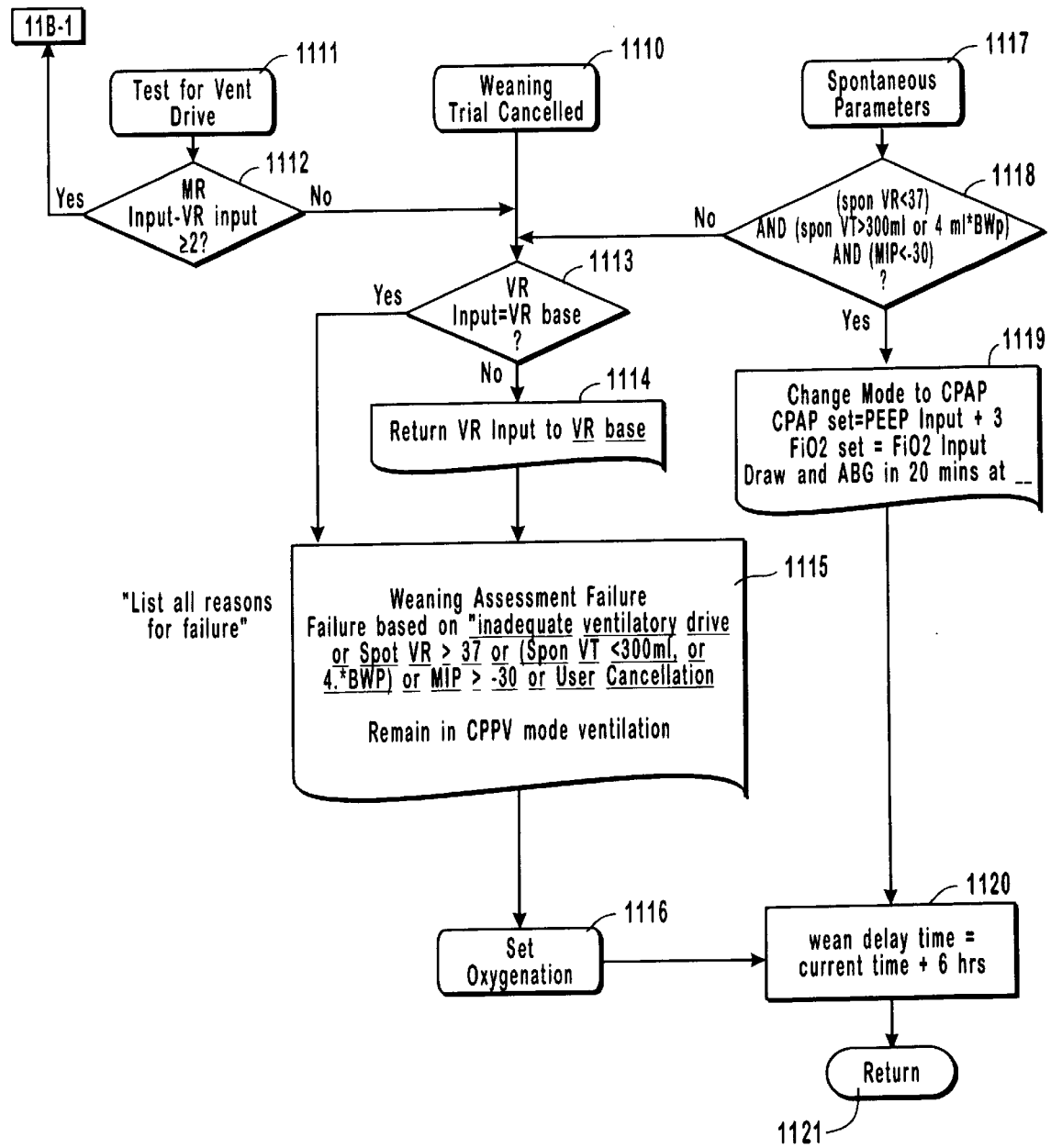

When program control is in the CPPV Oxygenation Reduction protocol, if the ventilatory rate, $F_IO_2$, and PEEP-$_{input}$ are sufficiently low and the $pH_a$ is sufficiently high, the patient is considered to be responding well to therapy and weaning assessment will be initiated (from step 905). The Weaning Assessment protocol is shown in FIG. 11. The protocol is entered at step 1101. A message is generated which states that the protocol is entering weaning assessment (step 1102). A check is made to determine whether heart rate and blood pressure are within appropriate ranges (step 1103). If not, a message is generated which states that weaning assessment should be canceled if the out of range values indicate hemodynamic instability (step 1104). If the protocol is canceled, program control returns to PROVIEW at step 221.

If MR is close to VR (step 1105) (i.e., the patient is primarily relying upon the ventilator), a message is generating instructing that a test for ventilatory drive be initiated (step 1106). The clinician is instructed to reduce the VR setting until the patient begins to t rigger the ventilator. If the difference between MR and VR is great enough (i.e., the patient is initiating breaths), the clinician is instructed to test spontaneous ventilatory parameters (step 1108). In the spontaneous parameters test, the ventilation mode is switched to CPAP with 100% $F_IO_2$, and the spontaneous minute ventilation, rate and maximum inspiratory pressure against a closed airway are measured. After new data have been obtained from either the ventilatory drive or spontaneous ventilatory parameters test, the clinician is instructed to chart the new data. Program control then exits the Weaning Assessment Protocol at step 1107 and returns to PROVIEW, at the "Continue Trial" option entry point (step 212).

An implicit decline check (step 213) and a data quality check (step 214) are performed from PROVIEW. At step 215 of PROVIEW, if an Increase VT Trial: Controlled was just being performed, step 227 is executed, which sets the status variables so that CORE is called as if the protocol was run normally with an ABG. If not, in step 216 a check is made as to whether a weaning Trial was being performed. If not, the Increase VT trial (Assisting Mode protocol shown in FIG. 15) is entered at the "In Progress" entry point (from step 217). If at step 216, it is found that a Weaning Trial was being performed if the trial was in the vent drive phase (step 218) the Weaning Trial is reentered at the Vent Drive test entry point from step 220. Otherwise, it is reentered at the Spont Params Entry Point, from step 219.

Weaning Trial Spont Params

Following entry of the Weaning Assessment Protocol at the Spontaneous Parameters Entry Point (step 1117), if the patient's spontaneous VR and MIP are low enough and VT is high enough (step 1118), a message is generated instructing that the ventilation mode be changed to CPAP, CPAP be set to PEEP$_{input}$+3, $F_IO_2$ be set to $F_IO_2$ input, and a new ABG be drawn in 20 minutes (step 1119). A weaning delay time is set assuring at least 6 hours before weaning would be re-attempted following a CPAP failure (step 1120). If VR and MIP are too high and VT is too low (step 1118), if $VR_{input}$ is equal to $VR_{base}$ (step 1113), a message is generated stating that Weaning Assessment has failed and listing the reasons (step 1115). If $VR_{input}$ is not equal to $VR_{base}$ (step 1113), a message is generated instructing that $VR_{input}$ be returned to $VR_{base}$ (step 1114), and the Weaning Assessment Failure message of step 1115 is generated. Oxygenation is then set (step 1116). The wean delay time is set (step 1120) and, following step 1120, control returns to PROVIEW from step 1121.

Weaning Trial Vent Drive Test

Following entry into the Weaning Assessment Protocol at the Test for Vent Drive entry point (step 1111), if $MR_{input}$ is greater than $VR_{input}$ by at least 2 (step 1112), the clinician is instructed to switch ventilation to CPAP and determine spontaneous ventilation parameters (step 1108). Otherwise, weaning assessment is considered to have failed, and step 1113 and subsequent steps are carried out as described previously. If the weaning trial is canceled, PROVIEW is entered at the Cancel Trial Option entry point (step 221). Following a Data Quality check (step 222), at step 223 a check is made for whether an Increase VT Trial: controlled was being performed. If this was the case, CORE is executed immediately.

At step 224, a check is made for whether a Weaning Trial was in progress. If so, the Weaning Trial is reentered at the "Canceled" entry point (from Step 225) if not, the increase VT Trial (Assisting Mode) protocol would be reentered at the In Progress entry point (from step 226). When the Weaning Trial is entered at the "canceled" entry point (step 1110) step 1113 and subsequent steps are carried out as described previously. Following step 1120 (setting of the delay time) program control returns to PROVIEW from step 1121.

After program control returns to PROVIEW from CORE or the Weaning Trial (from the Spont Parameters, Vent Drive Test, or Cancel portions) step 205 of PROVIEW is executed. In this step, it is determined whether program control just came from the Weaning Trial. If so, and the patient passed the Weaning Trial (step 209) PROVIEW is exited from step 208, and the protocols are ended. Similarly, if the patient did not pass the trial, but the Trial was not originated with ABG data (step 210), PROVIEW is exited. If the Weaning Trial was not just performed (as determined at step 205), but the protocols were run from $S_pO_2$ or in CPAP mode (step 206), or if the Weaning Trial was originated with ABG data (step 210), the CPPV ventilation protocol is called from step 207 of PROVIEW, following which PROVIEW is exited from step 208.

Set Oxygenation

Figure 12:
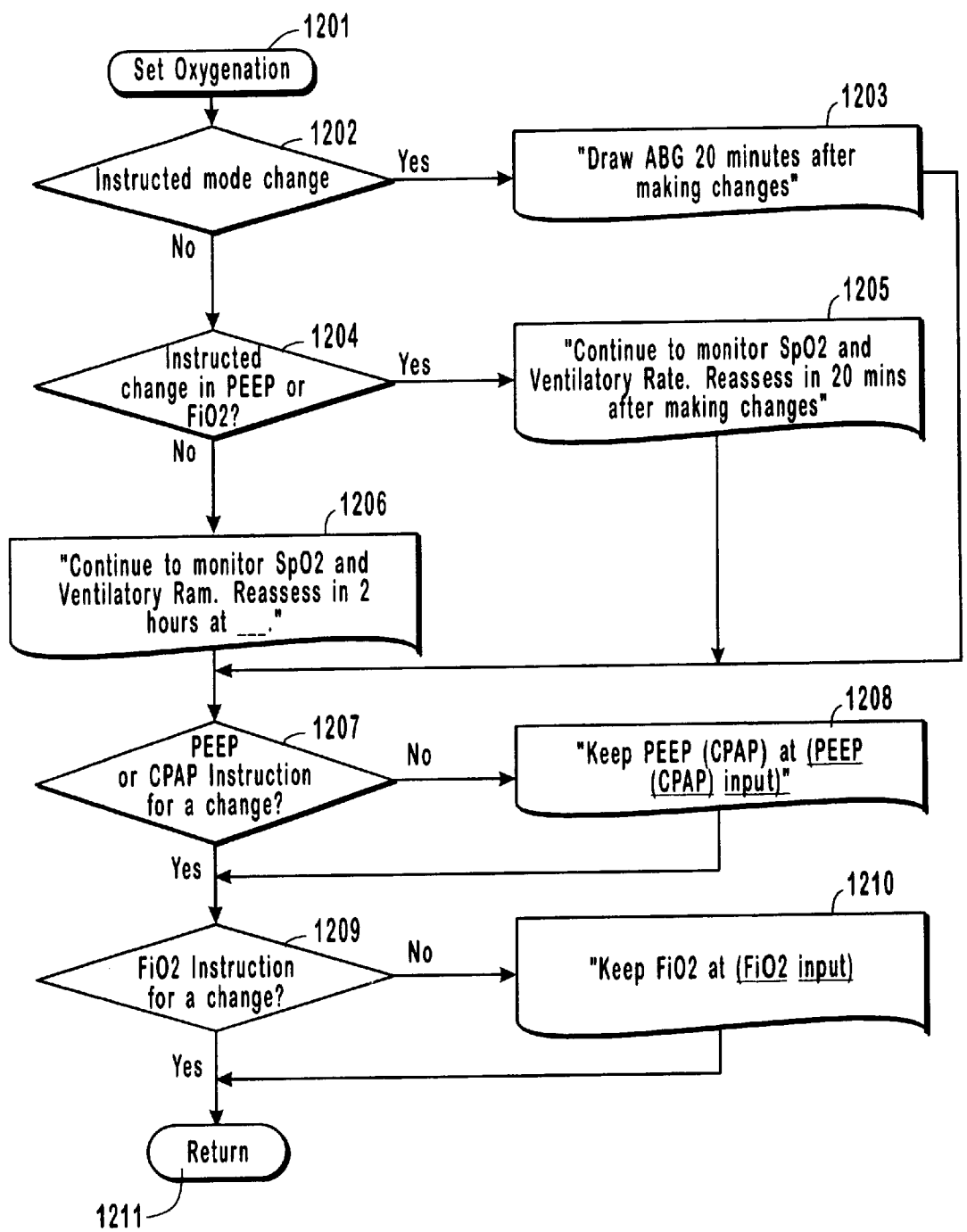
FIG. 12 is a flowchart diagram of the set oxygenation protocol.

Unless the Weaning Assessment protocol was called from one of the Oxygenation Reduction or Increase protocol, program control returns to CORE when the Oxygenation Reduction or Increase protocol has been completed. After returning to CORE, the Set Oxygenation protocol shown in FIG. 12 is run from step 417 and then program control returns to PROVIEW from step 418.

The Set Oxygenation protocol either instructs the clinician to enter new ABG or $SpO_2$ data at an appropriate interval (if a change to the ventilator settings was made), or to keep the settings the same and reassess SpO2 and ventilatory rate after a suitable delay. The set oxygenation protocol is entered at step 1201. If a mode change (i.e., between CPPV and CPAP) has been instructed (step 1202), a message is generated instructing that an ABG be drawn 20 minutes after making the change (step 1203). If no mode change was instructed, but a change in PEEP or $F_IO_2$ was instructed (step 1204), a message is generated instructing to continue monitoring $SpO_2$ and ventilatory rate, and reassess the patient 20 minutes after making changes (step 1205). If no changes in mode, PEEP, or $F_IO_2$ were instructed, an instruction to continue monitoring $SpO_2$ and ventilatory rate, and to reassess in 2 hours, is generated (step 1206). If no instruction for changing PEEP (or CPAP) was generated (step 1207), a message to keep PEEP at the current value is generated (step 1208). If no instruction for chancing $F_IO_2$ has been generated (step 1209) a message to keep $F_IO_2$, at the current value is generated (step 1210). Program control then returns to the calling protocol (either CORE or Weaning Assessment) from step 1211.

CPPV Ventilation

Figure 13A:
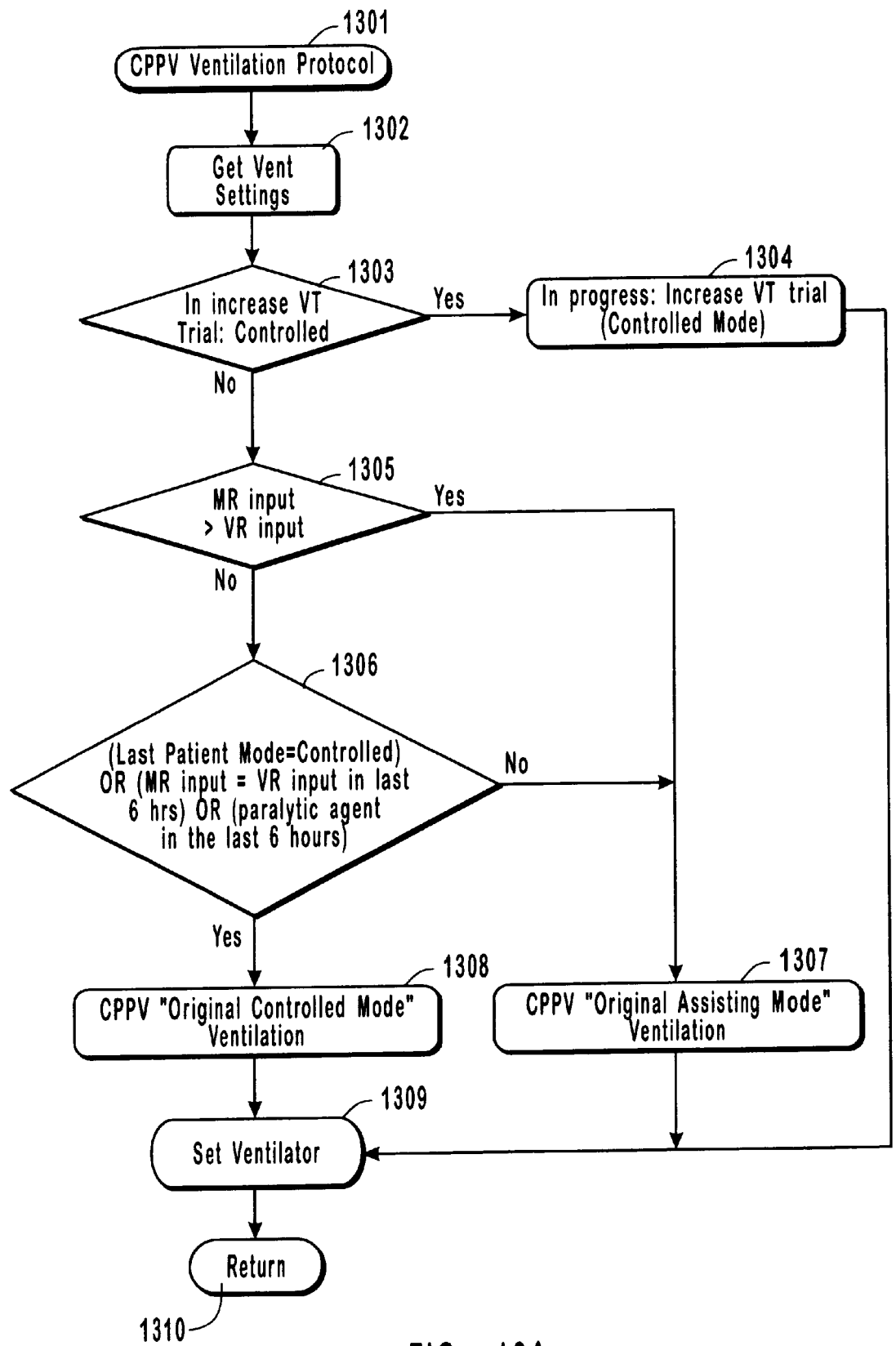
FIG. 13A is a flowchart diagram of the CPPV ventilation protocol.

The CPPV ventilation protocol is shown in FIG. 13A. It is entered at step 1301. The first task performed by this protocol is to check the ventilator settings (step 1302), by following the logic of the Get Vent Settings protocol shown in FIG. 13B.

The Get Vent Settings Protocol is entered at step 1311. Settings and instructions may be ventilator mode -and manufacturer-specific. Use of ventilator-specific settings and instructions falls within the scope of the invention. If the ventilator is a PB7200 (step 1312), $VT_{corr\ insp}$ is set to $VT_{input}$ (step 1316). If the ventilator is a 900C (step 1313), $VT_{uncorr\ insp}=1000*VE_{input}/VR_{input}$ and $VT_{corr\ insp}=VT_{uncorr\ insp}=(P_{peak}-PEEP_{input})*Ctc$ (step 1315). If any other type of ventilator is in use, $VT_{uncorr\ insp}$ is set to $VT_{input}$ and $VT_{corr\ insp}$ is set to $VT_{uncorr\ insp}-(P_{peak}-PEEP_{input})*C_{tc}$(step 1314). After the $VT_{corr\ insp}$ values are set, $VE_{corr\ insp}$ is set to $MR_{input}*VT_{corr\ insp}/1000$ (step 1317) and program control returns to the protocol from which it was called (step 1318).

Figure 15A:
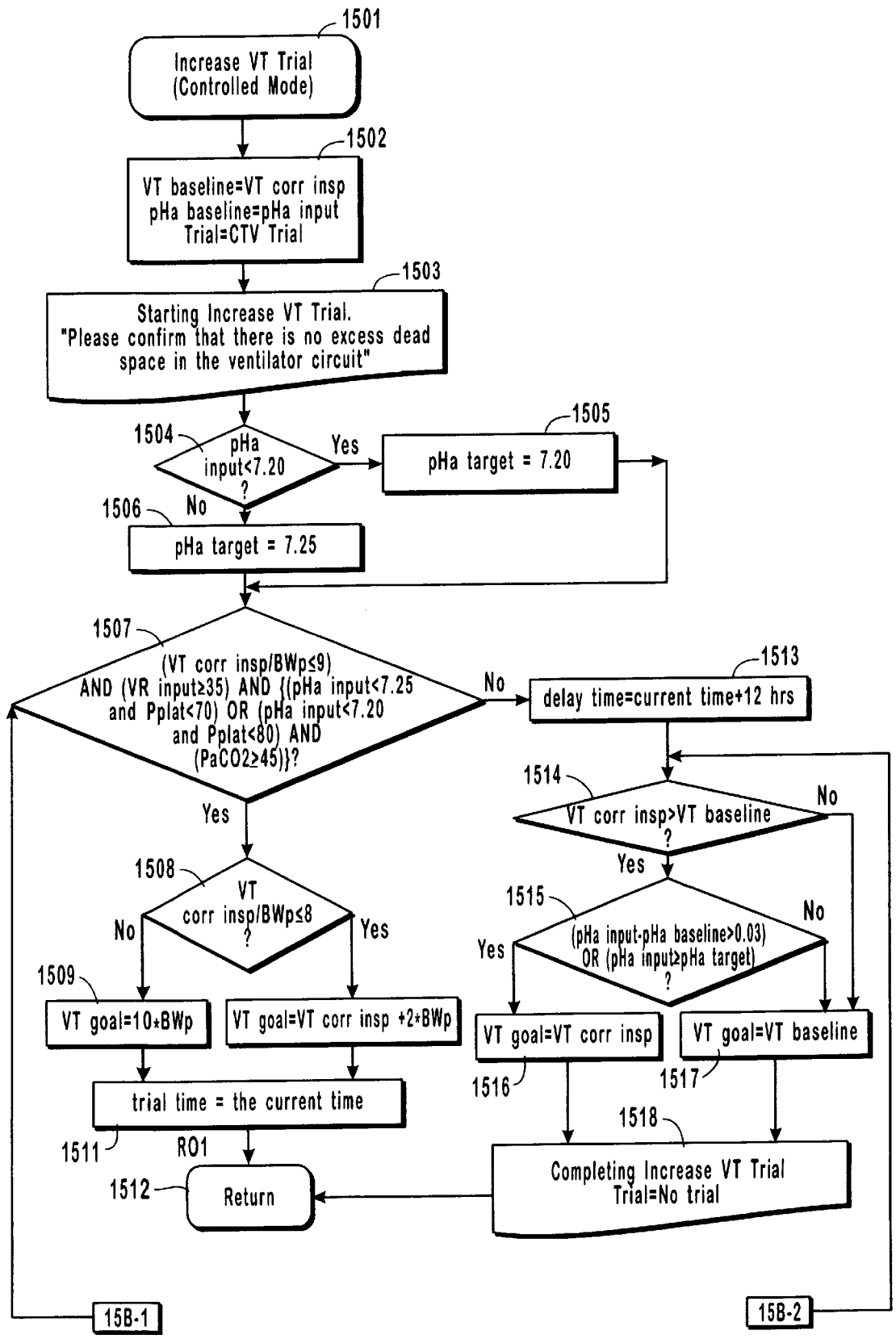
FIG. 15 is a flowchart diagram of the increase VT Trial Controlled protocol.
Figure 15B:
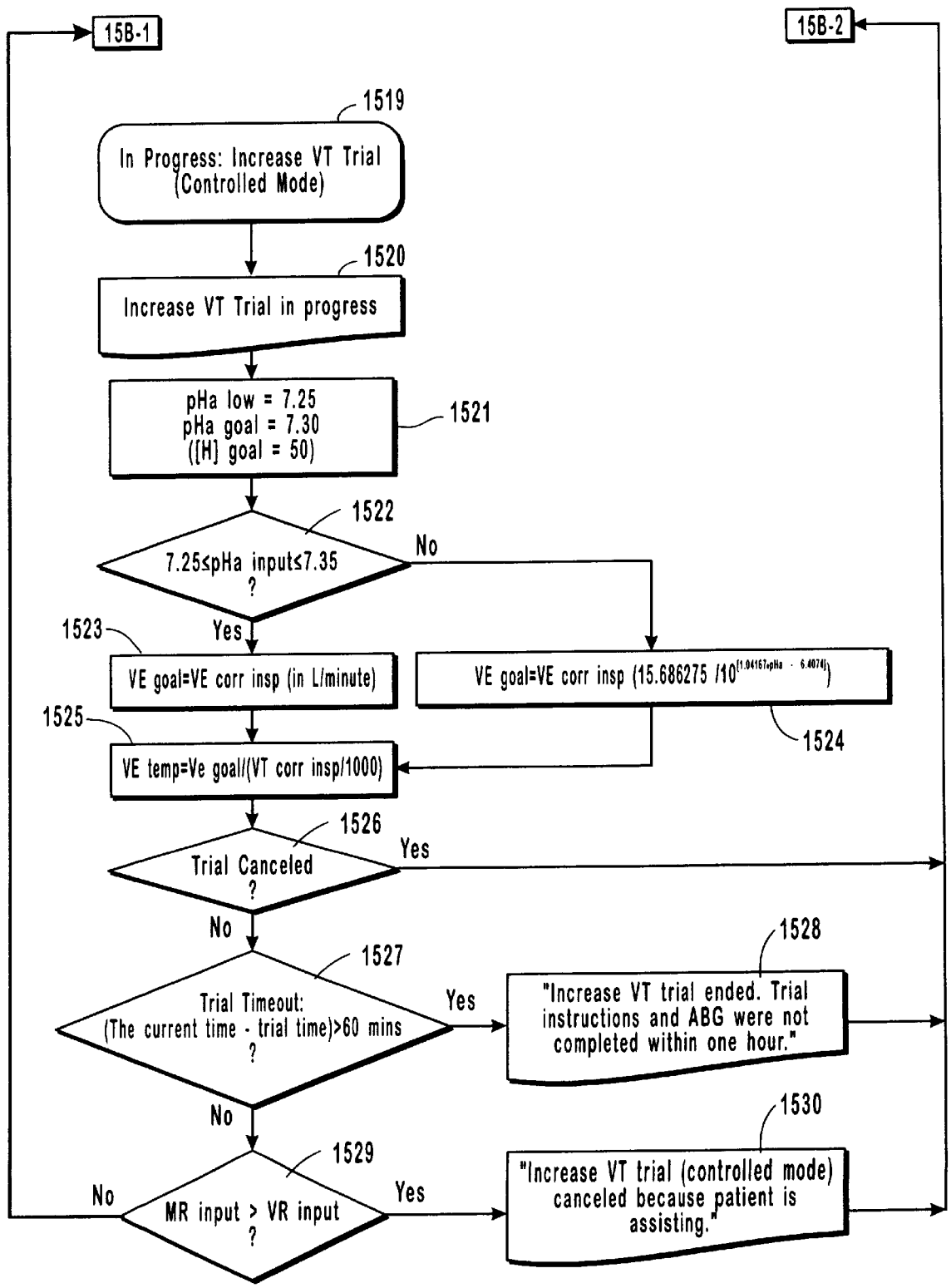

After the vent settings have been determined, if the CPPV ventilation protocol was called while an Increase VT Trial (controlled mode) was being performed (step 1303), the Increase VT Trial (controlled Mode) Protocol is entered (from step 1304) at the "In Progress" entry point (step 1519 in FIG. 15). If an Increase VT Trial was not in progress, $MR_{input}$ is compared to $VR_{input}$ (step 1305).

Figure 18A:
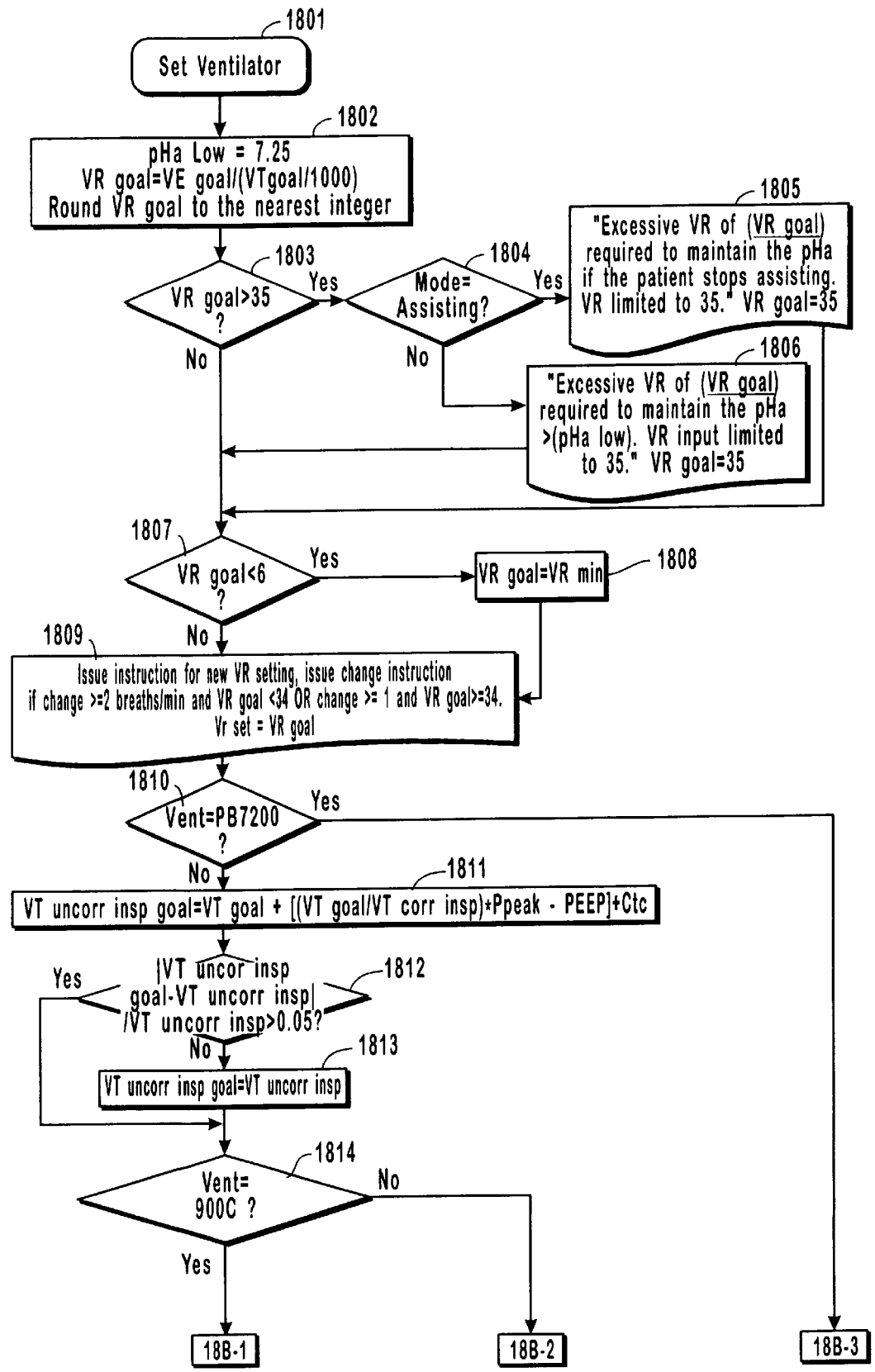
FIG. 18 is a flowchart diagram of the set ventilator protocol.
Figure 18B:
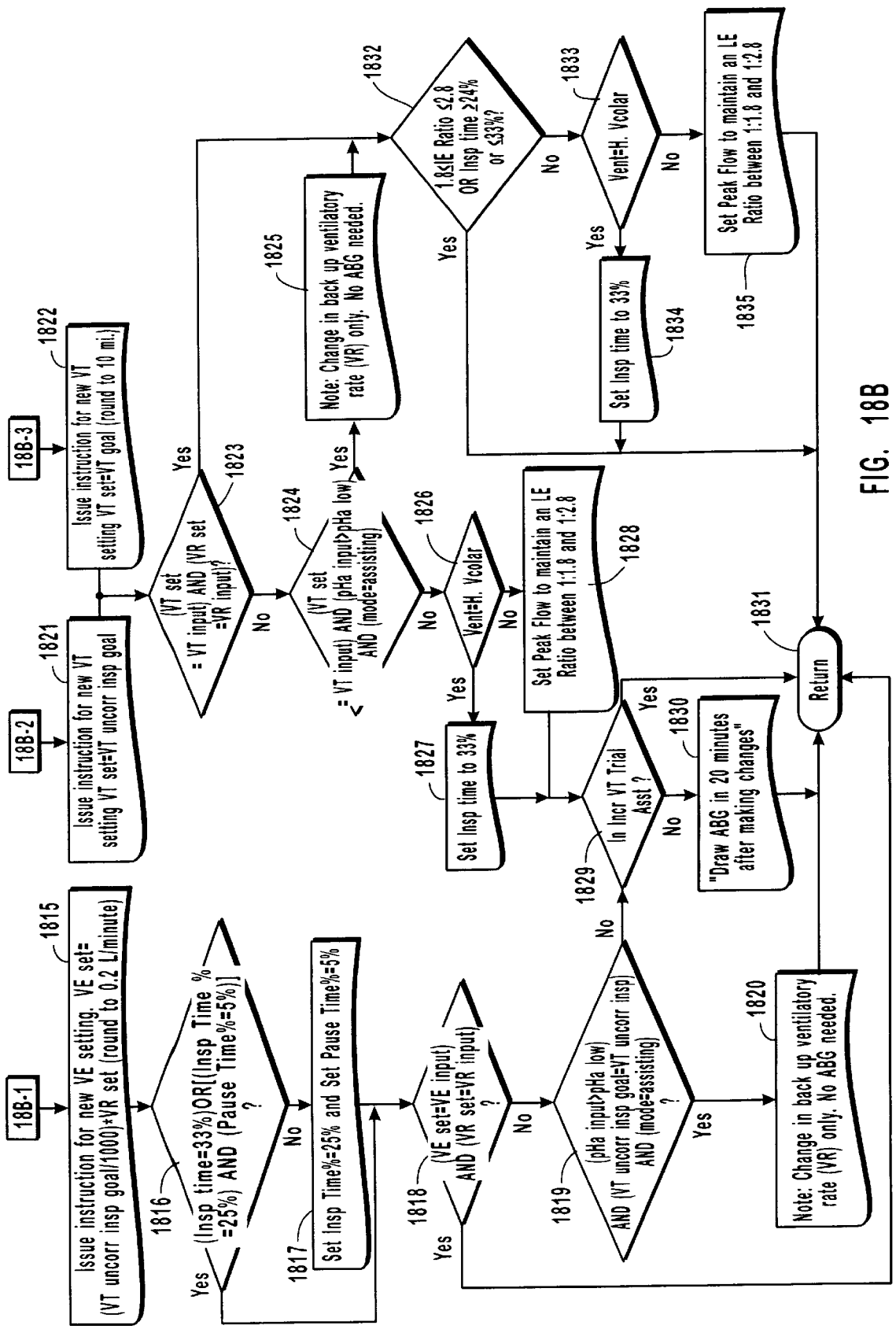

If $MR_{input}$ is greater, the CPPV "Original Assisting Mode" protocol is called (step 1307). Otherwise, in step 1306 several parameters are considered in determining whether controlled assisting mode ventilation should be used. If the last patient mode was controlled, if $MR_{input}$ was equal to $VR_{input}$ in the last 6 hours, or if a paralytic agent was used in the last 6 hours, the CPPV "Original Controlled Mode" Ventilation protocol is called (step 1308). Otherwise the CPPV "Original Assisting Mode" ventilation Protocol is called (step 1307). The set ventilator protocol shown in FIG. 18 is called (step 1309) and program control then returns to CORE (from step 1310).

CPPV Controlled Mode Ventilation

Figure 14:
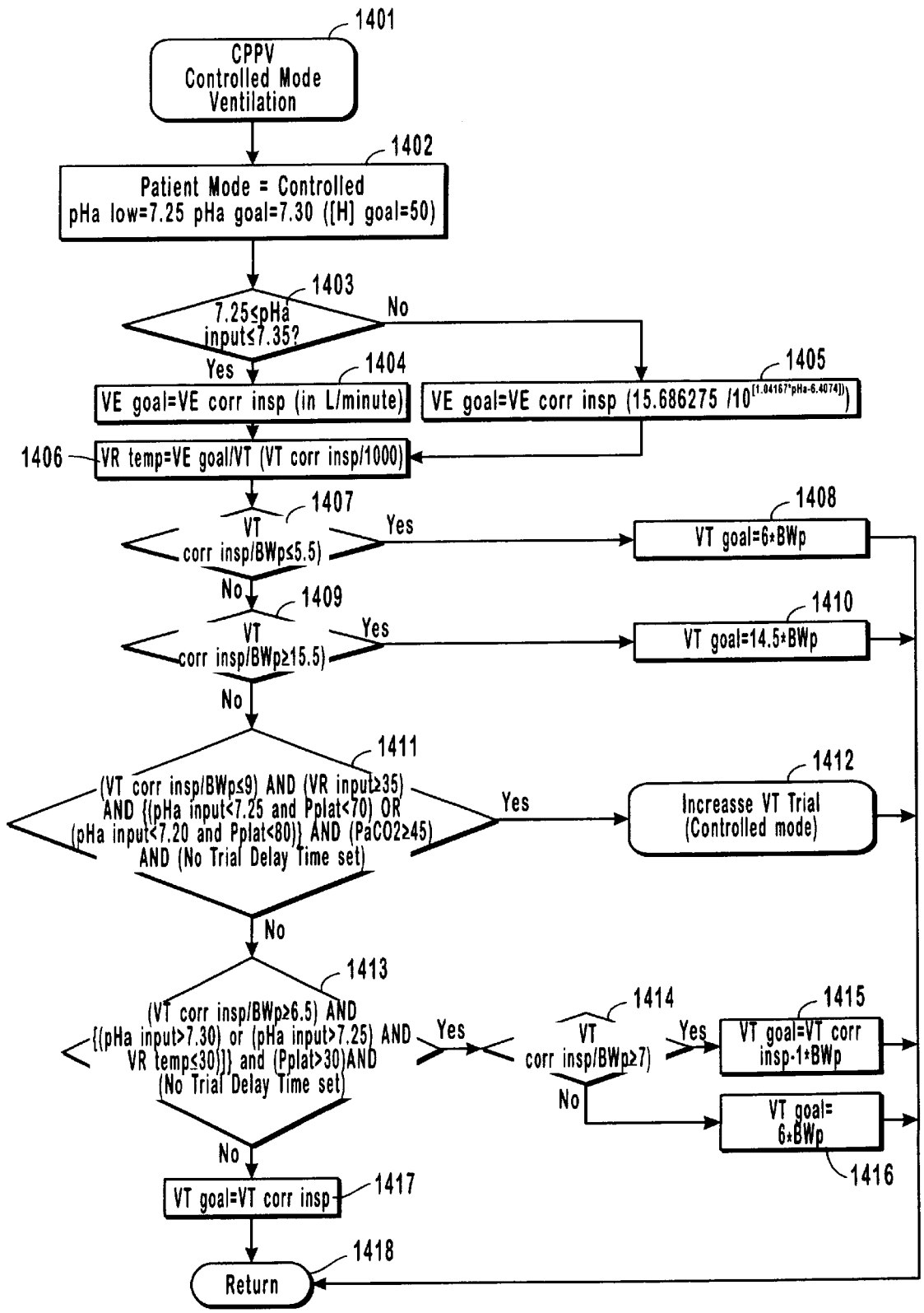
FIG. 14 is a flowchart diagram of the CPPV controlled mode ventilation protocol.

The CPPV controlled mode ventilation protocol is shown in FIG. 14. In this protocol, goals are set for VE and VT, and the VR needed to obtain the goal VE is calculated. The protocol is entered at step 1401. The patient mode is set to "controlled", and minimum $pH_a$, $[H^+]_{goal}$, and $PaCO_2$ goals are set (step 1402). If $pH_a$ input is low (between 7.25 and 7.35) (step 1403), $VE_{goal}$ is set to $VE_{corr\ insp}$ (step 1404). Otherwise, $VE_{goal}$ is set to $VE_{corr\ insp}*(15.686275/10^{[1.04167*pHa-6.4074]})$ (step 1405). Following step 1404 or 1405, $VR_{temp}$ is then calculated as $VE_{goal}/(VT_{corr\ insp}/1000)$ (step 1406). If $VT_{corr\ insp}/BW_p$ is less than or equal to 5.5 (step 1407), $VT_{goal}$ equals $6*BW_p$ (step 1408). If $VT_{corr}$ $_{insp}/BW_p$ is greater than or equal to 15.5 (step 1409), $VT_{goal}$ equals $14.5*BW_p$ (step 1410).

If $VT_{corr\ insp}/BW_p$ is less than or equal to nine, $VR_{input}$ is greater than or equal to 35, $pH_a$ input is less than 7.25, and $P_{plat}$ is less than 70; or if $pH_a$ input is less than 7.2, $P_{plat}$ is less than 80, $PaCO_2$ is greater than or equal to 45, and the current time is less than or equal to the delay time, the increase VT Trial (controlled mode) protocol is called (step 1412). Otherwise, if $VT_{corr\ insp}/BW_p$ is greater than or equal to 6.5, $P_{plat}$ is greater than 30, no Trial Delay Time has been set, and either $pH_a$ input is greater than 7.3 or $pH_a$ input is greater than 7.25 while $VR_{temp}$ is less than or equal to 30 (step 1413), then in step 1414 $VT_{corr\ insp}/BW_p$ is evaluated. If it is greater than or equal to 7, then $VT_{goal}$ is set to $VT_{corr\ insp}-1*BW_p$. (step 1415). If it is less than 7, then $VT_{goal}$ is set to $6*BW_p$ (step 1416). Finally, if some or all of the conditions evaluated in step 1413 did not hold, $VT_{goal}$ is set to $VT_{corr\ insp}$ (step 1417). Program control returns to the CPPV ventilation protocol from step 1418.

Increase VT Trial (Controlled)

The Increase VT trial (controlled) protocol is shown in FIG. 15. When called from the CPPV controlled mode ventilation protocol, the increase VT trial (controlled) protocol is entered at step 1501. $VT_{baseline}$ and $pH_a$ baseline are set, and the trial is set to CTV Trial (step 1502). A message is generated which states that the increase VT trial is being started, and the clinician is asked to confirm that there is no excess dead space in the ventilator circuit (step 1503). If $pH_a$ is less than 7.2 (step 1504), $pH_a$ target is set to 7.2 (step 1505). Otherwise, $pH_a$ target is set to 7.25 (step 1506). If $VT_{corr\ insp}/BW_p$ is less than or equal to nine, $VR_{input}$ is greater than or equal to 35, and either $pH_a$ input is less than 7.25 while $P_{plat}$ is less than 70 or $pH_a$ input is less than 7.20 while $P_{plat}$ is less than 80 and $PaCO_2$ is greater than or equal to 45 (step 1507), then step 1508 is executed. If $VT_{corr\ insp}/BW_p$ is less than or equal to 8 (step 1508), $VT_{goal}$ is set to $VT_{corr\ insp}+2*BW_p$ (step 1510). If in step 1508, $VT_{corr\ insp}/BW_p$ is greater than 8, $VT_{goal}$ is set to $10*BW_p$ (step 1509). The trial time is set to the current time (step 1511), and program control returns to the CPPV controlled mode ventilation protocol from step 1512.

If the conditions evaluated at step 1507 do not hold, the delay time is set to the current time plus 12 hours (step 1513). If $VT_{corr\ insp}$ is greater than $VT_{baseline}$ (step 1514), then if $pH_a$ input—$pH_a$ baseline is greater than 0.03 or $pH_a$ input is greater than or equal to $pH_a$ target (step 1515), $VT_{goal}$ is set to $VT_{corr\ insp}$ (step 1516). If the conditions evaluated in step 1515 do not hold, $VT_{goal}$ is set to $VT_{baseline}$ (step 1517). $VT_{goal}$ is also set to $VT_{baseline}$ if $VT_{corr\ insp}$ is not greater the $VT_{baseline}$ (step 1514). Following completion of step 1516 or 1517, a message stating that the Increase VT Trial is being completed is generated, and Trial is set to No Trial (step 1518). Program control then returns to the CPPV controlled Mode ventilation protocol from step 1512.

CPPV Assisting Mode Ventilation

Figure 16A:
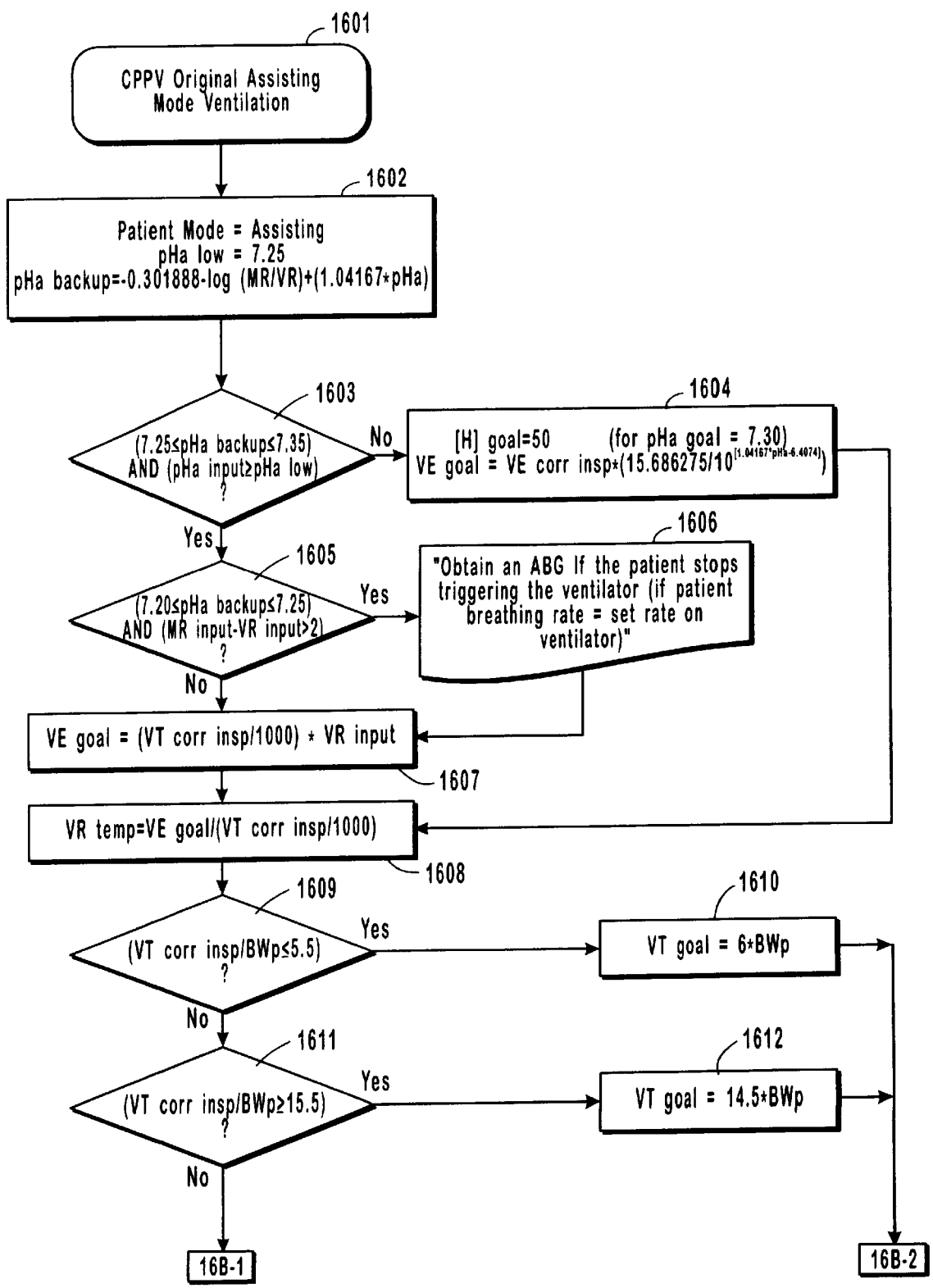
FIG. 16 is a flowchart diagram of the CPPV assisting mode ventilation protocol.
Figure 16B:
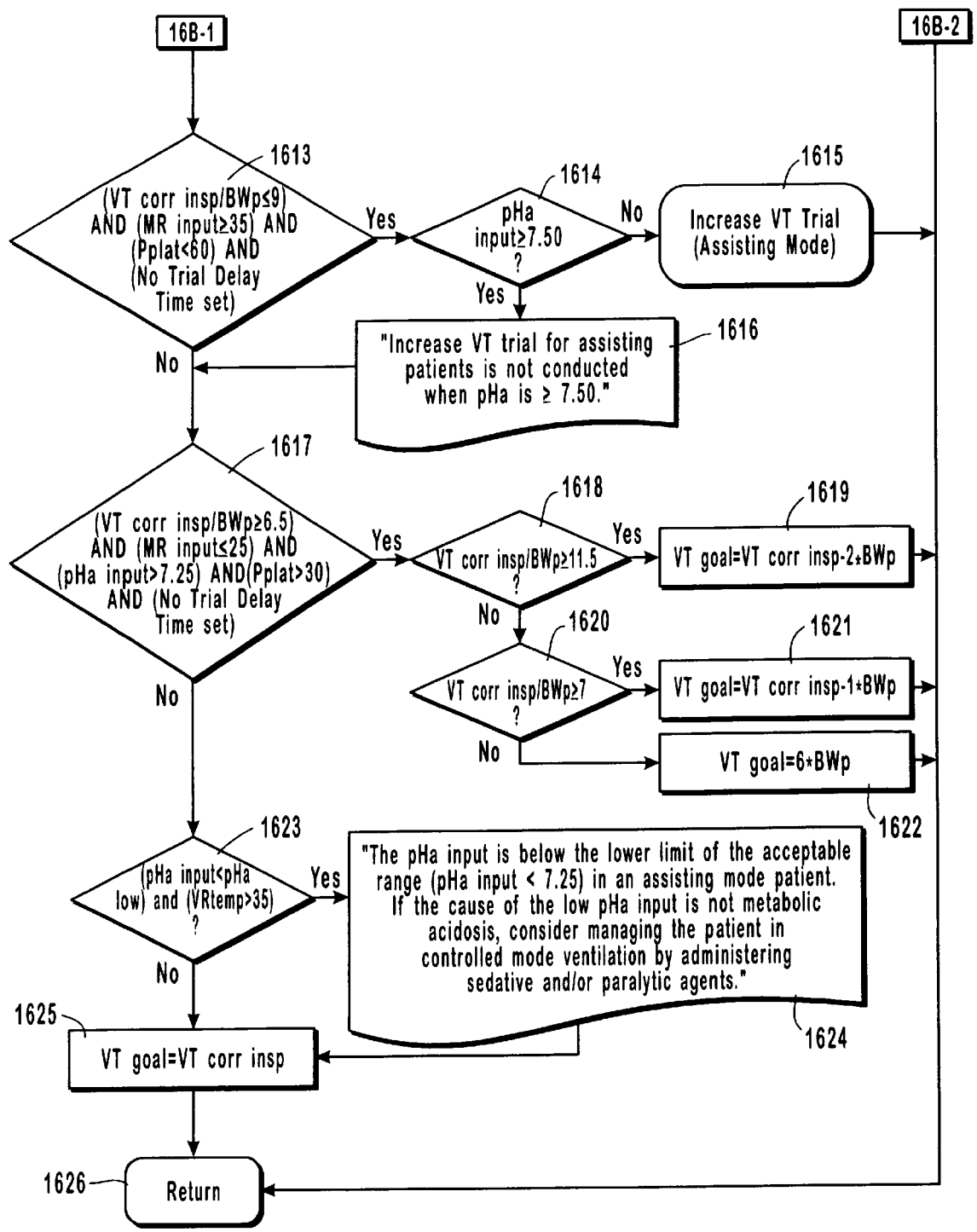

The CPPV assisting mode ventilation protocol is shown in FIG. 16. In this protocol, $VE_{goal}$ is set. $VT_{goal}$ is calculated on the basis of the patient's current $pH_a$ and $BW_p$, with the goal of bringing the patient's $pH_a$ into the desired range. The protocol is entered at step 1601. At step 1602, patient mode is set to Assisting, $pH_a$ low is set to 7.25, and $pH_a$ backup is set to $-0.301888-\log(MR/VR)+(1.04167*pH_a)$.

If $pH_a$ backup is not between 7.20 and 7.35, and $pH_a$ input is not greater than or equal to $pH_a$ low (step 1603), $[H^+]$ goal is set to 50 and $VE_{goal}$ is set to $VE_{corr\ insp}*(15.686275/10^{[1.04167*pHa-6.4074]})$ (step 1604), and step 1608 is executed. Otherwise, if $pH_a$ backup is between 7.20 and 7.25 and $(MR_{input}-VR_{input})$ is greater than or equal to 2 (step 1605), a message is generated stating that an ABG should be obtained if the patient stops triggering the ventilator (step 1606). Following either step 1605 or 1606, $VE_{goal}$ is set to $(VT_{corr\ insp}/1000)*VR_{input}$ (step 1607). $VR_{temp}$ is set to $VE_{goal}/(VT_{corr\ insp}/1000)$ (step 1608).

If $VT_{corr\ insp}/BW_p$ is less than or equal to 5.5 (step 1609), $VT_{goal}$ is set to $6*BW_p$ (step 1610). If $VT_{corr\ insp}/BW_p$ is greater than or equal to 15.5 (step 1611) $VT_{goal}$ is set to $14.5*BW_p$ (step 1612). If $VT_{corr\ insp}/BW_p$ is less than or equal to 6.5, $MR_{input}$ is less than 25, $pH_a$ is greater than 7.25, $P_{plat}$ is greater than 30, and no Trial Delay Time has been set (step 1617), if $VT_{corr\ insp}/BW_p$ is greater than or equal to 11.5 (step 1618) $VT_{goal}$ is set to $VT_{corr\ insp}-2*BW_p$ (step 1619). If $VT_{corr\ insp}/BW_p$ is less than 11.5, but greater than or equal to 7 (step 1620), $VT_{goal}$ is set to $VT_{corr\ insp}-1*BW_p$ (step 1621). If $VT_{corr\ insp}/BW_p$ is less than 7, VT goal is set to $6*BW_p$ (step 1622). If the conditions of step 1617 are not met, if $pH_a$ input is less than $pH_a$ low and $VR_{temp}$ is greater than 35 (step 1623), a message is generated stating that $pH_a$ input is below the acceptable range lower limit and suggesting the use of controlled mode ventilation (step 1624). Following step 1623 or 1624, $VT_{goal}$ is set as $VT_{corr\ insp}$ (step 1625). After $VT_{goal}$ has been set or the Increase VT Trial (Assisting Mode) protocol has been called, control returns to the CPPV Ventilation protocol from step 1626.

Increase VT Trial Assisting

Figure 17A:
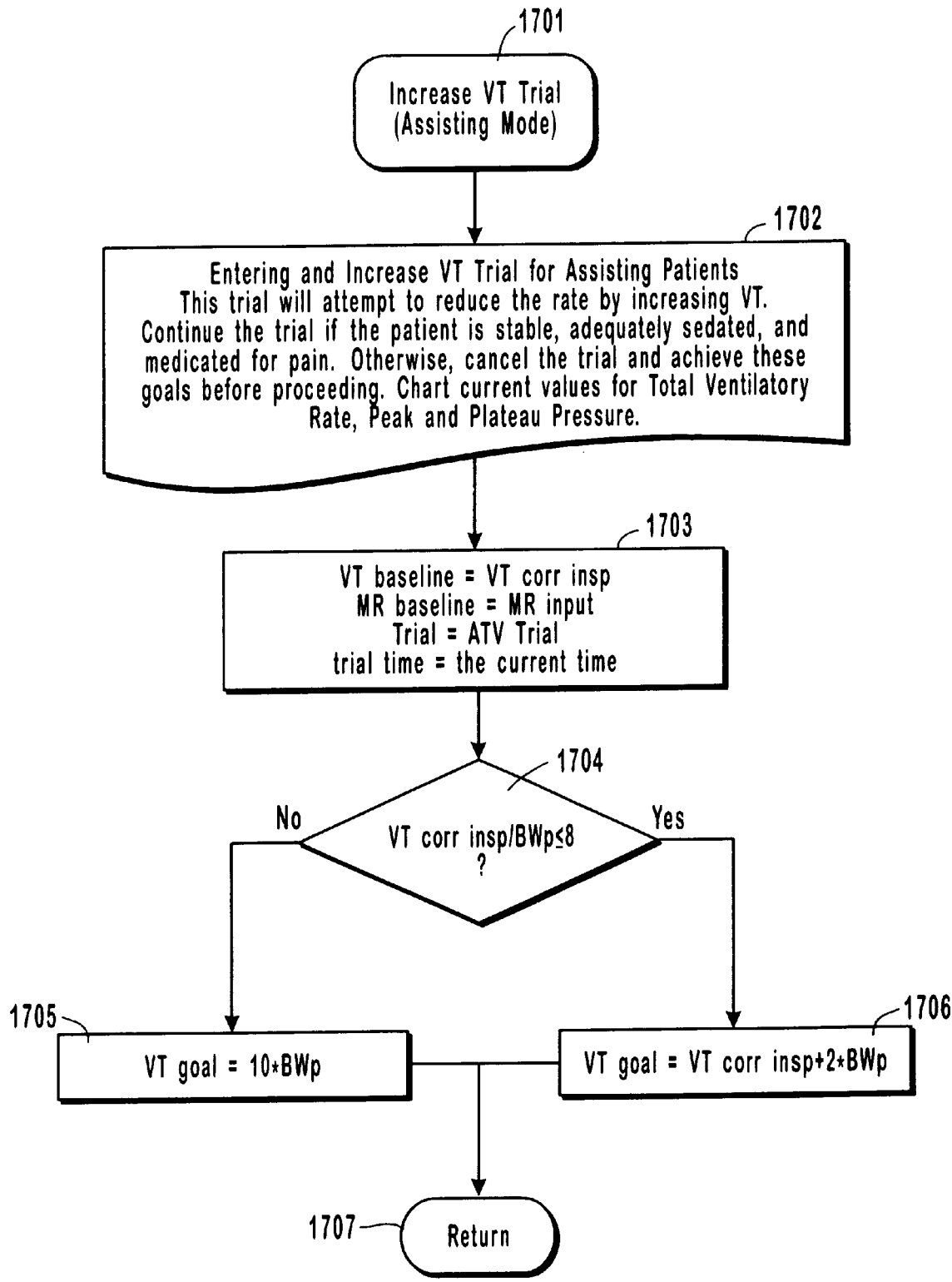
FIG. 17 is a flowchart diagram of the increase VT Trial assisting protocol.
Figure 17B:
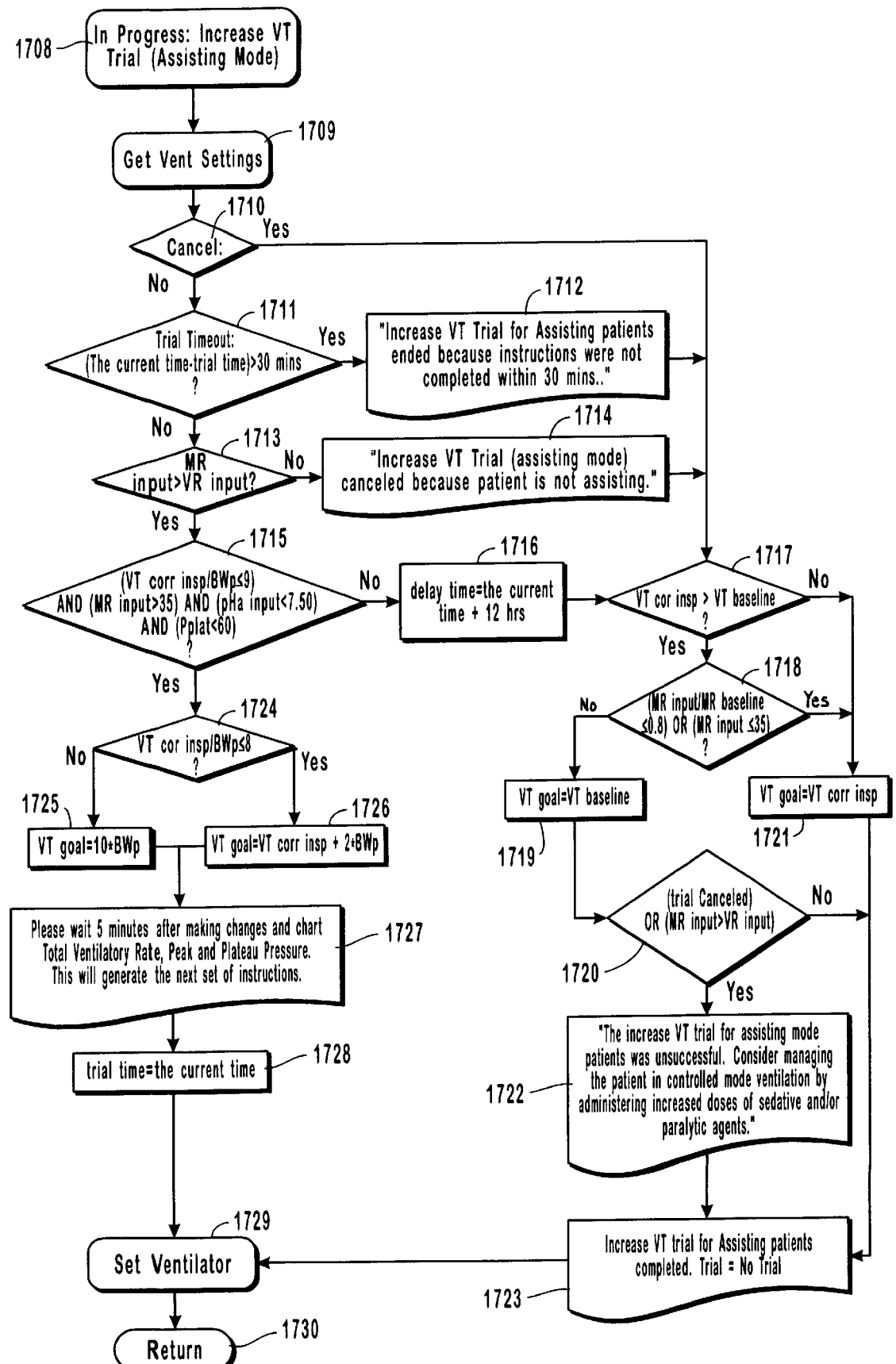

The Increase VT Trial (Assisting Mode) protocol is shown in FIG. 17. When called from the CPPV (assisting mode) ventilation protocol, the Increase VT Trial (Assisting Mode) protocol is entered at step 1701. A message is generated informing the user that the trial should not be performed unless the patient is stable, adequately sedated, and medicated for pain (step 1702). If the patient condition is appropriate and the clinician chooses to continue the trial, baseline values are set for VT and MR, Trial is set to ATV Trial and the trial time is set to the current time (step 1703). If $VT_{corr\ insp}/BW_p$ is less than or equal to 8 (step 1704), then $VT_{goal}$ is set to $VT_{corr\ insp}+2*BW_p$ (step 1706). If not, $VT_{goal}$ is set to $10*BW_p$. After $VT_{goal}$ is set, program control returns to the calling protocol from step 1707.

Figure 13B:
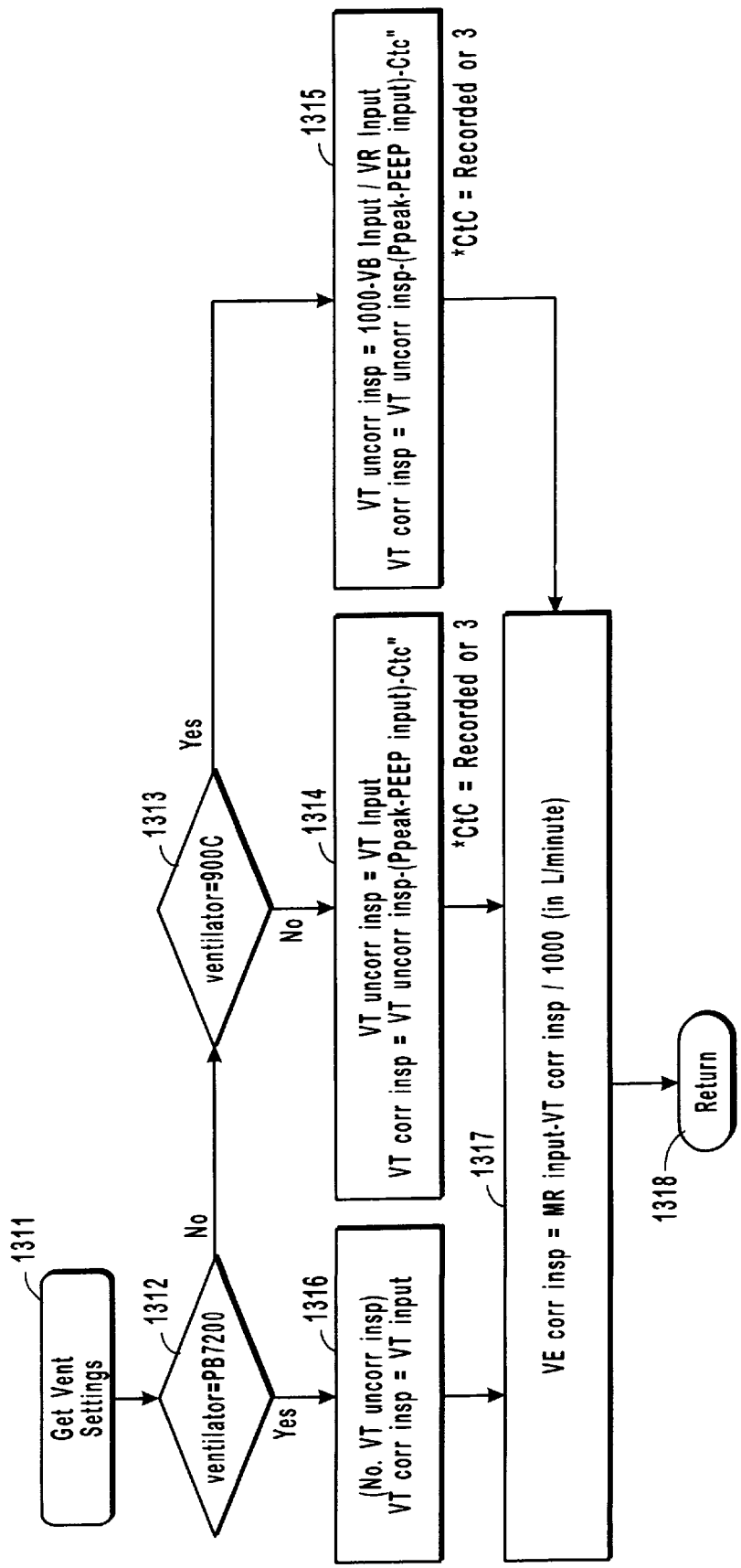
FIG. 13B is a flowchart diagram of the get vent settings protocol

The Increase VT Trial (Assisting Mode) protocol can be re-entered at step 1708 (from step 217 or 226 of PROVIEW). The Get Vent Settings protocol shown in FIG. 13B is called at step 1709. At step 1710 a check for cancellation of the trial is made. If the trial has been canceled, step 1717 is executed. If $VT_{corr\ insp}$ is greater than $VT_{baseline}$ (step 1717) and if $MR_{input}/MR_{baseline}$ is less than or equal to 0.8 or $MR_{input}$ is less than or equal to 35 (step 1718), $VT_{goal}$ is set to $VT_{corr\ insp}$ (step 1721). If $VT_{corr\ insp}$ is not greater than $VT_{baseline}$, $VT_{goal}$ is also set to $VT_{corr\ insp}$. If $MR_{input}/MR_{baseline}$ is greater than 0.8 and $MR_{input}$ is greater than 35 (step 1718), $VT_{goal}$ is set to $VT_{baseline}$ (step 1719). After executing step 1719, a check is made for cancellation of the trial or $MR_{input}$ greater than $VR_{input}$ (step 1720). If either of these situations have occurred, a message stating that the increase VT trial for assisting mode patients was unsuccessful and suggesting use of controlled mode ventilation is generated (step 1722). Following 1720 (if the conditions tested for were not true), step 1721 or step 1722, a message is generated stating "Increase VT Trial for Assisting patients completed", and Trial is set to No Trial (step 1723).

If at step 1710, the trial has not been canceled, the current time is compared to the trial time (step 1711). If the difference between the current time and the trial time is greater than 30 minutes, a message is generated stating that the increase VT Trial for Assisting patients was ended because the instructions were not completed within 30 minutes (step 1712). Following step 1712, step 1717 and subsequent steps are executed. If the difference between the current time and the trial time is less than 30 minutes, but $MR_{input}$ is not greater than $VR_{input}$ (step 1713), a message is generated stating that Increase VT Trial (assisting mode) was canceled because patient is not assisting (step 1714). Step 1717 and subsequent steps are then executed. If at step 1713, $MR_{input}$ was greater than $VR_{input}$, then step 1715 is executed.

If $VT_{corr\ insp}/BW_p$ is less than or equal to 9, $MR_{input}$ is greater 35, $pH_a$ input is less than 7.5 and $P_{plat}$ is less than 60 (step 1715), in step 1724 $VT_{corr\ insp}/BW_p$ is compared to 8. If it is less than or equal to 8, $VT_{goal}$ is set to $VT_{corr\ insp}+2*BW_p$ (step 1726). If $VT_{corr\ insp}/BW_p$ is greater than 8, then $VT_{goal}$ is set to $10*BW_p$ (step 1725). Following either step 1725 or 1726, a message is generated instructing that Total Ventilatory Rate, Peak and Plateau pressure be charted five minutes after making the changes (step 1727). The trial time is set to the current time (step 1728), the Set Ventilator Protocol is called (step 1729) and program control returns to the calling protocol from step 1730. If the conditions evaluated in step 1725 do not hold, the delay time is set to the current time plus 12 hours (step 1716), and step 1717 and subsequent steps are executed.

Increase VT Trial Assisting Mode in Progress:

The Increase VT Trial Controlled Mode Protocol is entered at step 1519 if it is already in progress. Entry at this point occurs when it is called from step 1304 of the CPPV ventilation protocol shown in FIG. 13A. First, a message is generated which states that an increase VT Trial is in progress (step 1520). $pH_a$ low is set to 7.25, $pH_a$ goal is set to 3.5, and [H] goal is set to 50 (step 1521). If $pH_a$ input is between 7.25 and 7.35 (step 1522), $VE_{goal}$ is set to $VE_{corr\ insp}$ (step 1523). Otherwise, $VE_{goal}$ is set to $VE_{corr\ insp}*(15.686275/10^{1.04167*pHa-6.4074})$ (step 1524). $VR_{temp}$ is then calculated as $VE_{goal}/(VT_{corr\ insp}/1000)$ (step 1525). If the trial has been canceled (step 1526) program control goes to step 1514, and this step and subsequent steps are carried out as described above. If the Trial is in a timeout (i.e., the current time minus the trial time is greater than 60 minutes) (step 1527) a message is generated which states that the increase VT trial was ended because trial instructions and ABG were not completed within an hour (step 1528). If the Trial is not in a Timeout, but $MR_{input}$ is greater than $VR_{input}$ (step 1529), a message is generated stating that the Increase VT Trial (controlled mode) was canceled because the patient was assisting (step 1530). Following step 1528 or 1530, program control goes to step 1514, as described above. If, at step 1529, $MR_{input}$ was not greater than $VR_{input}$ program control goes to step 1507, and this step and subsequent steps are carried out as described above. Program control eventually returns to the CPPV ventilation protocol from step 1512.

Set Ventilator

The Set Ventilator protocol is shown in FIG. 18. In this protocol, ventilator-specific executable instructions are generated for adjusting the settings on the ventilator. These settings include some or all of VR, VE, VT, insp Time % and Pause Time %, Peak Flow and I:E (depending on the make and model of the ventilator being used). The set ventilator protocol is entered at step 1801. $pH_a$ and $VR_{goal}$ are set (step 1802). If $VR_{goal}$ is greater than 35 (step 1803) and Mode equals Assisting (step 1804), a message is generated which states that an excessive VR is required to maintain $pH_a$ if the patient stops assisting (step 1805). If Mode does not equal assisting, a message is generated which states that an excessive VR is required to maintain $pH_a$ above $pH_{a\ low}$ (step 1806). If $VR_{goal}$ is less than 6 (step 1807) $VR_{goal}$ is set to $VR_{min}$ (step 1808). An instruction for the new VR setting is then generated and $VR_{set}$ is set to $VR_{goal}$ (step 1809). If the ventilator is a PB 7200 (step 1810) an instruction for a new VT setting equal to $VT_{goal}$ is issued (step 1822). If the ventilator is not a PB7200, $VT_{uncorr\ insp\ goal}$ is set to $VT_{goal}+[(VT_{goal}/VT_{corr\ insp})*P_{peak}-PEEP]*Ctc$ (step 1811). If the absolute value of $(VT_{uncorr\ insp\ goal}-VT_{uncorr\ insp})$ divided by $VT_{uncorr\ insp}$ is less than 0.05 (step 1812); $VT_{uncorr\ insp\ goal}$ is set to $VT_{uncorr\ insp}$ (step 1813). If the ventilator is a 900C (step 1814) instructions for a new VE setting are generated, with $VE_{set}=(VT_{uncorr\ insp\ goal}/1000)*VR_{set}$ (step 1815). If the ventilator is not a 900C, an instruction for a new VT setting is generated, with $VT_{set}$ equal $VT_{uncorr\ insp\ goal}$ (step 1821). After either step 1821 or step 1822, if $VT_{set}=VT_{input}$ and $VR_{set}=VR_{input}$ (step 1823) the I:E ratio is considered. If it is between 1.8 and 2.8 (step 1832), program control returns to the calling protocol from step 1831. If not, if vent=H.Veolar (step 1833), Insp time is set to 33% (step 1834) and program control returns to the calling protocol from step 1831. If vent is not H. Veolar, a message is generated stating "set peak flow to maintain an I:E ratio between 1:1.8 and 1:2.8" (step 1835). If at step 1823, $VT_{set}=VT_{input}$ and $VR_{set}=VR_{input}$ are not both true, in step 1824 it is determined whether $VT_{set}=VT_{input}$ $pH_a$ input$\geq pH_{a\ low}$ and mode=assisting. If these conditions are all true, a message is generated stating that a change in backup VR, but no ABG, is needed (step 1825). Following step 1825, step 1832 and if appropriate, any subsequent steps are carried out. If the conditions tested at step 1824 are not true, and vent is not H.Veolar (step 1826) a message is generated stating "set peak flow to maintain an I:E ratio between 1:1.8 and 1:2.8 (step 1828). If vent equals H.Veolar, insp time is set to 33% (step 1827). If an Increase VT Trial (assisting) is currently in progress (step 1829), program control returns to the calling protocol from step 1831. If not, a message instructing that an ABG be drawn 20 minutes after making changes is generated (step 1830) and the protocol returns to the calling protocol from step 1831. If the ventilator is a 900C, after the new VE setting is set in step 1815, if Insp time %=25% and Pause Time %=5% or if Insp time=33% (step 1816), then step 1818 is executed. If not, Insp Time % is set to 25% and Pause time % is set to 5% (step 1817), prior to executing step 1818. In step 1818, $VE_{set}$ is compared to $VE_{input}$ and $VR_{set}$ is compared to $VR_{input}$. If the compared values are equal, program control returns to the calling protocol form step 1831. If the compared values are not equal, additional step are carried out: if $pH_a$ input is greater than or equal to $pH_{a\ low}$, $VT_{uncorr\ insp\ goal}$ equals $VT_{uncorr\ insp}$ and mode=assisting (step 1819), a message is generated which states that a change in backup ventilatory rate, but no ABG is needed (step 1820), and program control returns to the calling protocol from step 1931. If not, step 1829, and if appropriate, step 1830 are carried out before the program returns to the calling protocol.

When the trial is completed, the ventilator is set and program control returns to PROVIEW. Any instructions generated are stored, and the program waits until a further command or data are entered which again initiate operation of one or more of the protocols. If one of the VT trials is being performed, and the cancel Trial Option is selected, program control returns to PROVIEW at step 221. If the trial which was canceled was an Increase VT Trial:Assisting, steps 222, 223, 224 and 226 of Proview are carried out, as has been described previously. If the canceled trial was an increase VT Trial: Controlled, steps 222, 223 are carried out as described previously and the CORE is called at step 204.

When Proview has completed running any instructions generated by the various protocols are stored. The clinician may review the instructions at any time. In the present example, said instructions are not displayed on the computer terminal as they are generated, but are stored until it is requested that they be displayed. This leaves the screen free for other tasks. A small marker is displayed on the screen to inform the clinician that there are stored messages.

The stored instructions, and the time at which they were carried out are saved permanently as a record of patient treatment.

EXAMPLE 2

Paper Protocols

The invention may be practiced with protocols written on paper. In this case any calculations, comparisons, or logical decisions must be carried out by the clinician instead of being performed automatically by the computer. Patient data used in the calculations and comparisons could be displayed on a screen of a hospital information system, listed on a sheet of paper, or made available to the clinician by some other means. Acceptance or rejection of the proposed treatment by the clinician is then recorded by the clinician, for example on a piece of paper. The protocols shown in FIGS. 2–23 can used in this way by beginning with the PROVIEW protocol shown in FIG. 2 and working through the logic of the protocols, step by step. This embodiment of the invention is less preferred than the embodiment presented in Example 1; however, in cases where an appropriate computerized system is not available, useful results can be obtained with this embodiment of the invention. In general, this approach is more suitable when a relatively simple protocol set (for example, a subset of the protocols shown in FIGS. 2 through 23) is to be used.

Protocol Subsets

While the inventive system described herein utilizes a number of protocols which are accessed from within a single program, in some cases it may be preferable to use only one or some of the protocols, and in these cases it would be preferred to alter the program used by the invention so that only the protocol or protocols of interest were accessed. Alternatively, it may be desirable to use a subset of the protocols on paper, as described in Example 2. The $SpO_2$, weaning assessment and weaning trial protocols could be used independently. The following protocols could be used individually but would most appropriately be used in the following combinations:

CPAP Oxygenation Reduction and CPAP Oxygenation Increase

CPPV Oxygenation Reduction and CPPV Oxygenation Increase

CPPV Assisting Mode Ventilation and Increase VT Trial assisting

CPPV Controlled Mode Ventilation and Increase VT Trial controlled

Furthermore, although these combinations are considered to be particularly useful, other combinations of protocols may be used without departing from the inventive concept.

Conclusion

The scope of the present invention is not limited to systems which utilize all of the protocols described herein; the invention is also considered to comprise systems which utilizes a subset of the protocols. Although the present invention was designed particularly for patients with ARDS, it is suitable for use in the management of most patients with severe respiratory failure. Because it is presently configured to manage the patient such that pH is kept low and $PaCO_2$ is high, it would not be suitable for use in patients with head trauma or chronic obstructive pulmonary disease. However, if it was modified so that pH and $PaCO_2$ were maintained at higher levels it could be used with such patients.

While the invention has been described in detail with respect to specific preferred embodiments of the present invention, variations and modifications are comprehended to be included in the disclosed invention. The invention may be embodied in other specific forms without departing from its spirit or essential characteristics. The described embodiments are to be considered in all respects as only illustrative, and not restrictive. The scope of the invention is, therefore, indicated by the appended claims, rather than the foregoing description. All changes which come within the meaning and range of equivalency of the claims are to be embraced within their scope.

We claim:

1. A method for controlling oxygenation and ventilation of a patient with a respiratory disorder, the method comprising the steps of:

a) acquiring patient data relating to the condition of the patient, the patient's lungs, ventilatory assistance parameters, and patient treatment;

b) processing said patient data according to a first protocol set, said first protocol set comprising a logically ordered set of rules for making a first patient treatment decision, to obtain a specific, executable first instruction for adjusting a ventilatory assistance parameter selected from the group consisting of: Fraction of Inspired Oxygen, wherein said Fraction of Inspired Oxygen is the percent of gas by volume that is oxygen inspired by said patient, and Positive End Expiratory Pressure, wherein said Positive End Expiratory Pressure is the pressure that remains in said patient's lungs at the end of the exhaling by said patient;

c) Processing said patient data according to a second protocol set, said second protocol set comprising a logically ordered set of rules for making a second patient treatment decision, to obtain a specific, executable second instruction for adjusting a ventilatory assistance parameter selected from the group consisting of: size of breath, number of breaths per minute, and peak gas flow rate during inspiration;

d) presenting said first instruction and said second instruction to a clinician;

e) recording acceptance or rejection of said first instruction and said second instruction by said clinician; and f) carrying out said instruction if it has been accepted by said clinician.

2. A method in accordance with claim 1, further comprising the step of:

g) repeating steps b) through f) whenever a data item is acquired.

3. A method in accordance with claim 1, further comprising the steps of:

g) monitoring an input device for instructions from said clinician; and h) repeating steps b) through f) whenever an instruction is received at said input device requesting that steps b) through e) be carried out.

4. A method in accordance with claim 1, wherein step b) further comprises classifying the oxygenation of the patient by performing the following steps:

i) determining whether the patient has barotrauma;
ii) if said patient has barotrauma, performing the steps of:
1) assigning said oxygenation level to a first category if arterial partial oxygen pressure is less than about 50 mm Hg;
2) assigning said oxygenation level to a second category if said arterial partial oxygen pressure is between about 50 mm Hg and about 55 mm Hg;
3) assigning said oxygenation level to a third category if said arterial partial oxygen pressure is between about 55 mm Hg and about 60 mm Hg;
4) assigning said oxygenation level to a fourth category if said arterial partial oxygen pressure is between about 60 mm Hg and about 110 mm Hg; and
5) assigning said oxygenation level to a fifth category if said arterial partial oxygen pressure is greater than 110 mm Hg;
iii) if said patient does not have barotrauma, performing the steps of:
1) assigning said oxygenation level to said first category if arterial partial oxygen pressure is less than about 50 mm Hg;
2) assigning said oxygenation level to said second category if said arterial partial oxygen pressure is between about 50 mm Hg and about 60 mm Hg;
3) assigning said oxygenation level to said third category if said arterial partial oxygen pressure is between about 60 mm Hg and about 68 mm Hg;
4) assigning said oxygenation level to said fourth category if said arterial partial oxygen pressure is between about 68 mm Hg and about 110 mm Hg; and
5) assigning said oxygenation level to said fifth category if said arterial partial oxygen pressure is greater than 110 mm Hg;
wherein the generation of said specific, executable instruction is dependent upon the category into which said oxygenation level is assigned.

5. A method in accordance with claim 4, wherein said first category is defined as "Threatening", wherein said second category is defined as "Marginal", wherein said third category is defined as "Acceptable", wherein said fourth category is defined as "Satisfactory", and wherein said fifth category is defined as "Super-Satisfactory.

6. A method in accordance with claim 1, wherein step a) comprises the steps of:
i) measuring pulse oximeter arterial oxygen saturation data and
ii) measuring blood gas arterial oxygen saturation data; and wherein step b) comprises estimating the current value of arterial partial oxygen pressure from the current pulse oximeter arterial oxygen saturation value, according to the steps of:
i) setting the estimated current arterial partial oxygen pressure value to a predetermined constant value in the "threatening" oxygenation class if the current pulse oximeter arterial oxygen saturation is less than a predetermined minimum value;
ii) calculating the pulse oximeter arterial oxygen saturation measurement error as the difference between said pulse oximeter arterial oxygen saturation data measured with a pulse oximeter and said blood gas arterial oxygen saturation data measured from an Arterial Blood Gas, said Arterial Blood Gas being drawn at the same time as said pulse oximeter arterial oxygen saturation data were measured;
iii) creating an oxyhemoglobin dissociation curve from said blood gas arterial oxygen saturation data and from arterial partial oxygen pressure data from said Arterial Blood Gas;
iv) estimating the shift in said oxyhemoglobin dissociation curve relative to a normal oxyhemoglobin dissociation curve;
v) determining a current arterial partial oxygen pressure estimate from said current pulse oximeter arterial oxygen saturation, taking into account said shift of said oxyhemoglobin dissociation curve and said pulse oximeter arterial oxygen saturation measurement error;
wherein said current arterial partial oxygen pressure estimate is considered reliable if said pulse oximeter arterial oxygen saturation measurement error is less than a predetermined minimum value, said arterial partial oxygen pressure from said Arterial Blood Gas was obtained more recently that the current time less a predetermined time value, the Positive End Expiratory Pressure is less than a predetermined minimum value, and the Fraction of Inspired Oxygen is less than a predetermined minimum value.

7. A method in accordance with claim 1, further comprising the step of:
g) providing the patient with Continuous Positive Airway Pressure, wherein said Continuous Positive Airway Pressure is the condition where a positive pressure gas source is used by said patient who breathes without further ventilation assistance; wherein oxygenation of said patient is controlled by alternatively adjusting Fraction of Inspired Oxygen and Positive End Expiratory Pressure.

8. A method in accordance with claim 4, further comprising the step of:
iv) providing the patient with Continuous Positive Airway Pressure;
wherein said specific, executable instruction obtained in step b) is an instruction for adjusting said oxygenation of said patient by performing in step b) the further steps of:
iv) If oxygenation is in either of said first or second categories, increasing oxygenation by alternately increasing Fraction of Inspired Oxygen and Continuous Positive Airway Pressure rapidly until oxygenation is in said third category, waiting about 2 hours after a Continuous Positive Airway Pressure increase before increasing again if oxygenation was in said second category, and waiting about 15 minutes if oxygenation was in said first category;
v) if oxygenation is in one of said third, fourth or fifth categories, identifying the lowest level of Fraction of Inspired Oxygen and Continuous Positive Airway Pressure capable of maintaining oxygenation in said third category by alternately reducing Fraction of Inspired Oxygen and Continuous Positive Airway Pressure slowly until oxygenation temporarily falls below the threshold for said third category, and then increasing Fraction of Inspired Oxygen and Continuous Positive Airway Pressure and waiting before attempting further reduction, wherein each successive time a decrease in Fraction of Inspired Oxygen or Continuous Positive Airway Pressure fails, a longer waiting time is used before making a further decrease; and
v) if oxygenation is in one of said fourth or fifth categories, decreasing oxygenation by reducing Continuous Positive Airway Pressure, and waiting about 6 hours after a Continuous Positive Airway Pressure increase before attempting to reduce Continuous Positive Airway Pressure;
wherein said patient is provided with Continuous Positive Airway Pressure as long as arterial pH is greater than or equal to about 7.30 and ventilatory rate is less than or equal to about 36 breaths per minute.

9. A method in accordance with claim 1, further comprising the step of:

f) providing the patient with Controlled Positive Pressure Ventilation, wherein said Controlled Positive Pressure Ventilation is the condition wherein the ventilator provides positive pressure airway ventilation delivered in a fixed breathing pattern to said patient wherein said breathing pattern thereby enabling the breathing of said patient; wherein oxygenation of said patient is controlled by alternately adjusting Fraction of Inspired Oxygen and Positive End Expiratory Pressure.

10. A method in accordance with claim 4, further comprising the step of:

iv) providing the patient with Controlled Positive Pressure Ventilation;

wherein said specific, executable instruction obtained in step b) is an instruction for adjusting oxygenation of said patient by performing in step b) the further steps of:

iv) If oxygenation is in either one of said first or second categories, increasing oxygenation by alternately increasing Fraction of Inspired Oxygen and Positive End Expiratory Pressure rapidly until oxygenation is in said third category, waiting about 2 hours after a Positive End Expiratory Pressure increase before increasing again if oxygenation was in said second category and waiting about 15 minutes if oxygenation was in said first category;

v) If oxygenation is in one of said third, fourth or fifth categories, identifying the lowest levels of Fraction of Inspired Oxygen and Positive End Expiratory Pressure and waiting before attempting further reductions, alternately reducing Fraction of Inspired Oxygen and Positive End Expiratory Pressure slowly until oxygenation temporarily falls below the threshold for said third category, and then increasing Fraction of Inspired Oxygen and Positive End Expiratory Pressure and waiting before attempting further reductions, wherein each successive time a decrease in Fraction of Inspired Oxygen or Continuous Positive Airway Pressure fails, a longer waiting time is used before making a further decrease;

vi) If oxygenation is in either one of said fourth or fifth categories, decreasing oxygenation by reducing Positive End Expiratory Pressure, and waiting about 6 hours after a Positive End Expiratory Pressure increase before attempting to reduce Positive End Expiratory Pressure.

\* \* \* \* \*